United States Patent
Xu et al.

(10) Patent No.: US 12,287,328 B2
(45) Date of Patent: Apr. 29, 2025

(54) FULLY AUTOMATED CHEMILUMINESCENCE IMMUNOASSAY ANALYZER

(71) Applicants: CHENGDU SHEN MINDRAY MEDICAL ELECTRONICS TECHNOLOGY RESEARCH INSTITUTE CO., LTD., Chengdu (CN); SHENZHEN MINDRAY BIO-MEDICAL ELECTRONICS CO., LTD., Shenzhen (CN)

(72) Inventors: Huaming Xu, Shenzhen (CN); Yundong Qi, Shenzhen (CN); Wangfu Chen, Shenzhen (CN); Meng Xian, Shenzhen (CN); Gansong Shen, Shenzhen (CN); Zhibin Cheng, Shenzhen (CN); Jianjun Peng, Shenzhen (CN)

(73) Assignees: CHENGDU SHEN MINDRAY MEDICAL ELECTRONICS TECHNOLOGY RESEARCH INSTITUTE CO., LTD., Chengdu (CN); SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 1144 days.

(21) Appl. No.: 16/938,888

(22) Filed: Jul. 24, 2020

(65) Prior Publication Data

US 2020/0355676 A1   Nov. 12, 2020

Related U.S. Application Data

(63) Continuation of application No. PCT/CN2019/074486, filed on Feb. 1, 2019.

(30) Foreign Application Priority Data

Feb. 8, 2018 (CN) .......................... 201810130696.8
Mar. 26, 2018 (CN) .......................... 201810253017.6

(51) Int. Cl.
G01N 33/53   (2006.01)
C12M 1/12   (2006.01)
(Continued)

(52) U.S. Cl.
CPC ......... *G01N 33/5304* (2013.01); *C12M 37/00* (2013.01); *G01N 35/025* (2013.01); *G01N 2035/0444* (2013.01)

(58) Field of Classification Search
CPC ............. G01N 33/5304; G01N 35/025; G01N 2035/0444; G01N 35/1002;
(Continued)

(56) References Cited

U.S. PATENT DOCUMENTS 5,580,524 A * 12/1996 Forrest ................. G01N 35/025
436/174
5,622,831 A   4/1997 Liberti et al.
(Continued)

FOREIGN PATENT DOCUMENTS

CN   101208153 A   6/2008
CN   101275967 A   10/2008
(Continued)

OTHER PUBLICATIONS

International Search Report issued in corresponding International Application No. PCT/CN2019/074486, mailed Apr. 29, 2019, 6 pages.
(Continued)

*Primary Examiner* — Matthew D Krcha
*Assistant Examiner* — Sophia Y Lyle
(74) *Attorney, Agent, or Firm* — Kory D. Christensen

(57) ABSTRACT

A fully automated chemilumiescence immunoassay analyzer, including a sample and reagent receiving device for receiving a sample and a reagent, a dispensing device for aspirating and discharging the sample and the reagent, a mixing device for mixing the sample and the reagent in a reaction vessel, an incubation and luminescence detection device for incubation and luminescence detection, a magnetic separation cleaning device for separation cleaning an analyte and impurities in the reaction vessel, a reaction vessel grasping device for transferring the reaction vessel, and a liquid path device. The fully automated chemiluminescence immunoassay analyzer has a simple structure and is convenient to operate, and also reduce the overall size such that the footprint thereof is small and the production (Continued)

cost is reduced, so that the analyzer is easy to achieve miniaturization, and is convenient for an operator to use.

22 Claims, 8 Drawing Sheets

(51) Int. Cl.
    *G01N 35/02*     (2006.01)
    *G01N 35/04*     (2006.01)

(58) Field of Classification Search
    CPC .......... G01N 2035/00356; G01N 2035/00445; G01N 2035/00524; G01N 2035/00831; G01N 35/0098; G01N 2035/0437; G01N 2035/0441; G01N 2035/0443; G01N 35/10; C12M 37/00; B03C 1/01; B03C 1/0332; B03C 1/288; B03C 2201/18; B03C 2201/22; B03C 2201/26
    See application file for complete search history.

(56) References Cited

U.S. PATENT DOCUMENTS

| | | | |
|---|---|---|---|
| 6,231,760 B1 * | 5/2001 | Siddiqi | B03C 1/288 366/273 |
| 6,555,062 B1 * | 4/2003 | Lewis | G01N 35/021 422/549 |
| 2005/0013737 A1 | 1/2005 | Chow et al. | |
| 2006/0051243 A1 | 3/2006 | Chow et al. | |
| 2012/0064638 A1 * | 3/2012 | Onomichi | G01N 35/0092 436/501 |
| 2012/0138099 A1 * | 6/2012 | Jafari | G01N 35/1004 134/21 |
| 2013/0164853 A1 * | 6/2013 | Belz | B01L 9/543 422/68.1 |

FOREIGN PATENT DOCUMENTS

| | | | | |
|---|---|---|---|---|
| CN | 102279275 A | * | 12/2011 | |
| CN | 103443629 A | | 12/2013 | |
| CN | 103592450 A | | 2/2014 | |
| CN | 104111341 A | | 10/2014 | |
| CN | 104714042 A | | 6/2015 | |
| CN | 104722526 A | * | 6/2015 | |
| CN | 104777321 A | | 7/2015 | |
| CN | 205067505 U | | 3/2016 | |
| CN | 205404415 U | | 7/2016 | |
| CN | 205608010 U | * | 9/2016 | |
| CN | 106199025 A | * | 12/2016 | |
| CN | 106324265 A | | 1/2017 | |
| CN | 106645765 A | | 5/2017 | |
| CN | 208172026 U | | 11/2018 | |
| CN | 208297537 U | | 12/2018 | |
| JP | 2016206113 A | * | 12/2016 | |
| TW | 201035553 A | * | 10/2010 | ................ B01L 9/06 |
| WO | WO2012130107 A1 | | 10/2012 | |
| WO | 2016046402 A1 | | 3/2016 | |

OTHER PUBLICATIONS

"Nuclear Physics Experimental Method," published on Apr. 30, 1981, by Fudan University, Qinhua University, and Bejing University atomic energy publisher, pp. 218-220.

* cited by examiner

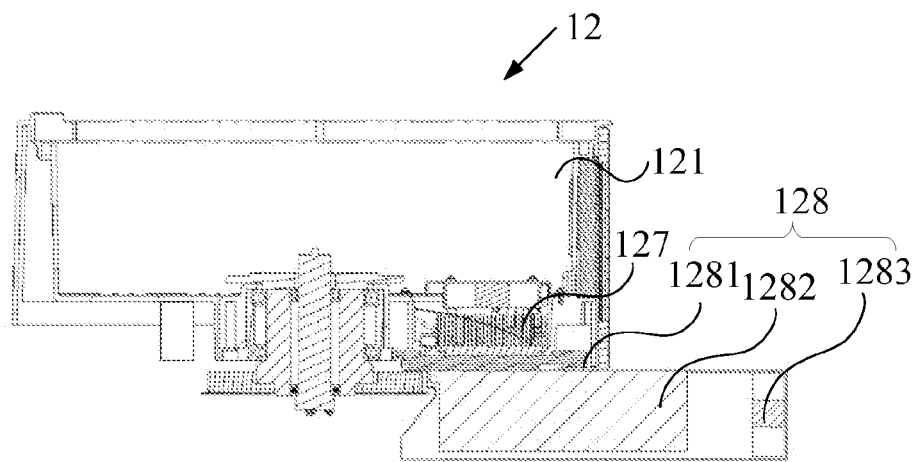
FIG. 7
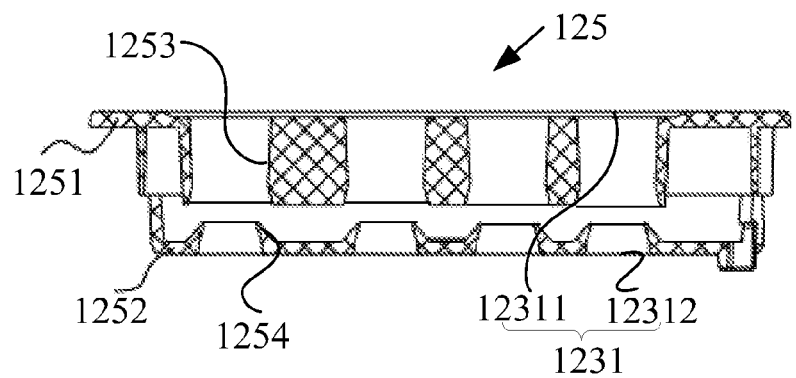
FIG. 8
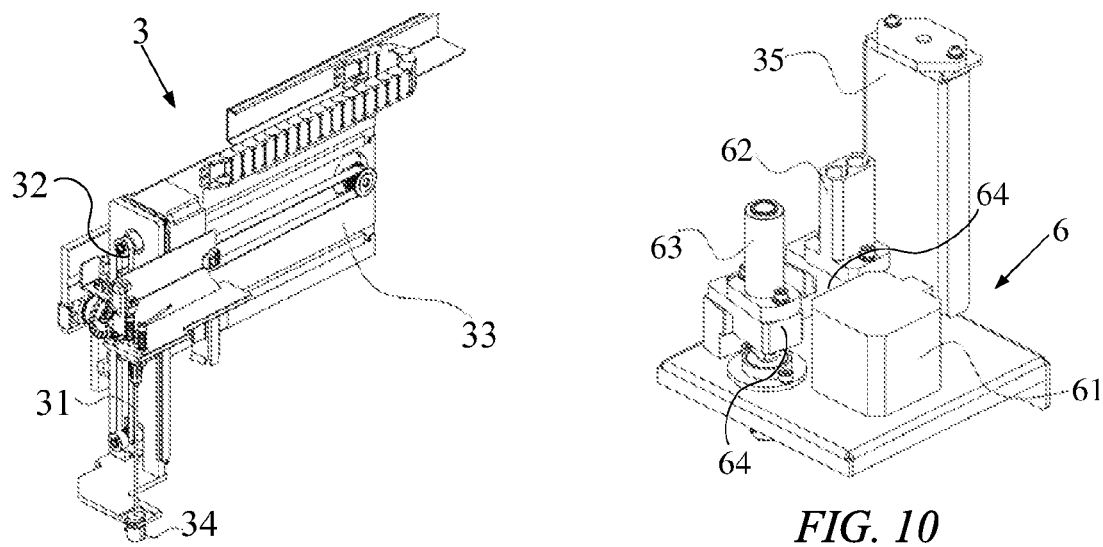
FIG. 9
FIG. 10

FULLY AUTOMATED CHEMILUMINESCENCE IMMUNOASSAY ANALYZER

CROSS-REFERENCE TO RELATED APPLICATIONS

This application is a bypass continuation of PCT Application No. PCT/CN2019/074486, filed Feb. 1, 2019, which claims priority to Chinese Patent Application No. 201810130696.8, filed on Feb. 8, 2018, and Chinese Patent Application No. 201810253017.6, filed on Mar. 26, 2018, the entire contents of which are incorporated herein by reference.

TECHNICAL FIELD

The present disclosure relates to the technical field of chemiluminescence detection, and in particular to a fully automatic chemiluminescence immunoassay analyzer.

BACKGROUND

Chemiluminescence immunoassay technology is a highly sensitive and highly specific analytical instrument that has developed rapidly in the world in the past decade, and is used in clinical laboratories to detect various immunity indexes of blood, urine, or other body fluids. The principle is to combine two technologies, namely antibody antigen reaction and chemiluminescence, to achieve high specificity and high sensitivity. The main operation procedures in chemiluminescence analyzers comprise sample receiving, reagent receiving, sample and reagent dispensing, reaction solution mixing, reaction solution incubation, magnetic separation cleaning separation, substrate luminescent solution injection, and luminescence detection. At present, chemiluminescence immunoassay analyzers generally have the disadvantages of complex structures, large footprints, high costs, and low test fluxes, which affect the use thereof.

SUMMARY

On this basis, there is a need to provide a fully automatic chemiluminescence immunoassay analyzer having a simple structure, reduced overall size and reduced production cost for the problems of complex structures, large footprints and high costs of the current chemiluminescence immunoassay analyzers.

The foregoing objectives are achieved by the following technical solutions:
a fully automatic chemiluminescence immunoassay analyzer comprising a sample and reagent receiving device for receiving a sample and a reagent, a dispensing device for aspirating and discharging the sample and the reagent, a mixing device for mixing the sample and the reagent in a reaction vessel, an incubation and luminescence detection device for incubation and luminescence detection, a magnetic separation cleaning device for separation cleaning an analyte and impurities in the reaction vessel, a reaction vessel grasping device for transferring the reaction vessel, and a liquid path device, wherein the sample and reagent receiving device comprises a sample receiving mechanism for receiving the sample and a reagent receiving mechanism for receiving the reagent, the sample receiving mechanism is sleeved outside the reagent receiving mechanism, and the sample receiving mechanism and the reagent receiving mechanism are capable of rotating independently of each other;

the reaction vessel grasping device transfers the reaction vessel into the mixing device; the dispensing device is located above the sample and reagent receiving device, and is able to respectively transfer the sample and the reagent into the reaction vessel in the mixing device; the reaction vessel grasping device transfers the reaction vessel from the mixing device to the incubation and luminescence detection device to perform incubation, and the reaction vessel grasping device further transfers the reaction vessel subjected to the incubation to the magnetic separation cleaning device to perform separation cleaning, and transfers the reaction vessel subjected to the separation cleaning into the incubation and luminescence detection device to perform luminescence detection; and the liquid path device is respectively connected to the dispensing device and the magnetic separation cleaning device, and the liquid path device is further used to inject or discharge a cleaning liquid into or from the magnetic separation cleaning device.

In one of the embodiments, the sample receiving mechanism further comprises a plurality of sample holders arranged in an arc shape, a sample receiving driving structure, and a chassis, wherein each of the sample holders is configured to carry a sample vessel with a sample, the plurality of sample holders are sequentially installed on the chassis, and the sample receiving driving structure drives the chassis to rotate, and drives the sample holders to rotate.

In one of the embodiments, the sample receiving mechanism further comprises a needle cleaning structure for cleaning the dispensing device, the needle cleaning structure being provided on the chassis and located between adjacent two of the sample holders.

In one of the embodiments, the reagent receiving mechanism comprises a reagent housing, a reagent disc, and a reagent disc driving structure, wherein the reagent disc is accommodated in the reagent housing, the reagent disc is configured to store reagent vessels with reagents, and the reagent disc driving structure drives the reagent disc to rotate.

In one of the embodiments, the sample and reagent receiving device further comprises an identification code scanner for scanning identification codes, and the sample receiving mechanism is provided with a scanning notch; and
the identification code scanner is able to scan identification codes of the sample vessels on the sample receiving mechanism, and the identification code scanner is also able to scan identification codes of the reagent vessels on the reagent receiving mechanism through the scanning notch.

In one of the embodiments, the identification code scanner is fixedly arranged on an outer side of the sample receiving mechanism, and the sample receiving mechanism drives the sample vessels to sequentially rotate to the identification code scanner to perform scanning; and when the scanning notch corresponds to the identification code scanner, the reagent receiving mechanism drives the reagent vessels to sequentially rotate to the scanning notch to perform scanning.

In one of the embodiments, there is a preset spacing between adjacent two of the sample holders to form the scanning notch, the reagent housing is provided with a scanning window, and when the scanning window, the scanning notch and the identification code scanner correspond to one another, the reagent disc drives the multiple reagent vessels to rotate, such that the reagent vessels sequentially move to the scanning window, and the identification code scanner scans the identification codes of the reagent vessels.

In one of the embodiments, the reagent receiving mechanism further comprises a cooling structure, wherein the cooling structure comprises a cooling component, and the cooling component is located below the reagent disc and offset from the center of the reagent housing for cooling the interior of the reagent housing.

In one of the embodiments, the cooling structure further comprises a cold-end spreader, which is connected to a cold end of the cooling component and located below the reagent disc.

In one of the embodiments, the reagent receiving mechanism further comprises a hot-end radiator and a heat-conducting component, wherein the hot-end radiator is connected to a hot end of the cooling component and located on an outer side of the reagent housing; and the heat-conducting component is connected to the hot-end radiator and corresponds to an outer side of the scanning window.

In one of the embodiments, the reagent receiving mechanism further comprises a reagent housing lid, wherein the reagent housing lid covers the reagent housing; and
the reagent housing lid is provided with a plurality of reagent aspiration holes, which are arranged in a radial direction of the reagent disc and located on a straight line, and the dispensing device is able to extend into any one of the reagent aspiration holes to aspirate a reagent.

In one of the embodiments, the reagent receiving mechanism further comprises a switching cover, the reagent housing lid is provided with a placement/removal opening for placing or removing the reagent vessel, and the switching cover is switchably located in the placement/removal opening of the reagent housing lid.

In one of the embodiments, the reagent housing lid further comprises a condensation structure, wherein the condensation structure is provided on the reagent housing lid, the reagent aspiration holes are located in the condensation structure, and the condensation structure is configured to receive condensed water generated at the reagent aspiration holes;
the condensation structure comprises a condensation plate and a water receiving tray arranged opposite each other, the condensation plate is detachably connected to the water receiving tray, an airflow channel is formed between the condensation plate and the water receiving tray, and cold air in the reagent housing is able to enter the airflow channel;
the reagent aspiration holes comprise a first reagent aspiration hole located in the condensation plate and a second reagent aspiration hole located in the water receiving tray; and the first reagent aspiration hole and the second reagent aspiration hole are arranged opposite each other, the outline of the first reagent aspiration hole is able to completely cover the outline of the second reagent aspiration hole, and the first reagent aspiration hole is respectively in communication with the airflow channel and an outside environment.

In one of the embodiments, a hole wall of the first reagent aspiration hole extends toward the water receiving tray to form a first annular cylinder wall, an inner wall face of the first annular cylinder wall is in contact with the outside environment via the first reagent aspiration hole, and an outer wall face of the first annular cylinder wall is in contact with an environment where the airflow channel is located; and
the outline of one end of the first annular cylinder wall away from the first reagent aspiration hole is able to completely cover the outline of the second reagent aspiration hole.

In one of the embodiments, a hole wall of the second reagent aspiration hole extends toward the condensation plate to form a second annular cylinder wall;
the second annular cylinder wall is in the shape of a constriction in a direction from the second reagent aspiration hole toward the condensation plate; and
the water receiving tray is provided with a water discharge hole, the bottom of the reagent housing is provided with a water discharge channel for discharging the condensed water, and the water discharge hole is in communication with the water discharge channel.

In one of the embodiments, the fully automated chemiluminescence immunoassay analyzer further comprises a mixing device for mixing, wherein the mixing device comprises a mixing mechanism and a mixing drive mechanism, and the mixing drive mechanism drives the mixing mechanism to move, so as to mix the sample and the reagent in the reaction vessel on the mixing device.

In one of the embodiments, the number of the mixing mechanisms is two, the mixing seat comprises a reagent and sample mixing seat and a substrate mixing seat, the reagent and sample mixing seat is configured to carry at least one reaction vessel with the sample and the reagent and to mix the sample and the reagent in the reaction vessel, the substrate mixing seat is configured to carry a reaction vessel with a substrate and to mix an analyte and the substrate in the reaction vessel, and the mixing drive mechanism respectively drives, via the two mixing mechanisms, the reagent and sample mixing seat and the substrate mixing seat to perform mixing operations simultaneously.

In one of the embodiments, the dispensing device comprises a dispensing needle, a horizontal movement mechanism and a vertical movement mechanism, wherein the vertical movement mechanism is provided on the horizontal movement mechanism, the dispensing needle is provided on the vertical movement mechanism and is in communication with the liquid path device, and the movements of the vertical movement mechanism and the horizontal movement mechanism cause the dispensing needle to transfer the sample and the reagent between the sample and reagent receiving device and the mixing device.

In one of the embodiments, the dispensing device further comprises a first cleaning mechanism connected to the horizontal movement mechanism, wherein the first cleaning mechanism is in communication with the liquid path device, the horizontal movement mechanism also drives the first cleaning mechanism to move, and when the vertical movement mechanism drives the dispensing needle to ascend and descend, the first cleaning mechanism cleans an outer wall of the dispensing needle.

In one of the embodiments, the dispensing device further comprises a second cleaning mechanism, wherein the second cleaning mechanism is connected to the liquid path device, and the second cleaning mechanism is configured to receive a waste cleaning liquid after an inner wall of the dispensing needle is cleaned, and the waste cleaning liquid is discharged by the liquid path device.

In one of the embodiments, the sample and reagent receiving device is provided with a sample aspiration station, and is further provided with a plurality of reagent aspiration holes; the mixing device is provided with a reagent and sample mixing seat; and the sample aspiration station, a plurality of the reagent aspiration holes and the reagent and sample mixing seat are collinear with the second cleaning mechanism.

In one of the embodiments, the dispensing device comprises a dispensing needle, and the fluid path device comprises a dispensing liquid path system; the dispensing liquid path system comprises a dispensing power source, a dispensing aspiration/discharge pipeline, and a first dispensing control valve;

the first dispensing control valve is connected between the dispensing power source and the dispensing aspiration/discharge pipeline for controlling the connection and disconnection between the dispensing power source and the dispensing aspiration/discharge pipeline; and the dispensing aspiration/discharge pipeline is also connected to the dispensing needle, and when the first dispensing control valve communicates the dispensing aspiration/discharge pipeline with the dispensing power source, the dispensing needle aspirates and discharges the sample and the reagent, and an inner wall of the dispensing needle is cleaned.

In one of the embodiments, the dispensing device further comprises a first dispensing cleaning mechanism;

the dispensing liquid path system further comprises a first dispensing cleaning pipeline connected to the first dispensing control valve and the first dispensing cleaning mechanism; and the first dispensing control valve disconnects the dispensing power source from the dispensing aspiration/discharge pipeline while communicating the first dispensing cleaning pipeline with the dispensing power source, to clean an outer wall of the dispensing needle.

In one of the embodiments, the dispensing liquid path system further comprises a second dispensing control valve and a second dispensing cleaning pipeline, wherein the second dispensing control valve is connected to the dispensing power source and the first dispensing control valve, the second dispensing control valve is also connected to the second dispensing cleaning pipeline, and the second dispensing cleaning pipeline is also in communication with a cleaning liquid container with a cleaning liquid; and the second dispensing control valve disconnects the dispensing power source from the first dispensing control valve while communicating the dispensing power source with the second dispensing cleaning pipeline, to aspirate the cleaning liquid from the cleaning liquid container.

In one of the embodiments, the dispensing liquid path system further comprises a first dispensing waste liquid discharge device, the first dispensing waste liquid discharge device being connected to the first cleaning mechanism for discharging waste cleaning liquid from the first dispensing cleaning mechanism.

In one of the embodiments, the dispensing device further comprises a second cleaning mechanism; and the dispensing liquid path system further comprises a second dispensing waste liquid discharge device, the second dispensing waste liquid discharge device being connected to the second cleaning mechanism for discharging waste cleaning liquid from the second cleaning mechanism.

In one of the embodiments, the dispensing device further comprises a second cleaning mechanism; and the dispensing liquid path system further comprises a first dispensing liquid discharge pipeline, a second dispensing liquid discharge pipeline, a third dispensing control valve and a waste liquid pump, wherein the first dispensing liquid discharge pipeline is in communication with the first dispensing cleaning mechanism, the second dispensing liquid discharge pipeline is in communication with the second cleaning mechanism, the first dispensing liquid discharge pipeline and the second dispensing liquid discharge pipeline are also in communication with the waste liquid pump via the third dispensing control valve, and the waste cleaning liquid is discharged into a waste liquid bucket by the waste liquid pump.

In one of the embodiments, the incubation and luminescence detection device comprises a sample incubation mechanism and a sample detection mechanism, wherein the sample detection mechanism is provided on the sample incubation mechanism, and the reaction vessel subjected to the incubation is detected by the sample detection mechanism;

the sample incubation mechanism further comprises an incubation block and a heating component provided below the incubation block, the heating component is configured to heat the incubation block, the incubation block is provided with a plurality of incubation holes arranged in an array, and the incubation hole is configured to receive the reaction vessel; and the sample detection mechanism is mounted to a side face of the incubation block, and arranged side by side with the magnetic separation cleaning device.

In one of the embodiments, the sample incubation mechanism further comprises a temperature sensor and a temperature switch, wherein the temperature sensor is provided on the incubation block for detecting the temperature of the incubation block and controlling the heating temperature of the heating component for the incubation block; and the temperature switch is provided on the incubation block, and the temperature switch is configured to control the heating component to stop heating.

In one of the embodiments, the incubation block is further provided with a luminescence detection hole arranged corresponding to the sample detection mechanism, the reaction vessel subjected to the incubation is transferred from the incubation hole into the luminescence detection hole, and the sample detection mechanism performs the luminescence detection.

In one of the embodiments, the incubation block is further provided with a waste liquid discharge hole arranged adjacent to the luminescence detection hole, the reaction vessel is transferred from the luminescence detection hole into the waste liquid discharge hole, and the liquid path device discharges waste liquid from the reaction vessel.

In one of the embodiments, the sample incubation mechanism further comprises a substrate heat-conducting structure, the substrate heat-conducting structure comprising a substrate heat-conducting non-metallic tube and a substrate heat-conducting block, wherein the substrate heat-conducting non-metallic tube and the substrate heat-conducting block are both provided in the incubation block, and the substrate heat-conducting block is configured to heat a substrate in the substrate heat-conducting non-metallic tube.

In one of the embodiments, the sample incubation mechanism further comprises a cleaning liquid heat-conducting container, which is provided in the incubation block for heating the cleaning liquid, and is able to deliver the heated cleaning liquid into the reaction vessel.

In one of the embodiments, the fully automated chemiluminescence immunoassay analyzer further comprises a waste liquid discharge device, wherein the waste liquid discharge device is connected to the liquid path device and used to discharge waste liquid from the reaction vessel after the incubation and luminescence detection device performs the luminescence detection; and The waste liquid discharge device is also able to shield, while discharging the waste liquid, the reaction vessel that is being subjected to the luminescence detection in the incubation and luminescence detection device.

In one of the embodiments, the magnetic separation cleaning device comprises a magnetic separation base, a cleaning liquid injection mechanism, a cleaning liquid discharge mechanism and a magnetic separation attraction mechanism, wherein the magnetic separation base is provided with an access hole, and a cleaning liquid intake hole and a cleaning liquid discharge hole provided in sequence, the access hole being used to receive or remove the reaction vessel to be separated; the magnetic separation base drives the reaction vessel to rotate such that the reaction vessel sequentially corresponds to the cleaning liquid intake hole, the cleaning liquid discharge hole and the access hole; the cleaning liquid injection mechanism is connected to the liquid path device and provided in the cleaning liquid intake hole for adding the cleaning liquid into the reaction vessel; the cleaning liquid discharge mechanism is connected to the liquid path device and arranged in a liftable manner corresponding to the cleaning liquid discharge hole, for discharging the waste cleaning liquid from the reaction vessel; and the magnetic separation attraction mechanism is provided in the magnetic separation base and located on two sides of a rotation path of the reaction vessel.

In one of the embodiments, the magnetic separation cleaning device further comprises a separation cleaning mechanism, and a liquid discharge ascending/descending mechanism mounted in a liftable manner on the magnetic separation base; the cleaning liquid discharge mechanism comprises a cleaning liquid discharge needle provided on the liquid discharge ascending/descending mechanism, the separation cleaning mechanism is provided in the cleaning liquid discharge hole, and when the liquid discharge ascending/descending mechanism drives the liquid discharge needle to descend or ascend, the separation cleaning mechanism cleans an outer wall of the liquid discharge needle.

In one of the embodiments, the cleaning liquid injection mechanism comprises a liquid injection needle and a liquid injection needle seat, wherein the liquid injection needle seat is fixed to the cleaning liquid intake hole; and the liquid injection needle is connected to the liquid path device, is provided on the liquid injection needle seat, and is configured to add the cleaning liquid into the reaction vessel.

In one of the embodiments, the magnet comprises a first magnetic member and a second magnetic member, the first magnetic member and the second magnetic member are distributed along a peripheral side of the magnetic separation base, and the first magnetic member and the second magnetic member are located at two side faces of the rotation path of the reaction vessel;

the magnetic separation base has a first cleaning position between the cleaning liquid intake hole and the cleaning liquid discharge hole, the first magnetic member is arranged corresponding to the first cleaning position, and the second magnetic member is arranged corresponding to the cleaning liquid discharge hole; and in a vertical line direction, an inclined angle between a magnetic pole connection line of the first magnetic member and the vertical line is a first inclined angle, and an inclined angle between a magnetic pole connection line of the second magnetic member and the vertical line direction is a second inclined angle, wherein the first inclined angle is different from the second inclined angle.

In one of the embodiments, the magnetic separation base has a rotation axis, and the magnetic separation base drives the reaction vessel to rotate about the rotation axis; and the extension direction of the rotation axis is parallel to the vertical line, and the magnetic pole connection line of the first magnetic member intersects a straight line where the extension direction of the rotation axis is located.

In one of the embodiments, the magnetic pole connection line of the first magnetic member is perpendicular to the vertical line, and the magnetic pole connection line of the second magnetic member is parallel to the vertical line.

In one of the embodiments, there is also at least one second cleaning position between the first cleaning position and the cleaning liquid discharge hole, and the number of the first cleaning positions is at least two;

the number of the first magnetic members is equal to the number of the first cleaning positions, the number of the second magnetic members is equal to the sum of the number of the second cleaning positions and the number of the cleaning liquid discharge holes, and the second magnetic members respectively correspond to the second cleaning positions and the cleaning liquid discharge holes; and the magnetic properties of adjacent first magnetic members toward one end of the reaction vessel are opposite, and the orientations of magnetic poles of adjacent two of the second magnetic members are opposite.

In one of the embodiments, there are a plurality of cleaning liquid intake holes and cleaning liquid discharge holes, and each of the cleaning liquid intake holes and each of the cleaning liquid discharge holes are alternately placed in a circumferential direction of the magnetic separation base; and the number of groups of the first magnetic member and the second magnetic member is equal to the number of the cleaning liquid intake holes, and each group of the first magnetic member and the second magnetic member correspond to a group of the cleaning liquid intake hole and the cleaning liquid discharge hole.

In one of the embodiments, the magnetic separation cleaning device further comprises a magnetic shielding component, the magnetic shielding component being sleeved outside the magnetic separation base for shielding a magnetic field generated by the magnetic separation attraction mechanism.

In one of the embodiments, the magnetic shielding component may be configured as a cylindrical barrel-shaped or square or polygonal magnetic shielding component made of a magnetic material sleeved outside the magnetic separation base.

In one of the embodiments, the magnetic shielding component may be configured as a magnetic shielding partition provided between the magnetic separation cleaning device and a luminescence detection member.

In one of the embodiments, an upper end face of the shielding cover member may be higher than an upper end face of a magnet, and especially the upper end face of the shielding cover member away from the luminescence detection member is higher than the upper end face of the magnet.

In one of the embodiments, the magnetic separation base is further provided with a substrate injection hole located between the access hole and the cleaning liquid discharge hole, one extended end of the liquid path device extends into the substrate injection hole, and a substrate is added into the reaction vessel.

In one of the embodiments, the liquid path device further comprises a substrate delivery liquid path system, wherein the substrate delivery liquid path system comprises a substrate aspiration pipeline, a substrate discharge pipeline, a substrate power source, and a first substrate control valve, the substrate power source being connected to the substrate aspiration pipeline and the substrate discharge pipeline via the first substrate control valve and used to aspirate a predetermined amount of substrate from a substrate vessel and add the substrate into the reaction vessel.

In one of the embodiments, the substrate delivery liquid path system further comprises a second substrate control valve, the second substrate control valve being provided on the substrate aspiration pipeline for aspirating the substrate from at least two substrate vessels.

In one of the embodiments, the fully automated chemiluminescence immunoassay analyzer further comprises a reaction vessel receiving device provided on the side of the incubation and luminescence detection device away from the magnetic separation cleaning device, for carrying and automatically delivering the reaction vessel.

In one of the embodiments, the reaction vessel receiving device has a drawer structure.

In one of the embodiments, the fully automated chemiluminescence immunoassay analyzer further comprises a waste box provided at a side face of the reaction vessel receiving device for recovering the reaction vessel which is subjected to the detection and from which the waste liquid is discharged.

In one of the embodiments, the fully automated chemiluminescence immunoassay analyzer further comprises a carrying platform, a vessel receiving device and a waste box, wherein the sample and reagent receiving device is located at an edge of one side of the carrying platform; the incubation and luminescence detection device, the magnetic separation cleaning device and the reaction vessel receiving device are located at an edge of the other side of the carrying platform; the mixing device is located between the incubation and luminescence detection device and the sample and reagent receiving device; the liquid path device is located below the carrying platform; the reaction vessel grasping device is located at an edge of the carrying platform and above the reaction vessel carrying device; and the dispensing device is located above the sample and reagent receiving device, and further comprising a main control device and a power supply device, wherein the power supply module is electrically connected to the main control module; the main control module is electrically connected to the sample and reagent receiving device, the dispensing device, the incubation and luminescence detection device, the magnetic separation cleaning device, the reaction vessel grasping device, the reaction vessel receiving device and the liquid path device respectively; and the main control module and the power supply module are located below the carrying platform.

In one of the embodiments, the liquid path device further comprises a magnetic separation cleaning liquid path system, and the magnetic separation cleaning device is provided with a liquid injection needle; the magnetic separation cleaning liquid path system comprises a magnetic separation power source, a magnetic separation liquid aspiration pipeline, a magnetic separation liquid injection pipeline and a first magnetic separation control valve;

the magnetic separation power source is respectively connected to the magnetic separation liquid aspiration pipeline and the magnetic separation liquid injection pipeline via the first magnetic separation control valve; the magnetic separation liquid aspiration pipeline is in communication with a cleaning liquid container with the cleaning liquid, and the magnetic separation liquid injection pipeline is connected to the liquid injection needle;

the first magnetic separation control valve communicates the magnetic separation power source with the magnetic separation liquid aspiration pipeline, disconnects the magnetic separation power source from the magnetic separation liquid injection pipeline, and is able to aspirate the cleaning liquid from the magnetic separation container; and the first magnetic separation control valve communicates the magnetic separation power source with the magnetic separation liquid injection pipeline, disconnects the magnetic separation power source from the magnetic separation liquid aspiration pipeline, and is able to inject the cleaning liquid into the reaction vessel.

In one of the embodiments, the magnetic separation cleaning device is provided with a separation cleaning mechanism and a cleaning liquid discharge needle; the magnetic separation cleaning liquid path system further comprises a first magnetic separation cleaning pipeline, a third magnetic separation control valve and a fourth magnetic separation control valve;

the first magnetic separation cleaning pipeline is connected to the magnetic separation liquid injection pipeline and the separation cleaning mechanism, and the third magnetic separation control valve is provided on the first magnetic separation cleaning pipeline for controlling the opening and closing of the first magnetic separation cleaning pipeline; the fourth magnetic separation control valve is provided on the magnetic separation liquid injection pipeline; and the magnetic separation power source is in communication with the first magnetic separation cleaning pipeline via the magnetic separation liquid injection pipeline, and the fourth magnetic separation control valve closes the magnetic separation liquid injection pipeline to clean an outer wall of the liquid injection needle.

In one of the embodiments, the magnetic separation cleaning device is provided with a cleaning liquid discharge needle; the magnetic separation cleaning liquid path system further comprises a magnetic separation liquid discharge pipeline, a second magnetic separation control valve, a magnetic-magnetic separation drive source, and a recovery pipeline;

the magnetic separation liquid discharge pipeline is connected to the magnetic-magnetic separation drive source and the liquid discharge needle, and the second magnetic separation control valve is provided on the magnetic separation liquid discharge pipeline for discharging waste cleaning liquid from the reaction vessel; and the magnetic-magnetic separation drive source is also connected to the recovery pipeline, and the waste cleaning liquid in the reaction vessel is discharged into a waste liquid bucket through the recovery pipeline.

In one of the embodiments, the magnetic separation cleaning liquid path system further comprises a second magnetic separation cleaning pipeline and a fifth magnetic separation control valve; the second magnetic separation cleaning pipeline is connected to the separation cleaning mechanism and the magnetic-magnetic separation drive source, the fifth magnetic separation control valve is provided on the second magnetic separation cleaning pipeline for controlling the opening and closing of the second magnetic separation cleaning pipeline, and the waste cleaning liquid is discharged into the waste liquid bucket by the magnetic-magnetic separation drive source.

In one of the embodiments, the magnetic-magnetic separation drive source comprises a negative pressure chamber, a vacuum pump, and a negative pressure sensor, wherein the negative pressure chamber is connected to the magnetic separation liquid discharge pipeline and the recovery pipeline, the vacuum pump is provided on the recovery pipeline, the negative pressure sensor is configured to detect the pressure of the negative pressure chamber, and the pressure is adjusted by the vacuum pump.

In one of the embodiments, the magnetic-magnetic separation drive source further comprises a sixth magnetic separation control valve, wherein the sixth magnetic separation control valve is provided on the recovery pipeline, and the sixth magnetic separation control valve is also connected to the second magnetic separation cleaning pipeline and the negative pressure chamber for respectively communicating the recovery pipeline with the negative pressure chamber and the second magnetic separation cleaning pipeline.

In one of the embodiments, the magnetic separation cleaning device comprises cleaning liquid injection mechanisms and cleaning liquid discharge mechanisms; and the number of the cleaning liquid injection mechanisms and the number of the cleaning liquid discharge mechanisms are both at least two, and the number of the magnetic separation liquid injection pipelines, the number of the magnetic separation liquid discharge pipelines, the number of the first magnetic separation cleaning pipelines, the number of the second magnetic separation cleaning pipelines, the number of the second magnetic separation control valves, the number of the third magnetic separation control valves, the number of the fourth magnetic separation control valves and the number of the fifth magnetic separation control valves are consistent with the number of the cleaning liquid injection mechanisms.

In one of the embodiments, the magnetic separation cleaning liquid path system further comprises a seventh magnetic separation control valve for aspirating the cleaning liquid from at least two cleaning liquid containers; the liquid path device further comprises a dispensing liquid path system further comprising a fourth dispensing control valve, the fourth dispensing control valve being provided on the second dispensing cleaning pipeline for aspirating the cleaning liquid from at least two cleaning liquid containers.

In one of the embodiments, the sample and reagent receiving device is provided with a reagent housing, the bottom of the reagent housing being provided with a water discharge channel; and the liquid path device further comprises a condensed water discharge pipeline connected to the fifth magnetic separation control valve and the water discharge channel, wherein the fifth magnetic separation control valve disconnects the second magnetic separation cleaning pipeline from the magnetic-magnetic separation drive source, and communicates the water discharge channel with the magnetic-magnetic separation drive source, for discharging condensed water from the reagent housing.

In one of the embodiments, the fully automated chemiluminescence immunoassay analyzer further comprises a waste liquid discharge device, wherein the liquid path device further comprises an incubation waste liquid discharge pipeline and an incubation waste liquid control valve, the incubation waste liquid discharge pipeline is connected to the waste liquid discharge device and the magnetic-magnetic separation drive source, and the incubation waste liquid control valve is provided on the incubation waste liquid discharge pipeline for controlling the opening and closing of the incubation waste liquid discharge pipeline, to discharge the waste liquid from the reaction vessel subjected to the detection into the waste liquid bucket.

With the use of the above technical solutions, the present disclosure has the beneficial effects as follows:

when the fully automated chemiluminescence immunoassay analyzer of the present disclosure detects a sample, the dispensing needle respectively aspirates the sample and the reagent in the sample and reagent receiving device and respectively transfers same to the reaction vessel of the mixing seat; after performing mixing, the reaction vessel grasping device then transfers the reaction vessel to the incubation and luminescence detection device to perform an incubation operation; after the incubation is completed, the magnetic separation cleaning device performs separating and cleaning on the reaction vessel; after the cleaning is completed, the incubation and luminescence detection device performs luminescence detection on the reaction vessel to obtain various parameters of the sample; the incubation and luminescence detection device of the fully automated chemiluminescence immunoassay analyzer of the present disclosure integrates the sample receiving and the reagent storage, and integrates the incubation and the luminescence detection; each component performs the above steps according to its arrangement, which can effectively solve the problems of complex structures, large footprints, and high costs of the current chemiluminescence immunoassay analyzers, so that the fully automated chemiluminescence immunoassay analyzer of the present disclosure has a simple structure and is convenient to operate, and can also reduce the overall size such that the footprint thereof is small and the production cost is reduced, so that the fully automated chemiluminescence immunoassay analyzer is easy to achieve miniaturization, and is convenient for an operator to use.

BRIEF DESCRIPTION OF THE DRAWINGS

FIG. 7 is a cross-sectional view of a reagent receiving mechanism in the sample and reagent receiving device shown in FIG. 3;

FIG. 8 is a structural schematic view of a condensation structure in the sample and reagent receiving device shown in FIG. 3;

FIG. 9 is a schematic view of a dispensing device in the fully automated chemiluminescence immunoassay analyzer shown in FIG. 1;

FIG. 10 is a schematic view of a mixing device in the fully automated chemiluminescence immunoassay analyzer shown in FIG. 1;

Figure 1:
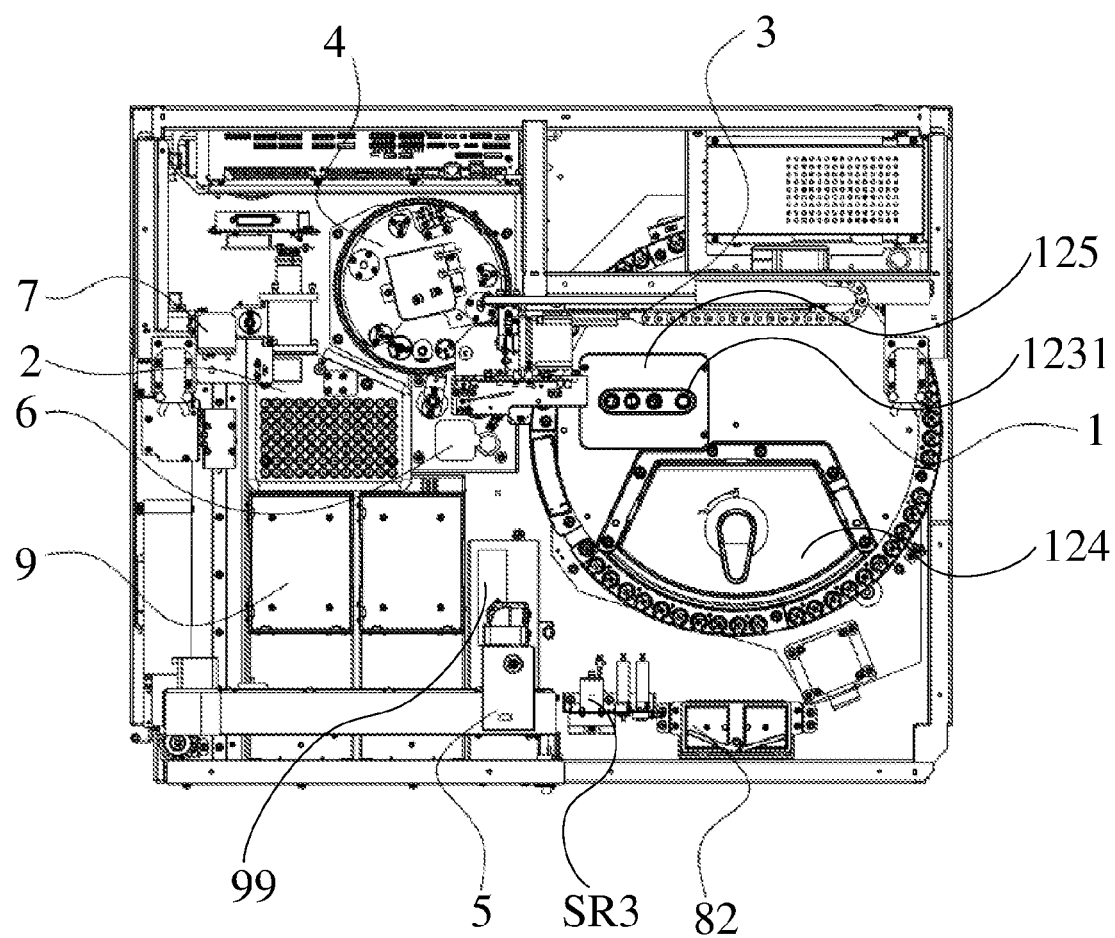
FIG. 1 is a top structural schematic view of a fully automated chemiluminescence immunoassay analyzer according to an embodiment of the present disclosure.

In the figures:
1—Sample and reagent receiving device;
11—Sample receiving mechanism; 111—Sample holder; 1111—Scanning notch; 112—Chassis; 113—Sample receiving driving structure; 114—Needle cleaning structure;
12—Reagent receiving mechanism; 121—Reagent housing; 1211—Scanning window; 1212—Water discharge channel; 1213—Transparent window; 122—Reagent disc; 123—Reagent housing lid; 1231—Reagent aspiration hole; 12311—First reagent aspiration hole; 12312—Second reagent aspiration hole; 124—Switching cover; 125—Condensation structure; 1251—Condensation plate; 1252—Water receiving tray; 1253—First annular cylinder wall; 1254—Second annular cylinder wall; 126—Reagent disc driving structure; 127—Cooling structure; 128—Hot-end radiator; 1281—Heat-conducting component; 1282—Hot-end heat dissipation fin; 1283—Hot-end fan;
13—Identification code scanner;
2—Incubation and luminescence detection device;
21—Sample incubation mechanism; 211—Incubation block; 2111—Incubation hole; 2112—Luminescence detection hole; 2113—Waste liquid discharge hole; 212—Substrate heat-conducting structure; 213—Washing liquid preheating container;
22—Luminescence detection member;
3—Dispensing device;
31—Dispensing needle;
32—Vertical movement mechanism;
33—Horizontal movement mechanism;
34—Dispensing needle swab;
35—Second cleaning mechanism;
4—Magnetic separation cleaning device;
41—Magnetic separation base; 411—Access hole; 412—Cleaning liquid intake hole; 413—Cleaning liquid discharge hole; 414—First cleaning position; 415—Second cleaning position;
42—Cleaning liquid injection mechanism;
43—Cleaning fluid discharge mechanism;
44—Magnetic separation swab;
45—Liquid discharge ascending/descending portion;
46—Substrate injection hole;
47—Magnetic shielding component; 471—Upper end face of the magnetic shielding component;
48—Magnetic separation attraction mechanism; 481—First magnetic member; 482—Second magnetic member; 483—Upper end face of the magnetic separation attraction mechanism;
5—Reaction vessel grasping device;
6—Mixing device;
61—Mixing drive mechanism;
62—Reagent and sample mixing seat;
63—Substrate mixing seat;
64—Mixing mechanism;
7—Waste liquid discharge device;
8—Liquid path device;
81—Dispensing liquid path system; 811—Dispensing aspiration/discharge pipeline; 812—First dispensing cleaning pipeline; 813—Second dispensing cleaning pipeline; 814—First dispensing liquid discharge pipeline; 815—Second dispensing liquid discharge pipeline; SR1—First dispensing syringe; SR55—Second vacuum pump; V811—First dispensing control valve; V812—Second dispensing control valve; V813—Third dispensing control valve; V814—Fourth dispensing control valve; SR6—Second dispensing syringe;
82—Substrate delivery liquid path system; 821—Substrate aspiration pipeline; 822—Substrate discharge pipeline; SR3—Substrate fixed-displacement pump; V821—First substrate control valve; V822—Second substrate control valve;
83—Magnetic separation cleaning liquid path system; 831—Magnetic separation liquid aspiration pipeline; 832—Magnetic separation liquid injection pipeline; 833—Magnetic separation liquid discharge pipeline; 834—First magnetic separation cleaning pipeline; 835—Recovery pipeline; 836—Second magnetic separation cleaning pipeline; SR4—Magnetic separation syringe; SR5—Magnetic-magnetic separation drive source; SR51—Vacuum chamber; SR52—Negative pressure sensor; SR53—First vacuum pump; V831—First magnetic separation control valve; V832—Second magnetic separation control valve; V833—Third magnetic separation control valve; V834—Fourth magnetic separation control valve; V835—Fifth magnetic separation control valve; V836—Sixth magnetic separation control valve; V837—Seventh magnetic separation control valve;
9—Reaction vessel receiving device;
10—Power supply device;

77—Main control device;
88—Cleaning liquid detection component;
99—Waste box.

DETAILED DESCRIPTION

In order to make the objects, technical solutions, and advantages of the present disclosure more apparent, a fully automated chemiluminescence immunoassay analyzer of the present disclosure will be further described below in detail through embodiments in conjunction with the accompanying drawings. It should be understood that the particular embodiments described herein are merely intended to explain the present disclosure and is not intended to define the present disclosure.

The serial numbers themselves for the components herein, for example, "first", "second", etc., are merely used to distinguish the described objects, and do not have any sequential or technical meaning. Moreover, as used in the present application, "connection" or "coupling", unless otherwise specified, includes both direct and indirect connections (couplings). In the description of the present disclosure, it should be understood that the orientation or position relationship indicated by the terms "upper", "lower", "front", "rear", "left", "right", "vertical" "horizontal", "top", "bottom", "inner", "outer", "clockwise", "counterclockwise" etc. are based on the orientation or position relationship shown in the accompanying drawings and are intended to facilitate the description of the present disclosure and simplify the description only, rather than indicating or implying that the device or element referred to must have a particular orientation or be constructed and operated in a particular orientation, and therefore will not to be interpreted as limiting the present disclosure.

In the present disclosure, unless otherwise explicitly specified and defined, the expression a first feature being "on" or "under" a second feature may be the case that the first feature is in direct contact with the second feature, or the first feature is in indirect contact with the second feature via an intermediate medium. Furthermore, the expression the first feature being "over", "above" and "on top of" the second feature may be the case that the first feature is directly above or obliquely above the second feature, or only means that the level of the first feature is higher than the second feature. The expression the first feature being "underneath", "below" and "beneath" the second feature may be the case that the first feature is directly below or obliquely below the second feature, or only means that the level of the first feature is less than the second feature.

Referring to FIG. 1, the present disclosure provides a fully automated chemiluminescence immunoassay analyzer. The fully automated chemiluminescence immunoassay analyzer is configured to analyze and detect a sample to be detected, so as to obtain the corresponding detection result to meet the requirements of use. It should be noted that the specific type of the sample to be detected is not limited. In some embodiments, the sample to be detected includes a solid sample or a liquid sample. It can be understood that when a liquid sample is detected, the liquid sample needs to be carried by a vessel such as a test tube and placed on a sample holder. Further, liquid samples include, but are not limited to, blood samples. When the fully automated chemiluminescence immunoassay analyzer of the present disclosure is configured to detect blood samples, the blood samples are loaded into test tubes and are sequentially placed on a test tube rack. The fully automated chemiluminescence immunoassay analyzer of the present disclosure has a simple structure and is convenient to operate, and can also reduce the overall size such that the footprint thereof is small and the production cost is reduced, so that the fully automated chemiluminescence immunoassay analyzer is easy to achieve miniaturization, and is convenient for an operator to use.

In the present disclosure, the fully automated chemiluminescence immunoassay analyzer comprises a sample and reagent receiving device 1, a dispensing device 3, a mixing seat, an incubation and luminescence detection device 2, a reaction vessel grasping device 5, and a magnetic separation cleaning device 4. The sample and reagent receiving device 1 is configured to load samples and reagents. Particularly, the sample and reagent receiving device 1 can store a variety of samples. It can be understood that the samples in the sample and reagent receiving device 1 may be manually added by an operator, or may be automatically added by using an automatic sample feeding device. The sample and reagent receiving device 1 can also load various reagents required for sample detection, so as to facilitate the selection of the desired reagent, and to improve the efficiency of aspirating the reagent. The dispensing device 3 comprises a dispensing needle 31. The dispensing needle 31 is used to aspirate and discharge the sample and the reagent, so as to transfer the sample or the reagent into the reaction vessel. The mixing seat is configured to support the reaction vessel. It can be understood that the empty reaction vessel is transferred to the mixing seat, the dispensing device 3 respectively transfers the sample and the reagent into the reaction vessel, and after the sample and the reagent are mixed uniformly via the mixing seat, the reaction vessel is transferred into the incubation and luminescence detection device 2. The incubation and luminescence detection device 2 is used for incubation and luminescence detection, and the magnetic separation cleaning device 4 is used for separation cleaning. After the reaction vessel is transferred to the incubation and luminescence detection device 2, the incubation and luminescence detection device 2 can incubate the sample and the reagent in the reaction vessel. The reaction vessel subjected to the incubation is transferred to the magnetic separation cleaning device 4 to perform separation cleaning. The reaction vessel subjected to the cleaning is then transferred back into the incubation and luminescence detection device 2 to perform luminescence detection to obtain the corresponding parameters of the sample. The reaction vessel grasping device 5 is configured to transfer the reaction vessel. Particularly, the reaction vessel grasping device 5 transfers the reaction vessel between the mixing seat, the incubation and luminescence detection device 2 and the magnetic separation cleaning device 4.

In order to facilitate the understanding of the names of various stages of the sample and the reagent, the names of various stages of the sample and the reagent are described in detail here: the sample and the reagent in the reaction vessel are called a mixture after being mixed, and the incubation and luminescence detection device 2 can perform an incubation operation on the mixture such that the sample fully reacts with the reagents, and at this time, the substances in the reaction vessel are an analyte and impurities. The mixture refers to the substances formed after the sample and the reagent are mixed, regardless of the ratio of the sample to the reagent and the concentrations thereof, which are referred to herein as a mixture. The mixture subjected to the incubation is presented in the form of an analyte and impurities in the reaction vessel. The impurities may be inadequately reacted substances, or side reaction products generated by the occurrence of side reactions, or other substances that affect the detection of the incubation and luminescence detection device 2, etc., or a combination of at least two of the above. The magnetic separation cleaning device 4 cleans the analyte and the impurities in the reaction vessel to remove the impurities from the reaction vessel, such that only the analyte exists in the reaction vessel. The incubation and luminescence detection device 2 can detect the analyte in the reaction vessel to obtain various parameters of the sample. If a substrate is added into the reaction vessel subjected to the separation cleaning, that is, the substrate is mixed with the analyte, the substrate and the analyte are still called the analyte after being mixed because the substrate does not change the attributes of the analyte, and only the luminescence value of the analyte is increased. Moreover, the present disclosure uses a cleaning liquid to clean the analyte and the impurities in the dispensing needle 31 and the reaction vessel, and the cleaning liquid after performing the cleaning is referred to as waste cleaning liquid.

The magnetic separation cleaning device 4 and the incubation and luminescence detection device 2 are located on the same side of the sample and reagent receiving device 1, and the magnetic separation cleaning device 4 is arranged adjacent to the incubation and luminescence detection device 2. The mixing seat is located between the sample and reagent receiving device 1 and the incubation and luminescence detection device 2. The reaction vessel grasping device 5 transfers the reaction vessel to the mixing seat, and the dispensing needle 31 of the dispensing device 3 is located above the sample and reagent receiving device 1, and can respectively transfer the sample and the reagent into the reaction vessel on the mixing seat. The fact that the mixing seat is located between the sample and reagent receiving device 1 and the incubation and luminescence detection device 2 can reduce the movement path of the dispensing device 3, thereby shortening the distance by which the sample and the reagent is transferred by the dispensing device 3, so as to reduce the transfer time of the sample and the reagent and improve the processing speed of the fully automated chemiluminescence immunoassay analyzer. Moreover, the fact that the magnetic separation cleaning device 4 is arranged adjacent to the incubation and luminescence detection device 2 can shorten the transfer path of the reaction vessel between the magnetic separation cleaning device 4 and the incubation and luminescence detection device 2, improve the processing efficiency, and thus improve the processing speed of the fully automated chemiluminescence immunoassay analyzer.

The sample and reagent receiving device 1 is provided with a sample aspiration station and a reagent aspiration station, and the dispensing device 3 aspirates the sample from the sample and reagent receiving device 1 at the sample aspiration station and then transfers the sample into the reaction vessel on the mixing seat, and the dispensing device 3 further aspirates the reagent from the sample and reagent receiving device 1 at the reagent aspiration station and then transfers the reagent into the reaction vessel on the mixing seat. It can be understood that, in principle, there is no sequence requirement for the transfer of the sample and the reagent, that is, the sample may be transferred first and then the reagent is transferred, or the reagent may be transferred first and then the sample is transferred.

After the reaction vessel grasping device 5 transfers the reaction vessel to the mixing seat, and the sample and the reagent are added, the reaction vessel grasping device 5 transfers the reaction vessel with the added sample and reagent from the mixing seat to the incubation and luminescence detection device 2 to perform incubation, and the reaction vessel grasping device 5 further transfers the reaction vessel 4 subjected to the incubation to the magnetic separation cleaning device to perform separation cleaning, and transfers the reaction vessel subjected to the separation cleaning into the incubation and luminescence detection device 2 to perform luminescence detection. The sample and the reagent in the reaction vessel form a mixture on the mixing seat, the reaction vessel grasping device 5 then transfers the reaction vessel from the mixing seat to the incubation and luminescence detection device 2, and the incubation and luminescence detection device 2 incubates the mixture in the reaction vessel, such that the mixture forms an analyte and impurities in the reaction vessel. The reaction vessel grasping device 5 then transfers the reaction vessel from the incubation and luminescence detection device 2 into the magnetic separation cleaning device 4, and the impurities are cleaned and removed from the reaction vessel by the magnetic separation cleaning device 4, leaving the analyte. The reaction vessel grasping device 5 then transfers the cleaned reaction vessel to the incubation and luminescence detection device 2, and the analyte in the reaction vessel is detected by the incubation and luminescence detection device 2 to obtain various parameters of the sample.

Moreover, the sample and reagent receiving device 1 can both load the sample and store the reagent, such that a sample receiving module and a reagent storage module can be integrated together, reducing the space occupied by the sample receiving module and the reagent storage module when they are separately provided, so that the volume of the sample and reagent receiving device 1 is small. The incubation and luminescence detection device 2 integrates an incubation function module and a detection function module together to reduce the space occupied by the incubation function module and the detection function module when they are separately provided. In this way, after the components of the fully automated chemiluminescence immunoassay analyzer have adopted the above layout arrangement and functional integration, the overall layout can be reasonable and compact, the volume thereof can be small, and it is also possible to facilitate a user in operating, using and maintaining.

The fully automated chemiluminescence immunoassay analyzer of the present disclosure is configured to detect the luminescence value of the analyte to obtain various parameters of the sample. To increase the luminescence value of the analyte during detection, the fully automated chemiluminescence immunoassay analyzer of the present disclosure adds a substrate to the reaction vessel subjected to the separation cleaning, and the substrate is attached to the analyte, and can increase the luminescence value of the analyte, to ensure the detection accuracy of the sample. Particularly, the fully automated chemiluminescence immunoassay analyzer is provided with a substrate vessel for holding the substrate, and the substrate is added to the reaction vessel through a liquid path device 8 via the magnetic separation cleaning device 4. This can reduce the provision of a structure for carrying the reaction vessel when adding the substrate, reduce the number of transfers of the reaction vessel, and thus reduce the overall volume. The substrate is added to the reaction vessel after being subjected to the magnetic separation cleaning, such that the substrate and the analyte are mixed, the reaction vessel is then transferred from the magnetic separation cleaning device 4 into the incubation and luminescence detection device 2, and is subjected to the incubation before the incubation and luminescence detection device 2 performs a luminescence detection on the analyte, so as to obtain various parameters of the sample.

Referring to FIGS. 1, and 17 to 19, as an implementable way, the fully automated chemiluminescence immunoassay analyzer further comprises a carrying platform. The sample and reagent receiving device 1 is located on the right side of the carrying platform. The incubation and luminescence detection device 2, and the magnetic separation cleaning device 4 are located side by side on the left rear side of the carrying platform. The reaction vessel grasping device 5 is located on the front side of the carrying platform. The carrying platform has a supporting function, and is supported by the mixing seat to provide a placement space for each structure of the fully automated chemiluminescence immunoassay analyzer. Particularly, the sample and reagent receiving device 1, the mixing seat, the incubation and luminescence detection device 2, the magnetic separation cleaning device 4, etc. are all provided on the carrying platform, and the liquid path device 8 of the fully automated chemiluminescence immunoassay analyzer is located below the carrying platform. Moreover, various liquid storage vessels, waste liquid vessels, etc. connected to the liquid path device 8 are all provided below the carrying platform. In this way, the space can be fully utilized, and the overall volume of the fully automated chemiluminescence detector is small.

It can be understood that the side on which the user operates the fully automated chemiluminescence immunoassay analyzer is defined as the front side of the carrying platform, and correspondingly, the side opposite the front side of the carrying platform is the rear side of the carrying platform, and two sides adjacent to the front side of the carrying platform are the left and right sides of the carrying platform. Particularly, as shown in FIG. 1, the carrying platform has left, right, front, and rear sides. The right side of the carrying platform is a sample and reagent management area, the left side thereof is a reaction vessel dispatching, reaction, and detection area, and the rear side thereof is an auxiliary support area. The substrate vessel is placed at the forefront of the sample and reagent management area on the right side, and the sample and reagent receiving device 1 is provided in the sample and reagent management area on the right side, and is located on the rear side of the substrate vessel. The dispensing device 3 is located above the sample and reagent receiving device 1, and the mixing seat is located on the left side of the sample and reagent receiving device 1. This can shorten the transfer path of the sample and the reagent, increase the transfer efficiency, and also reduce the footprint, thereby reducing the overall volume. The left side of the carrying platform is the reaction vessel dispatching, reaction and detection area, which will be described in detail later. The reaction vessel grasping device 5 is located on the left front side of the carrying platform, and the movement area of the reaction vessel grasping device 5 can cover the incubation and luminescence detection device 2, the magnetic separation cleaning device 4, the mixing seat, etc. in the reaction vessel dispatching, reaction and detection area, to achieve the transfer of the reaction vessel. The incubation and luminescence detection device 2 is arranged adjacent to the mixing seat. The magnetic separation cleaning device 4 and the incubation and luminescence detection device 2 are arranged side by side in the left area of the carrying platform. A gas/liquid path and circuit system supporting the operation of the whole machine are arranged at the rear and bottom of the carrying platform. The purpose of this arrangement is to place the components that may need maintenance as far as possible to the periphery of the whole machine, reducing the complexity of maintenance that may occur at a client.

Further, the magnetic separation cleaning device 4 is located between the sample and reagent receiving device 1 and the incubation and luminescence detection device 2, and the mixing seat is located between the magnetic separation cleaning device 4 and the reaction vessel grasping device 5. In this embodiment, the incubation and luminescence detection device 2 is arranged in an L shape, the magnetic separation cleaning device 4 is located at a notch of the L-shaped incubation and luminescence detection device 2, and the mixing seat is located in a space enclosed by the magnetic separation cleaning device 4, the incubation and luminescence detection device 2, and the sample and reagent receiving device 1, so that the footprint and the overall volume can be reduced while reducing the transfer path of the reaction vessel and the transfer path of the dispensing needle 31.

After adopting the above layout, the fully automated chemiluminescence immunoassay analyzer of the present disclosure can shorten the transfer path of the sample and the reagent, shorten the transfer path of the reaction vessel, make the overall structure compact, improve the processing efficiency of the sample, and thus improve the operation speed of the whole machine. Moreover, for the fully automated chemiluminescence immunoassay analyzer of the present disclosure, the layout of the whole machine is reasonable and compact and the volume thereof is small through the ingenious layout and functional integration between modules while facilitating the user in operating, using and maintaining, without reducing the number of sample vessels, reagent vessels and reaction vessels.

Referring to FIGS. 1, 14, and 16 to 19, further, the fully automated chemiluminescence immunoassay analyzer of the present disclosure also comprises a liquid path device 8. The liquid path device 8 can realize the input and output of a fluid required in the fully automated chemiluminescence immunoassay analyzer. The liquid path device 8 is respectively connected to the dispensing device 3 and the magnetic separation cleaning device 4. The liquid path device 8 is configured to control the dispensing device 3 to aspirate and discharge the sample or the reagent and to clean the dispensing device 3. The liquid path device 8 is further used to inject or discharge a cleaning liquid into or from the magnetic separation cleaning device 4. Particularly, the liquid path device 8 can control the dispensing device 3 to aspirate the sample from the sample and reagent receiving device 1, and then control the dispensing device 3 to transfer the aspirated sample into the reaction vessel. The liquid path device 8 can control the dispensing device 3 to aspirate the reagent from the sample and reagent receiving device 1, and then control the dispensing device 3 to transfer the aspirated reagent into the reaction vessel. Since after each time the sample and the reagent are aspirated, there are residues left on the dispensing device 3, and there will be a problem of contaminating the sample and the reagent, the liquid path device 8 can also deliver the cleaning liquid to clean the dispensing device 3, and after performing the cleaning, the waste liquid is discharged. The liquid path device 8 can also control the magnetic separation cleaning device 4 to inject the cleaning liquid into the reaction vessel. After the separation cleaning, the liquid path device 8 can also control the magnetic separation cleaning device 4 to discharge the cleaning liquid from the reaction vessel. In addition, the liquid path device 8 is also connected to the incubation and luminescence detection device 2 for discharging the waste liquid from the incubation and luminescence detection device 2 after the testing. That is to say, the waste liquid in the reaction vessel subjected to the detection is first discharged, and then the discarded empty reaction vessel is discarded by the reaction vessel grasping device 5, such that the pollution caused by the turbulent flow of the waste liquid can be avoided. Of course, in other implementations of the present disclosure, the reaction vessel grasping device 5 may also be used to directly discard the reaction vessel subjected to the detection and having the waste liquid. It can be understood that the connection between certain components of the liquid path device 8 refers to connection via a pipeline, which is not described in detail here.

Referring to FIG. 1, optionally, the fully automated chemiluminescence immunoassay analyzer further comprises two reaction vessel receiving devices 9. The reaction vessel receiving devices 9 are arranged side by side on the left front side of the carrying platform, and are located below the reaction vessel grasping device 5. The reaction vessel grasping device 5 transfers the reaction vessel from the reaction vessel receiving device 9 to the mixing seat. Particularly, the reaction vessel receiving devices 9 are located in the reaction vessel dispatching, reaction and reaction detection area, and are located on the side of the incubation and luminescence detection device 2 away from the magnetic separation cleaning device 4, for carrying and automatically delivering the reaction vessel to improve the delivery efficiency. Of course, in other implementations of the present disclosure, the reaction vessel receiving devices 9 may also be replaced, that is, the reaction vessel receiving devices 9 are not used to deliver the reaction vessel, and the reaction vessel may be directly placed in the incubation and luminescence detection device 2. Preferably, the reaction vessel delivered by the reaction vessel receiving device 9 is usually a disposable consumable. Of course, the reaction vessel may also be recovered for reuse. Optionally, when the reaction vessel can be reused, it is also possible to not use the reaction vessel receiving device 9 to deliver the reaction vessel. Moreover, the reaction vessel refers to a consumable that carries and can perform sample reaction, detection, and analysis, such as a reaction cup, a test tube, a sample slide, a sample tube, etc. In this embodiment, the reaction vessel refers to a reaction cup, and the reaction vessel receiving device 9 generally conveys a reaction vessel box, and the reaction vessel box is internally provided with reaction cups distributed in a matrix.

The reaction vessel receiving device 9 has a drawer structure, that is, the reaction vessel receiving device 9 can be drawn out of or pushed into the fully automated chemiluminescence immunoassay analyzer. Particularly, after various components on the fully automated chemiluminescence immunoassay analyzer are covered by an outer cover, the reaction vessel receiving device 9 is drawn out or pushed in from below the front side of the carrying platform. When the reaction vessel receiving device 9 is drawn out, the reaction vessel box filled with reaction vessels can be loaded into the reaction vessel receiving device 9; and after the receiving of the reaction vessel box is completed, the reaction vessel receiving device 9 is pushed in, such that the reaction vessel receiving device 9 can automatically convey the reaction vessels. The reaction vessel receiving device 9 lifts the reaction vessel box such that the reaction vessel box is located on the top of the reaction vessel receiving device 9, and at this time, an empty reaction vessel in the reaction vessel box can be grasped and transferred to the mixing seat. It can be understood that the reaction vessel box in the reaction vessel receiving device 9 can be placed on a support plate in a stacking manner, and the support plate is driven by a drive motor to ascend and descend to realize the lifting of the reaction vessel box and facilitate the grasping of a reaction vessel. The drive motor realizes the ascending and descending movements by means of a synchronous belt structure, a chain transmission structure, or other structures.

Moreover, the two reaction vessel receiving devices 9 can be used alternately. After all the reaction vessels in one of the reaction vessel receiving devices 9 are grasped, the reaction vessel receiving device 9 needs to be pulled out to load a reaction vessel box filled with reaction vessels, at this time, the other reaction vessel receiving device 9 can continue to deliver a reaction vessel to the fully automated chemiluminescence immunoassay analyzer to avoid affecting the operation of the fully automated chemiluminescence immunoassay analyzer due to the non-loaded reaction vessel receiving device 9, so that the fully automated chemiluminescence immunoassay analyzer can continuously perform sample detections, improving the efficiency.

Optionally, the bottom of the reaction vessel receiving device 9 is provided with a detection sensor for detecting whether the reaction vessel receiving device 9 is installed in place. The reaction vessel can be automatically conveyed only after the reaction vessel receiving device 9 is pushed into place, so that the fully automated chemiluminescence immunoassay analyzer can operate normally. If the reaction vessel receiving device 9 is not in place, the reaction vessel will not be conveyed, to ensure the safety of the operation of the fully automated chemiluminescence immunoassay analyzer. Therefore, the detection sensor detects whether the reaction vessel receiving device 9 is in place when being pushed in, and after being pushed into place, the detection sensor can send out an in-place signal, such that the reaction vessel receiving device 9 operates normally. Still optionally, the reaction vessel receiving device 9 is further provided with a fixing attraction component for fixing the reaction vessel receiving device 9. After the reaction vessel receiving device 9 is installed in place, the fixing attraction component can fix the reaction vessel receiving device 9 on the fully automated chemiluminescence immunoassay analyzer, so that after the user pushes the reaction vessel receiving device 9 in, the reaction vessel receiving device 9 can be reliably and stably fixed by the fixing attraction component to prevent playing. As an example, the fixing attraction component may be a magnet.

Still optionally, the fully automated chemiluminescence immunoassay analyzer of the present disclosure uses a disposable reaction vessel for sample detection. After the luminescence detection is completed, the used reaction vessel needs to be recovered. Therefore, the fully automated chemiluminescence immunoassay analyzer of the present disclosure further comprises a waste box 99 having an opening in an upper portion thereof. The waste box 99 is provided on the right side of the reaction vessel receiving device 9 and located below the reaction vessel grasping device 9. The reaction vessel grasping device 9 puts the reaction vessel, from which the waste liquid is expelled, into the waste box 99 through the opening. After the reaction vessel receiving device is drawn out, the waste box 99 may also be drawn out from the front side of the carrying platform, which is convenient for emptying the waste box 99. After the luminescence detection of the reaction vessel is completed, the waste liquid in the reaction vessel is discharged, and the empty used reaction vessel is then transferred into the waste box 99, such that the waste box 99 can continuously recover the used reaction vessel, to prevent the used reaction vessel from occupying the incubation and luminescence detection device 2, and the used reaction vessel can also be prevented from being discarded indiscriminately. After the waste box 99 is filled with the reaction vessels or the reaction vessels in the waste box 99 need to be emptied, the waste box 99 can be removed from the fully automated chemiluminescence immunoassay analyzer, and after being emptied, the waste box 99 is then installed on the fully automated chemiluminescence immunoassay analyzer.

Optionally, the waste box 99 is provided with a determination sensor for detecting whether the waste box 99 is loaded in place. The emptied waste box 99 needs to be loaded into the fully automated chemiluminescence immunoassay analyzer again. If the waste box 99 is not loaded in place, the recovery of the used reaction vessel will be affected, and the waste box 99 will also have the risk of contact with other structures of the fully automated chemiluminescence immunoassay analyzer, affecting the operation of the fully automated chemiluminescence immunoassay analyzer. After the determination sensor is provided, the determination sensor can detect whether the waste box 99 is in place, and if not, the determination sensor sends out an alarm, or if yes, the determination sensor sends out an in-place signal, such that the fully automated chemiluminescence immunoassay analyzer operates normally. Still optionally, the waste box 99 is further provided with a feedback button. After the waste box 99 is emptied and reloaded, and the feedback button is pressed to clear the count of the waste box 99. In this way, after emptying the waste box 99, the user clear the count of the waste box 99 via the feedback button. When the fully automated chemiluminescence immunoassay analyzer discards the reaction vessel to the waste box 99 again, the waste box can be recounted, which facilitates the fully automated chemiluminescence immunoassay analyzer in monitoring the number of the reaction vessels in the waste box 99, to ensure the normal operation of the fully automated chemiluminescence immunoassay analyzer.

The fully automated chemiluminescence immunoassay analyzer of the present disclosure transfers the reaction vessel between the reaction vessel receiving device 9, the mixing seat, the incubation and luminescence detection device 2, the magnetic separation cleaning device 4, and the waste box 99 via the reaction vessel grasping device 5. Particularly, the reaction vessel grasping device 5 is provided with a vertical movement mechanism, a horizontal transverse movement mechanism, and a horizontal longitudinal movement mechanism. The reaction vessel grasping device 5 realizes the movement to any position in the three-dimensional space via the vertical movement mechanism, the horizontal transverse movement mechanism, and the horizontal longitudinal movement mechanism, and realizes the grasping and releasing of the reaction vessel at any position in the three-dimensional space, thereby realizing the transfer of the reaction vessel. Moreover, the reaction vessel grasping device 5 is further provided with a cup grasper, the horizontal transverse movement mechanism is provided on the vertical movement mechanism, the horizontal longitudinal movement mechanism is provided on the horizontal transverse movement mechanism, and the cup grasper is provided on the horizontal longitudinal movement mechanism. The vertical movement mechanism, the horizontal transverse movement mechanism, and the horizontal longitudinal movement mechanism respectively move and can drive the cup grasper to move, such that the cup grasper can move to any position to perform the grasping and releasing operations on the reaction vessel. As an example, the vertical movement mechanism, the horizontal transverse movement mechanism and the horizontal longitudinal movement mechanism each comprise a transfer drive motor and a synchronous belt structure to realize the movement in the corresponding direction. Of course, the synchronous belt structure may also be replaced by a rack and pinion structure, a chain transmission structure, or other structures capable of achieving linear motion.

After the reaction vessel grasping device 5 grasps the reaction vessel in the reaction vessel receiving device 9, and transfers the reaction vessel to the mixing seat, the dispensing needle 31 aspirates the sampleat the sample aspiration station of the sample and reagent receiving device 1 and then transfers the sample into the reaction vessel on the mixing seat, and the dispensing needle 31 aspirates the reagent at the reagent aspiration station of the sample and reagent receiving device 1 and then transfers the reagent into the reaction vessel on the mixing seat, such that the mixing seat uniformly mixes the sample and the reagent in the reaction vessel to form a mixture. The reaction vessel grasping device 5 then transfers the reaction vessel with the mixture from the mixing seat into the incubation and luminescence detection device 2, and after the incubation and luminescence detection device 2 incubates the mixture in the reaction vessel, the mixture in the reaction vessel forms an analyte and impurities. Thereafter, the reaction vessel grasping device 5 then transfers the reaction vessel with the analyte and the impurities from the incubation and luminescence detection device 2 into the magnetic separation cleaning device 4, and the impurities are cleaned and removed from the reaction vessel by the magnetic separation cleaning device 4. The reaction vessel can be added with the substrate at the magnetic separation cleaning device 4. After the addition is completed, the reaction vessel grasping device 5 transfers the reaction vessel from the magnetic separation cleaning device 4 into the incubation and luminescence detection device 2 to perform incubation. The reaction vessel subjected to the incubation is then subjected to luminescence detection. After the detection is completed, the waste liquid in the reaction vessel is discharged, and the reaction vessel detected in the incubation and luminescence detection device 2 is then transferred into the waste box 99 by the reaction vessel grasping device 5.

Referring to FIGS. 1 and 10, as an implementable way, the fully automated chemiluminescence immunoassay analyzer further comprises a mixing device 6. The mixing device 6 is configured to mix the liquid in the reaction vessel. The mixing device 6 is configured to uniformly mix the sample and the reagent in the reaction vessel to form a mixture, such that the sample and the reagent fully react in the incubation and luminescence detection device 2 to ensure the accuracy of the sample detection result. The mixing device 6 is located between the incubation and luminescence detection device 2, and the sample and reagent receiving device 1. The reaction vessel grasping device 5 transfers an empty reaction vessel from the reaction vessel receiving device 9 into the mixing device 6. The dispensing needle 31 respectively transfers the sample and the reagent from the sample and reagent receiving device 1 into the reaction vessel in the mixing device 6, and the sample and the reagent are mixed by the mixing device 6 to form a mixture. The reaction vessel grasping device 5 then transfers the reaction vessel into the incubation and luminescence detection device 2 to perform incubation and form the analyte and the impurities. After the incubation, the reaction vessel grasping device 5 transfers the reaction vessel from the incubation and luminescence detection device 2 into the magnetic separation cleaning device 4 to perform separation cleaning. After the cleaning, the reaction vessel grasping device 5 transfers the reaction vessel from the magnetic separation cleaning device 4 to the incubation and luminescence detection device 2 to perform luminescence detection. Optionally, after the substrate is added into the reaction vessel, the mixing device 6 can also uniformly mix the analyte and the substrate in the reaction vessel to increase the luminescence value of the analyte. In this case, the substrate is injected into the reaction vessel subjected to the magnetic separation cleaning, and the reaction vessel is transferred from the magnetic separation and washing device 4 into the mixing device 6 by the reaction vessel grasping device 5, and the analyte and the substrate in the reaction vessel are mixed uniformly by the mixing device 6, the reaction vessel grasping device 5 then transfers the reaction vessel from the mixing device 6 to the incubation and luminescence detection device 2, and the luminescence detection is performed by the incubation and luminescence detection device 2 after the incubation operation.

The mixing device 6 comprises a mixing seat, a mixing mechanism 64 and a mixing drive mechanism 61. The mixing drive mechanism 61 drives the movement of the mixing mechanism 64 to mix the sample and the reagent in the reaction vessel on the mixing seat. The mixing drive mechanism 61 is a power source for the mixing device 6 to achieve the mixing operation, and the mixing mechanism 64 is configured to transmit the movement of the mixing drive mechanism 61. In this embodiment, the mixing seat is a part of the mixing device 6, the mixing drive mechanism 61 drives the mixing mechanism 64 to move, and in turn the mixing mechanism 64 drives the mixing seat to move. The mixing seat is configured to mix the sample and the reagent in the reaction vessel and to mix the analyte and the substrate.

As an example, the mixing drive mechanism 61 comprises a synchronous belt structure and a motor. The synchronous belt structure is in driving connection with an output shaft of the motor and the mixing mechanism 64 to drive the mixing mechanism 64 to move, and in turn the movement is driven by the mixing mechanism 64. Of course, the synchronous belt structure may also be replaced with a chain transmission structure or a gear transmission structure, etc. The mixing mechanism 64 comprises a crankshaft, a limiting component, and a guide component. The synchronous belt structure is connected to the crankshaft. The top of the crankshaft is connected to the mixing seat and the guide component. The limiting component has a limiting groove. The guide component is movably located in the limiting groove. When the crankshaft moves eccentrically and the synchronous belt structure moves, the crankshaft can be driven to rotate eccentrically, and in turn the crankshaft drives the mixing seat and the guide component to rotate eccentrically. Since the guide component is located in the limiting groove, the limiting groove can limit the rotation movement of the guide component, thereby causing the guide member to perform a reciprocating motion in a direction along the limiting groove, such that the mixing seat can only perform the reciprocating motion in the direction along the limiting groove, so that the substances in the reaction vessel on the mixing seat can be quickly mixed. As an example, the guide member is a guide wheel.

Optionally, the mixing device 6 further comprises a mixing platform having a carrying and supporting function. Each component of the mixing device 6 is provided on the mixing platform, and the mixing platform is fixed on the carrying platform. The synchronous belt structure and the mixing seat are located on two sides of the mixing platform, and the crankshaft passes through the mixing platform and is connected to the mixing seat. The mixing device 6 further comprises a bearing seat. The crankshaft is arranged on the mixing platform via the bearing seat. With the bearing seat, interference between the crankshaft and the mixing platform is prevented, thereby ensuring the smooth operation.

In other implementations of the present disclosure, the mixing seat may also be a stationary supporting structure. The mixing drive mechanism 61 and the mixing mechanism 64 are arranged independently of the mixing seat. In this case, the mixing mechanism 64 may be a stirring rod, and the mixing drive mechanism 61 drives the stirring rod to perform a mixing operation. The stirring rod can extend into the reaction vessel, and stir the sample and the reagent in the reaction vessel or the analyte and the substrate, to uniformly mix the substances in the reaction vessel. After the mixing is completed, the stirring rod is removed from the reaction vessel. In other implementations of the present disclosure, if the sample and the reagent do not need to be subjected to the mixing operation, a mixing portion can simply support the reaction vessel, as long as the reaction vessel can be supported and transferred. When the mixing seat is a stationary support structure or simply has its supporting function, the mixing seat may be a bracket.

Further, the mixing seat is provided with a reagent and sample mixing seat 62 and a substrate mixing seat 63. The reagent and sample mixing seat 62 is configured to carry at least one reaction vessel with the sample and the reagent and to mix the sample and the reagent in the reaction vessel. The substrate mixing seat 63 is configured to carry a reaction vessel with a substrate and to mix the analyte and the substrate in the reaction vessel. The mixing seat can drive the reagent and sample mixing seat 62 and the substrate mixing seat 63 to perform the mixing operation simultaneously. Particularly, the number of the mixing mechanisms 64 is two, and the mixing drive mechanism 61 drives the reagent and sample mixing seat 62 and the substrate mixing seat 63 to perform the mixing operation simultaneously via the two mixing mechanisms 64, respectively. In other words, one mixing drive mechanism 61 can be used to simultaneously drive the reagent and sample mixing seat 62 and the substrate mixing seat 63, such that it is possible to reduce the number of power sources, reduce costs, and also reduce the volume of the mixing device 6.

The two mixing mechanisms 64 respectively correspond to the reagent and sample mixing seat 62 and the substrate mixing seat 63, and the reagent and sample mixing seat 62 and the substrate mixing seat 63 respectively perform the reciprocating motion through the cooperation of the crankshaft, the guide member, and the limiting component, realizing the mixing of the sample and the reagent in the reaction vessel in the reagent and sample mixing seat 62, and the mixing of the analyte and the sample in the reaction vessel in the substrate mixing seat 63. Moreover, the reagent and sample mixing seat 62 has at least two sample mixing positions, such that it can simultaneously carry at least two reaction vessels, and the substrate mixing seat 63 carries one reaction vessel, so that at least three reaction vessels can perform the mixing operation at the same time, thereby reducing the mixing time and increasing the operation efficiency of the whole machine. In this embodiment, the sample mixing portion 63 has two sample mixing positions, and the two sample mixing positions are collinear with the sample aspiration station and a plurality of reagent aspiration holes 1231. Of course, in other implementations of the present disclosure, the substrate mixing seat 63 has at least one substrate mixing position.

Figure 19:
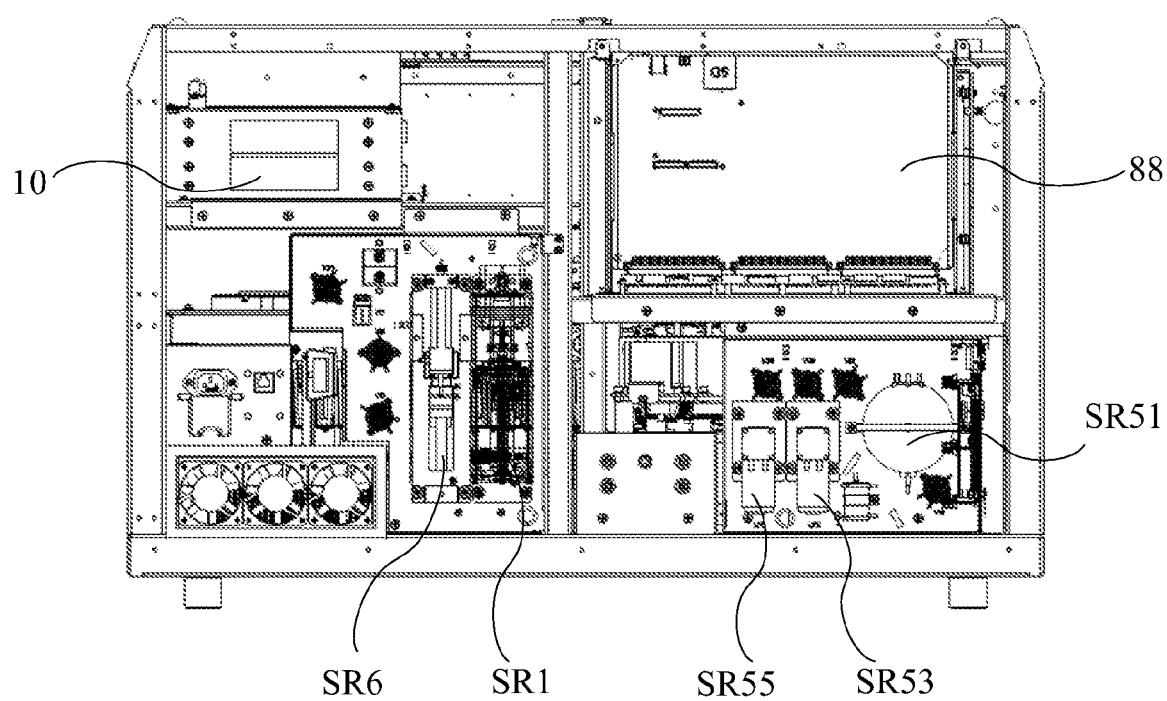
FIG. 19 is a rear view of the fully automated chemiluminescence immunoassay analyzer shown in FIG. 1.
Figure 20:
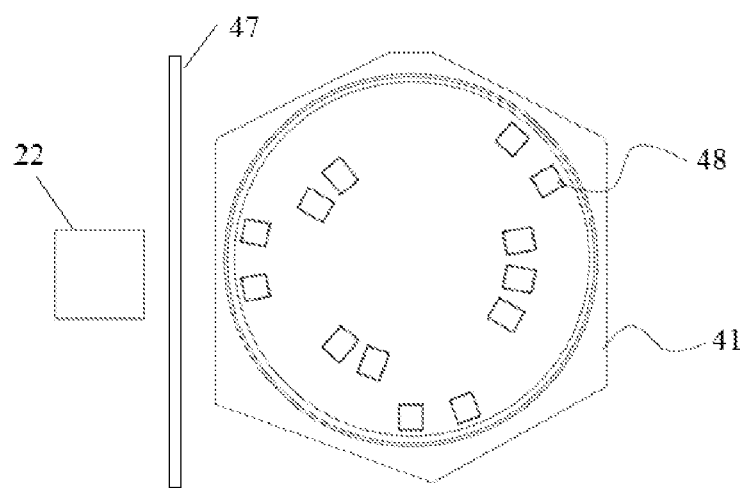
FIG. 20 is a schematic view of another magnetic shielding component of the magnetic separation cleaning device shown in FIG. 12.
Figure 21:
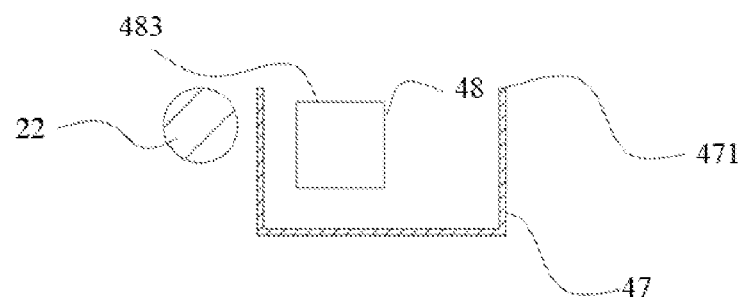
FIG. 21 is a schematic view of a magnetic shielding component of the magnetic separation cleaning device shown in FIG. 12.

Referring to FIGS. 1 and 19, as an implementable way, the fully automated chemiluminescence immunoassay analyzer further comprises a main control device 77 and a power supply device 10. The power supply device 10 is electrically connected to the main control device 77. The main control device 77 is electrically connected to the sample and reagent receiving device 1, the dispensing device 3, the incubation and luminescence detection device 2, the mixing device 6, the magnetic separation cleaning device 4, the reaction vessel grasping device 5, the reaction vessel receiving device 9, the waste box 99 and the liquid path device 8 respectively. The main control device 77 and the power supply device 10 are located below the carrying platform. A software control system is integrated in the main control device 77, and the coordinated movement of the various components of the fully automated chemiluminescence immunoassay analyzer is achieved through the software control system, increasing the operation efficiency of the fully automated chemiluminescence immunoassay analyzer. The main control device 77 being arranged below the carrying platform can reduce the volume of each component and greatly reduce the space occupied on the carrying platform, making the structure of the fully automated chemiluminescence immunoassay analyzer compact, which is conducive to the miniaturization trend of the fully automated chemiluminescence immunoassay analyzer. Moreover, the main control device 77 integrates the controls over various components together, which facilitates maintenance operations and can also reduce the cost and failure rate of the machine.

Figure 2:
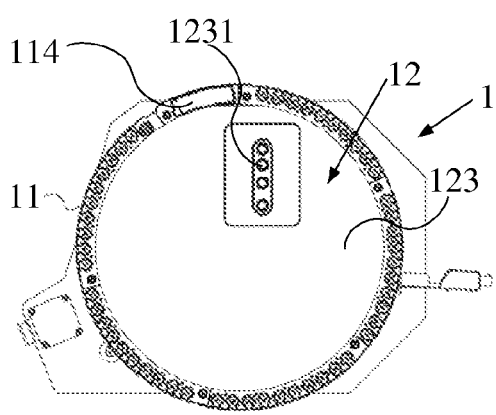
FIG. 2 is a top view of a sample and reagent receiving device in the fully automated chemiluminescence immunoassay analyzer shown in FIG. 1.
Figure 4:
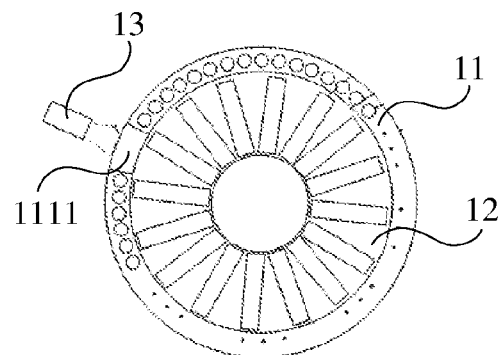
FIG. 4 is a schematic view of an identification code scanner in the sample and reagent receiving device shown in FIG. 2 scanning an identification code.
Figure 5:
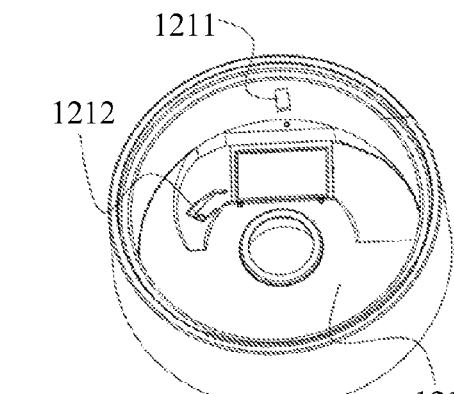
FIG. 5 is a structural schematic view of the interior of a reagent housing in the sample and reagent receiving device shown in FIG. 3.
Figure 3:
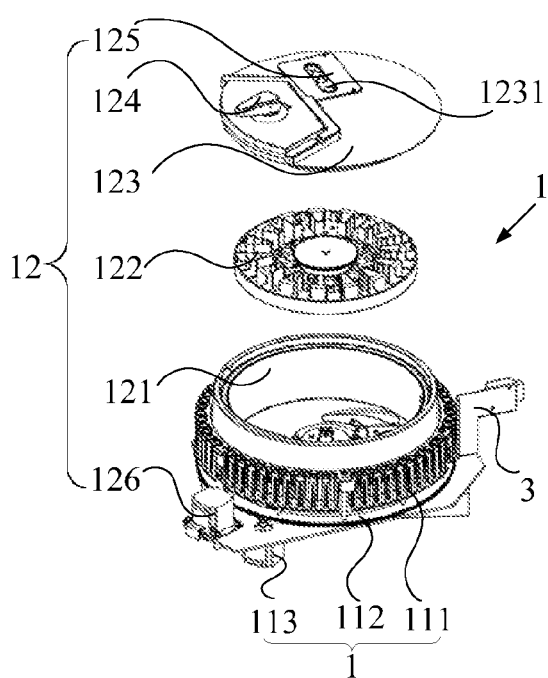
FIG. 3 is an exploded schematic view of the sample and reagent receiving device shown in FIG. 2.
Figure 6:
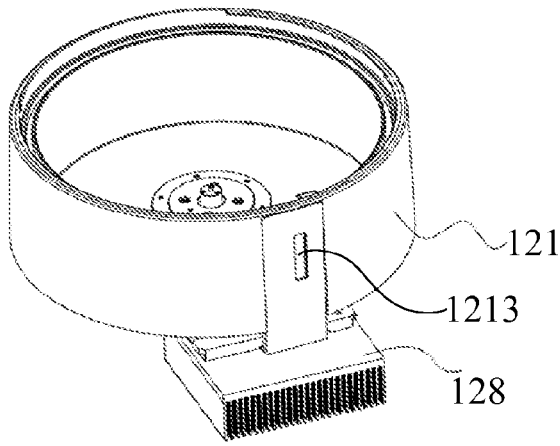
FIG. 6 is a structural schematic view of the exterior of the reagent housing in the sample and reagent receiving device shown in FIG. 3.

Referring to FIGS. 1 to 3, as an implementable way, the sample and reagent receiving device 1 comprises a sample receiving mechanism 11 for receiving the sample and a reagent receiving mechanism 12 for receiving the reagent, the sample receiving mechanism 11 is sleeved outside the reagent receiving mechanism 12, and the sample receiving mechanism 11 and the reagent receiving mechanism 12 rotate independently of each other. The sample receiving mechanism 11 can store a sample to be detected, and the reagent receiving mechanism 12 stores various reagents required for the detection of the sample. In addition, the fact that the sample reagent receiving mechanism 12 is sleeved outside the reagent receiving mechanism 12 can reduce the volume of the sample and reagent receiving device 1 and facilitate the reduction of the overall volume. In this embodiment, the reagent receiving mechanism 12 is arranged in a disc shape, the shape of the sample receiving mechanism 11 is correspondingly ring-shaped, and the sample receiving mechanism 11 and the reagent receiving mechanism 12 are arranged concentrically, such that the sample and reagent receiving device 1 occupies a minimal space. At the same time, the sample receiving mechanism 11 and the reagent receiving mechanism 12 are not in contact, ensuring that the movement between the two will not interfere, and ensuring the smooth operation. Moreover, the sample aspiration station is located on the sample receiving mechanism 11, the reagent aspiration station is located on the reagent receiving mechanism 12, and the reagent aspiration station and the sample aspiration station are fixed positions on the carrying platform. The sample receiving mechanism 11 drives a sample vessel thereon to rotate, such that the sample vessel for the sample to be detected is in the sample aspiration station. In this case, the dispensing device 3 can aspirate the sample at the sample aspiration station and transfer the sample into the reaction vessel on the mixing seat. The reagent receiving mechanism 12 drives a reagent vessel thereon to rotate, such that the reagent vessel to be aspirated is in the reagent aspiration station. In this case, the dispensing device 3 can aspirate the reagent at the reagent aspiration station and transfer the reagent into the reaction vessel on the mixing seat.

Particularly, the sample receiving mechanism 11 comprises a chassis 112, the reagent receiving mechanism 12 comprises a reagent housing 121, the chassis 112 is configured to store the sample, and the reagent housing 121 is configured to store the reagent. The chassis 112 is coaxially sleeved outside the reagent housing 121, and the chassis 112 and the reagent housing 121 rotate independently of each other.

The sample receiving mechanism 11 further comprises a plurality of sample holders 111 arranged in an arc shape, and a sample receiving driving structure 113. The sample holder 111 is configured to carry a sample vessel with a sample. The plurality of sample holders 111 are sequentially installed on the chassis 112. The sample receiving driving structure 113 drives the chassis 112 to rotate, and drives the sample holders 111 to rotate. Each arc-shaped sample holder 111 can store a plurality of sample vessels with samples, and the arc radius of each sample holder 111 is consistent, which ensures that the plurality of sample holders 111 form a ring structure after assembly. As an example, the sample holder 111 comprises an upper bracket and a plurality of support columns. The plurality of support columns support the upper bracket. The upper bracket is provided with a plurality of accommodation holes, and the sample vessels are installed in the accommodation holes. Moreover, the plurality of support columns are arranged at intervals, and the plurality of support columns may be directly installed on the chassis 112. Of course, the sample holder 111 may further comprise a lower bracket. The lower bracket is arranged on the chassis 112, and the bottoms of the support columns are installed on the lower bracket. It can be understood that the sample holders 111 may be sequentially connected end to end, or there may be a gap between them. The sample holders 111 may be connected in an overlapping manner, or connected via connection members and other structures; and they may also be fixed by means of snap-fit fasteners, connection members, etc. In this embodiment, the number of the sample holders 111 is five. The chassis 111 is an annular sample disc.

As an example, the sample receiving driving structure 113 comprises a sample receiving drive motor and a gear transmission structure. The chassis 112 is provided with a toothed portion. The gear transmission structure is in driving connection with the sample receiving drive motor and the chassis 112. The sample receiving drive motor drives the synchronous belt structure, to drive the chassis 112 to rotate. Of course, the gear transmission structure may also be replaced with a chain transmission structure, a synchronous belt structure, etc. The sample receiving driving structure 113 drives the chassis 112, to drive the sample holder 111 thereon to rotate, such that the sample vessel where detection is to be performed rotates to the sample aspiration station, and the dispensing device 3 aspirates the sample and then transfers the sample into the vessel on the mixing seat. After the dispensing device 3 aspirates the sample, the sample receiving driving structure 113 can drive the chassis 112, to drive the sample holder 111 to rotate again, such that the next sample vessel where detection is to be performed rotates to the sample aspiration station.

Optionally, the sample and reagent receiving device 1 further comprises a storage fixing plate. The storage fixing plate is provided on the carrying platform for mounting various components of the sample receiving mechanism 11 and the reagent receiving mechanism 12, to facilitate the driving of the rotation of the sample receiving mechanism 11 and the reagent receiving mechanism 12 and prevent the occurrence of interference. The sample receiving driving structure 113 is provided on the storage fixing plate, the chassis 112 is rotatably fixed to the storage fixing plate, and the sample receiving driving structure 113 drives the chassis 112, to drive the sample holder 111 and the sample vessels thereon to rotate relative to the storage fixing plate.

Still optionally, the sample receiving mechanism 11 further comprises a pulley bearing provided with a slide way, the slide bearing is placed flat on the storage fixing plate, and an edge of the chassis 112 is located in the slide way of the pulley bearing. When the sample receiving driving structure 113 drives the chassis 112 to rotate, the pulley bearing can support the chassis 112 such that the chassis 112 rotates smoothly, and at the same time, the slide way can also guide the chassis 112 to rotate. As an example, there are a plurality of pulley bearings, and the plurality of pulley bearings are uniformly distributed on a peripheral side of the chassis 112 to ensure that the chassis 112 is uniformly stressed and supported reliably. In this embodiment, the number of the pulley bearings is four.

The reagent receiving mechanism 12 further comprises a reagent disc 122 and a reagent disc driving structure 126. The reagent disc 122 is accommodated in the reagent housing 121. The reagent disc 122 is configured to store reagent vessels with reagents. The reagent disc driving structure 126 drives the reagent disc 122 to rotate relative to the sample receiving mechanism 11. The reagent housing 121 is fixed on the storage fixing plate, and the reagent disc driving structure 126 is provided on the storage fixing plate, extends into the reagent housing 121 and is connected to the reagent disc 122, so as to drive the reagent disc 122 to rotate in the reagent housing 121. The reagent housing 121 can have a refrigeration function, and can refrigerate the reagent on the reagent disc 122 to achieve low-temperature preservation of the reagent. Moreover, when the whole machine is in a turned-off state, the reagent housing 121 can support the continuous cooling of the reagent to a lower temperature, such that the reagent stays in the machine overnight.

The reagent disc driving structure 126 comprises a reagent storage drive motor, a synchronous belt structure and a rotary shaft, wherein the rotary shaft extends into the reagent housing 121, the synchronous belt structure is in driving connection with the reagent storage drive motor and the rotary shaft, and the reagent disc 122 is installed on the rotary shaft. The reagent storage drive motor drives the rotary shaft to rotate via the synchronous belt structure, and the rotary shaft in turn drives the reagent disc 122 to rotate, such that the reagent vessel where aspiration is to be performed is transferred from the reagent disc 122 to the reagent aspiration station, and the dispensing device 3 aspirates the reagent and transfers the reagent into the mixing seat. After the dispensing device 3 aspirates the reagent, the reagent disc driving structure 126 can drive the reagent disc 122 to rotate again, such that the next reagent vessel where detection is to be performed rotates to the reagent aspiration station. Of course, the synchronous belt structure may be replaced with a gear transmission structure, a chain transmission structure, etc.

Optionally, the reagent disc driving structure 126 further comprises a rotary bearing. The rotary bearing is provided on the reagent housing 121, an outer ring of the rotary bearing is connected to the reagent housing 121, an inner ring of the rotary bearing is connected to the rotary shaft, and the reagent storage drive motor drives the rotary shaft to rotate via the synchronous belt structure, such that the rotary shaft drives the rotation of the center of the reagent housing 121 at the position of the reagent disc 122. The rotary shaft is fixed on the reagent housing 121 via the rotary bearing, and the rotary bearing can also avoid interference between the rotating rotary shaft and the stationary reagent housing 121, ensuring the smooth and reliable rotation.

Still further, the reagent receiving mechanism 12 further comprises a reagent housing lid 123. The reagent housing lid 123 covers the reagent housing 121. The reagent housing lid 123 can prevent the loss of cold from the reagent housing 121, ensuring the cooling effect, and saving costs. Moreover, the reagent housing lid 123 is provided with a plurality of reagent aspiration holes 1231. The plurality of reagent aspiration holes 1231 are arranged in a radial direction of the reagent disc 122 and located on a straight line, and the dispensing needle 31 can extend into any one of the reagent aspiration holes 1231 to aspirate a reagent. The plurality of reagent aspiration holes 1231 enable the dispensing needle 31 to aspirate reagents from reagent vessels at different positions. In this way, the number of reagent vessels on the reagent disc 122 can be increased. It can be understood that multiple circles of reagent vessels are nested circle by circle, and the reagent disc 122 is further provided with a plurality of reagent vessels in the same radial direction. Moreover, the reagent vessels in the same radial direction respectively correspond to the plurality of reagent aspiration holes 1231, such that the dispensing needle 31 can aspirate the reagent at any position without rotating, which is convenient for selection and saves on the time for transferring the reagent. It should be noted that each reagent aspiration hole 1231 is a reagent aspiration station, and the dispensing needle 31 can aspirate a reagent at any reagent aspiration station.

In an embodiment, the reagent housing lid 123 is provided with four reagent aspiration holes 1231. The four reagent aspiration holes 1231 are located on the same straight line, and the four reagent aspiration holes 1231 further extend in a radial direction of the reagent disc 122. As a reagent is transferred, the reagent disc driving structure 126 drives the reagent disc 122, to drive the reaction vessels thereon to rotate, such that the reaction vessel for the reagent to be aspirated rotates to the reagent aspiration hole 1231, the four reagent vessels respectively correspond to the four reagent aspiration holes 1231, and the dispensing needle 31 can select the reagent aspiration hole 1231 corresponding to the desired reagent to aspirate the reagent. Moreover, the provision of the reagent aspiration holes 1231 can also prevent the excessive opening of the reagent housing lid 123 resulting in the overflowing of cold from the reagent housing 121.

Further, the reagent receiving mechanism 12 further comprises a switching cover 124. The reagent housing lid 123 is provided with a placement/removal opening for placing or removing the reagent vessel. The switching cover 124 is switchably located in the placement/removal opening of the reagent housing lid 123. The switching cover 124 is a small cover on the reagent housing lid 123. When the reagent in a certain reagent vessel on the reagent disc 122 needs to be replenished, the switching cover 124 is opened and the reagent vessel is removed through the placement/removal opening. After the reagent has been replenished, the reagent vessel is placed on the reagent disc 122 through the placement/removal opening. In this way, it is convenient for the operator to use, and the loss of cold from the reagent housing 121 can also be avoided. Optionally, one end of the switching cover 124 is rotatably mounted on the reagent housing lid 123, and the other end of the switching cover 124 can rotate about the reagent housing lid 123 to open or close the placement/removal opening. Of course, in other implementations of the present disclosure, the switching cover 124 may also be removed in its entirety, as long as it can be fixed by a positioning pin or the like.

Referring to FIGS. 1 and 9, as an implementable way, the dispensing device 3 further comprises a dispensing needle holder and a dispensing drive portion. The dispensing needle holder is located on the rear side above the sample and reagent receiving device 1, and the dispensing drive portion is provided on the dispensing needle holder for driving the dispensing needle 31 to move. Particularly, the dispensing drive portion comprises a horizontal movement mechanism 33 and a vertical movement mechanism 32. The vertical movement mechanism 32 is provided on the horizontal movement mechanism 33, the dispensing needle 31 is provided on the vertical movement mechanism 32, and the movements of the vertical movement mechanism 32 and the horizontal movement mechanism 33 cause the dispensing needle 31 to transfer the sample and the reagent between the sample and reagent receiving device 1 and the mixing seat. The vertical movement mechanism 32 can drive the dispensing needle 31 to ascend and descend, so as to aspirate or discharge the sample and the reagent. The horizontal movement mechanism 33 can drive the dispensing needle 31 to move in a horizontal direction to transfer the sample and the reagent. When the vertical movement mechanism 32 drives the dispensing needle 31 to descend, the dispensing needle 31 aspirates the sample or the reagent. After the aspiration is completed, the vertical movement mechanism 32 drives the dispensing needle 31 to restore. The horizontal movement mechanism 33 then drives the dispensing needle 31 to move in the horizontal direction such that the dispensing needle 31 is moved to the mixing seat, the vertical movement mechanism 32 drives the dispensing needle 31 to descend, and the dispensing needle 31 discharges the sample or the reagent. After the discharge is completed, the vertical movement mechanism 32 drives the dispensing needle 31 to restore. The horizontal movement mechanism 33 then drives the dispensing needle 31 to move in the horizontal direction, such that the dispensing needle 31 returns to the sample and reagent receiving device 1 to continue the sample or reagent aspiration operation.

The dispensing needle holder comprises a dispensing fixing plate and a dispensing horizontal mounting plate. The dispensing fixing plate is configured to support other components of the dispensing device 3. The horizontal movement mechanism 33 comprises a dispensing horizontal drive motor and a dispensing horizontal transmission structure. The dispensing horizontal drive motor and the dispensing horizontal transmission structure are both installed on the dispensing horizontal mounting plate, and the dispensing horizontal mounting plate is installed on the dispensing horizontal transmission structure. The dispensing horizontal drive motor drives the dispensing horizontal transmission structure to move, such that the horizontal transmission structure drives the dispensing horizontal mounting plate to move horizontally. The vertical movement mechanism 32 comprises a dispensing vertical drive motor and a dispensing vertical transmission structure. The dispensing vertical drive motor and the dispensing vertical transmission structure are both provided on the dispensing horizontal mounting plate. The movement of the dispensing horizontal mounting plate can drive the dispensing vertical drive motor and the dispensing vertical transmission structure to move. The dispensing needle holder further comprises a dispensing vertical fixing plate. The dispensing vertical fixing plate is installed on the dispensing vertical transmission structure, and the dispensing needle 31 is installed on the dispensing vertical fixing plate. The dispensing vertical drive motor drives the dispensing vertical transmission structure to move, this can drive the dispensing vertical fixing plate to ascend and descend, and in turn drive the dispensing needle 31 to ascend and descend. Moreover, through the dispensing horizontal transmission structure, the dispensing horizontal drive motor drives the dispensing vertical movement mechanism 32 and the dispensing vertical fixing plate to move horizontally, which in turn drives the dispensing to move horizontally.

As an example, the dispensing horizontal transmission structure and the dispensing vertical transmission structure may be synchronous belt structures. Of course, the dispensing horizontal transmission structure and the dispensing vertical transmission structure may also be chain transmission structures, rack and pinion structures or other structures capable of achieving linear motion. Through the cooperation of the horizontal movement mechanism 33 and the vertical movement mechanism 32, the dispensing needle 31 is controlled to move horizontally and to ascend and descend, so as to realize the aspiration, discharge and transfer of the sample and the reagent. Moreover, as the reagent is aspirated, the vertical movement mechanism 32 drives the dispensing needle 31 to descend. In this case, the dispensing needle 31 extends into the reagent vessel in the reagent housing 121 through the reagent aspiration hole 1231, and aspirates the reagent. After the aspiration is completed, the vertical movement mechanism 32 drives the dispensing needle 31 to ascend. In this case, the dispensing needle 31 leaves the reagent housing 121 through the reagent aspiration hole 1231. When the sample is aspirated, the dispensing needle 31 is operated at the sample aspiration station, and the operation steps are exactly the same as the aspiration of the reagent, which will not be described in detail here.

Further, the dispensing device 3 further comprises a dispensing needle swab 34 connected to the horizontal movement mechanism 33. The dispensing needle swab 34 is sleeved on the dispensing needle 31 and can move horizontally along with the dispensing needle 31. When the dispensing needle 31 ascends and descends relative to the dispensing needle swab 34, the dispensing needle swab can clean an outer wall of the dispensing needle. Particularly, the horizontal movement mechanism 33 also drives the dispensing needle swab 34 to move, and when the vertical movement mechanism 32 drives the dispensing needle 31 to ascend and descend, the dispensing needle swab 34 cleans the outer wall of the dispensing needle 31. That is to say, the dispensing device 3 has its own cleaning function module, and the cleaning function module can move horizontally along with the dispensing needle 31. When the dispensing needle 31 moves vertically or is stationary, the cleaning function module can clean the dispensing needle 31. In this way, the dispensing needle 31 can be prevented from frequently accessing a cleaning pool, and the working efficiency of the dispensing needle 31 is improved.

It can be understood that after each time the dispensing needle 31 aspirates or discharges the sample and the reagent, it needs to be cleaned to prevent the sample or the reagent from remaining on the outer wall of the dispensing needle 31 to cause cross contamination and affect the detection accuracy of the sample. As an example, the dispensing needle swab 34 is provided with a dispensing cleaning central hole, a dispensing cleaning inlet, and a dispensing cleaning outlet. The dispensing needle 31 passes through the dispensing needle swab 34 through the dispensing cleaning central hole, and when the dispensing needle 31 ascends and descends, the dispensing needle 31 can move along the dispensing cleaning central hole. Moreover, during the ascending and descending movements of the dispensing needle 31, the dispensing needle 31 can be cleaned by a cleaning liquid in the dispensing needle swab 34. Particularly, the cleaning liquid flows into the dispensing needle swab 34 through the dispensing cleaning inlet, and flows out of the dispensing cleaning outlet. The cleaning liquid can come into contact with the outer wall of the dispensing needle 31 during flowing, thereby cleaning the surface, that is, the outer wall of the dispensing needle 31. The waste cleaning liquid flowing out of the dispensing cleaning outlet can be discharged into a waste liquid bucket, which is located below the carrying platform. It should be noted that the delivery and discharge of the cleaning liquid in the dispensing needle swab 34 are realized by means of the liquid path device 8, which will be explained in detail later.

Still further, the dispensing device 3 further comprises a cleaning pool 35. The cleaning pool 35 is provided on the mixing platform. The cleaning pool 35 is configured to receive the waste cleaning liquid after the inner wall of the dispensing needle 31 is cleaned. The cleaning pool 35 is a fixed cleaning module. After the dispensing needle 31 adds the samples and the reagent to the reaction vessel in the mixing device 6, an inner wall of the dispensing needle 31 also needs to be cleaned to prevent the sample or the reagent from remaining on the inner wall of the dispensing needle 31 to cause cross contamination and affect the detection accuracy of the sample.

After the dispensing needle 31 adds the samples and the reagent to the reaction vessel at the reagent and sample mixing seat 62 of the mixing seat, the horizontal movement mechanism 33 drives the dispensing needle 31 to move to the cleaning pool 35, and the cleaning liquid is led into a needle tail of the dispensing needle 31, is discharged into the cleaning pool 35 through the dispensing needle 31, and is discharged into the waste liquid bucket from the cleaning pool 35. Moreover, after the dispensing needle 31 cleans the inner wall and the waste cleaning liquid is discharged to the cleaning pool 35, the waste cleaning liquid generates a vortex in the cleaning pool 35, and the vortex in turn can also clean the outer wall of the dispensing needle 31.

Of course, in other implementations of the present disclosure, the cleaning pool 35 may also be located on the carrying platform between the mixing seat and the sample and reagent receiving device 1. Moreover, the reagent and sample mixing seat 62 is arranged adjacent to the cleaning pool 35, and the cleaning pool 35 is located between the reagent and sample mixing seat 62 and the sample aspiration station. After the dispensing needle 31 adds the sample or the reagent to the reagent and sample mixing seat 62, the dispensing needle 31 needs to return to the sample and reagent receiving device 1 to aspirate the sample or the reagent. The cleaning pool 35 is located on the return path of the dispensing needle 31. When the dispensing needle 31 is returning, it first moves to the cleaning pool 35 for cleaning, and then continues to return for the operation of aspirating the sample or the reagent. In this way, the movement path of the dispensing needle 31 can be reduced, and the efficiency of transferring the sample and the reagent by the dispensing needle 31 can be improved.

Of course, in other implementations of the present disclosure, the cleaning liquid may also be injected into the cleaning pool 35, and the vertical movement mechanism 32 controls the dispensing needle 31 to descend to clean the outer wall of the dispensing needle 31. After the cleaning is completed, the vertical movement mechanism 32 drives the dispensing needle 31 to ascend, and at the same time, the waste cleaning liquid in the cleaning pool 35 is discharged. It can be understood that the delivery of the cleaning liquid and the discharge of the waste cleaning liquid are realized by means of the liquid path device 8, which will be explained in detail later.

Preferably, the sample aspiration station, the plurality of reagent aspiration holes 1231, the reagent and sample mixing seat 62, and the cleaning pool 35 are collinear. That is to say, the sample aspiration station of the sample receiving mechanism 11, the plurality of reagent aspiration holes 1231 of the reagent receiving mechanism 12, the reagent and sample mixing seat 62 of the mixing seat, and the second cleaning mechanism 35 are on a straight line, and this straight line coincides with the plane where the horizontal movement and the vertical movement of the dispensing needle 31 are located. In this way, when the horizontal movement mechanism 33 drives the dispensing needle 31 to move horizontally, the dispensing needle 31 can respectively pass through the sample aspiration station, the plurality of reagent aspiration holes 1231, the reagent and sample mixing seat 62, and the cleaning pool 35, such that one dispensing needle 31 can be used to both aspirate the sample or the reagent and accurately fill same to the reagent and sample mixing seat 62, and the dispensing needle can be cleaned, so that the fully automated chemiluminescence immunoassay analyzer has a compact structure and a reduced overall volume, and the cost of the analyzer can also be reduced.

Referring to FIGS. 1, 9, 16 and 19, as an implementable way, the liquid path device 8 comprises a dispensing liquid path system 81. The dispensing liquid path system 81 is configured to realize the aspiration and discharge of the sample and the reagent by the dispensing needle 31 and the cleaning of the dispensing needle 31. The dispensing liquid path system 81 is connected to the dispensing needle 31, can control the dispensing needle 31 to aspirate the sample or the reagent, and can also discharge the sample or the reagent from the dispensing needle 31. Particularly, the dispensing liquid path system 81 of the fully automated chemiluminescence immunoassay analyzer further comprises a first dispensing syringe SR1. The first dispensing syringe SR1 is located on the rear side of the carrying platform (particularly, in the right-hand region of the rear side of the carrying platform), and the first dispensing syringe SR1 is respectively in communication with the dispensing needle 31 and the dispensing needle swab 34 through pipelines, and supplies the cleaning liquid to the dispensing needle 31 and the dispensing needle swab 34.

Particularly, the dispensing liquid path system 81 further comprises a dispensing aspiration/discharge pipeline 811 and a first dispensing control valve V811. The first dispensing control valve V811 is connected between the first dispensing syringe SR1 and the dispensing aspiration/discharge pipeline 811 for controlling the opening and closing of the dispensing aspiration/discharge pipeline 811. The dispensing aspiration/discharge pipeline 811 is also connected to the dispensing needle 31 of the dispensing device 3. When the first dispensing control valve V811 is in communication with the dispensing aspiration/discharge pipeline 811 and the first dispensing syringe SR1, the dispensing device 3 aspirates and discharges the sample and the reagent. It can be understood that the control valve in the present disclosure may refer to a two-position three-way valve, or a multi-position multi-way valve, or other valves that can be switched on and off, such as a three-way coordinated switch valve.

One end of the first dispensing control valve V811 is connected to the first dispensing syringe SR1, the other end of the first dispensing control valve V811 is connected to one end of the dispensing aspiration/discharge pipeline 811, and the other end of the dispensing aspiration/discharge pipeline 811 is connected to the needle tail of the dispensing needle 31. When the first dispensing control valve V811 controls the dispense aspiration/discharge pipeline 811 to be a passage, the first dispensing control valve V811 communicates the first dispense syringe SR1 with the dispensing aspiration/discharge pipeline 811, and the sample or the reagent is aspirated by the dispensing needle 31 and stored in the first dispensing syringe SR1. After the aspiration is completed, the horizontal movement mechanism 33 and the vertical movement mechanism 32 drive the dispensing needle 31 to move to the reagent and sample mixing seat 62 of the mixing device 6, the first dispensing syringe SR1 discharges the aspirated sample and reagent into the reaction vessel through the dispensing aspiration/discharge pipeline 811 via the dispensing needle 31. When the inner wall of the dispensing needle 31 is cleaned, the first dispensing syringe SR1 delivers the cleaning liquid into the dispensing needle 31 through the dispensing aspiration/discharge pipeline 811 to clean the inner wall of the dispensing needle 31. After the cleaning is completed, the liquid in the dispensing needle 31 is discharged.

Moreover, the dispensing liquid path system 81 is also connected to the dispensing needle swab 34 to supply the cleaning liquid to the dispensing needle swab 34. In this way, the dispensing liquid path system 81 can be driven by one power source, such that not only the aspiration and discharge of the sample and the reagent and the cleaning of the inner wall of the dispensing needle 31 can be achieved, but also the cleaning of the outer wall of the dispensing needle 31 can be achieved, so that one syringe device is omitted compared to the traditional designs. Particularly, the dispensing liquid path system 81 further comprises a first dispensing cleaning pipeline 812. The first dispensing cleaning pipeline 812 is connected to the first dispensing control valve V811 and the dispensing needle swab 34. The first dispensing control valve V811 disconnects the first dispensing syringe SR1 from the dispensing aspiration/discharge pipeline 811 while communicating the first dispensing cleaning pipeline 812 with the first dispensing syringe SR1, to clean the outer wall of the dispensing needle 31.

It can be understood that one end of the first dispensing control valve V811 is connected to the first dispensing syringe SR1, and the other two ends of the first dispensing control valve V811 are respectively connected to the dispensing aspiration/discharge pipeline 811 and the first dispensing cleaning pipeline 812. The other end of the first dispensing cleaning pipeline 812 is connected to the dispensing cleaning inlet of the dispensing needle swab 34. The first dispensing control valve V811 disconnects the first dispensing syringe SR1 from the first dispensing cleaning pipeline 812 while communicating the first dispensing syringe SR1 with the dispensing aspiration/discharge pipeline 811. In this case, the first dispensing syringe SR1 aspirates the sample or the reagent through the dispensing aspiration/discharge pipeline 811 via the dispensing needle 31, and stores the sample or the reagent in the first dispensing syringe SR1. After the aspiration is completed, the horizontal movement mechanism 33 and the vertical movement mechanism 32 drive the dispensing needle 31 to move to the reagent and sample mixing seat 62 of the mixing device 6, the first dispensing syringe SR1 discharges the aspirated sample and reagent into the reaction vessel through the dispensing aspiration/discharge pipeline 811 via the dispensing needle 31. When the inner wall of the dispensing needle 31 is cleaned, the first dispensing syringe SR1 delivers the cleaning liquid into the dispensing needle 31 through the dispensing aspiration/discharge pipeline 811 to clean the inner wall of the dispensing needle 31. After the cleaning is completed, the liquid in the dispensing needle 31 is discharged. When the outer wall of the dispensing needle 31 is cleaned, the first dispensing control valve V811 communicates the first dispensing syringe SR1 with the first dispensing cleaning pipeline 812 while disconnecting the first dispensing syringe SR1 and the dispensing aspiration/discharge pipeline 811. In this case, the first dispensing syringe SR1 delivers the cleaning liquid from the dispensing cleaning inlet of the dispensing needle swab 34 into the dispensing needle swab 34 through the first dispensing cleaning pipeline 812, and after the outer wall of the dispensing needle 31 is cleaned, the cleaning liquid is discharged from the dispensing cleaning outlet of the dispensing needle swab 34.

The first dispensing syringe SR1 is a power source for the dispensing fluid system 81 to aspirate the sample or the reagent and to deliver the cleaning liquid. The first dispensing syringe SR1 controls the dispensing needle 31 to aspirate and discharge the sample and the reagent, and also to aspirate and discharge the cleaning liquid. The first dispense syringe SR1 realizes the aspiration and discharge operations and the cleaning operation of the dispensing needle 31 by means of one valve, that is, the first dispensing control valve V811, so that the functions of the dispensing needle 31 aspirating and discharging the sample and the reagent and cleaning the inner wall of the dispensing needle 31 can be achieved, cleaning the outer wall of the dispensing needle 31 can also be achieved.

Further, the dispensing liquid path system 81 can also aspirate the cleaning liquid without the need of aspirating by using the dispensing needle 31, which improves the utilization rate of the dispensing needle 31, and also facilitates the cleaning of the inner and outer walls of the dispensing needle 31 to increase the frequency at which the dispensing needle 31 aspirates the sample and the reagent, thereby increasing the operation efficiency of the whole machine. Of course, in other implementations of the present disclosure, the dispensing needle 31 may also be used to aspirate the cleaning liquid for cleaning. For example, the dispensing needle 31 can aspirate the cleaning liquid to clean the inner wall of the dispensing needle 31, and can transfer the cleaning liquid into the cleaning pool 35 to clean the outer wall of the dispensing needle 31. Through the switch control of the first dispensing control valve V811, the cleaning liquid can enter the dispensing needle swab 34 through the dispensing aspiration/discharge pipeline 811, the first dispensing syringe SR1, and the first dispensing cleaning pipeline 812.

Particularly, the dispensing liquid path system 81 further comprises a second dispensing control valve V812 and a second dispensing cleaning pipeline 813. The second dispensing control valve V812 is connected to the first dispensing syringe SR1 and the first dispensing control valve V811, the second dispensing control valve V812 is connected to the second dispensing cleaning pipeline 813, and the second dispensing cleaning pipeline 813 is also in communication with a cleaning liquid container with a cleaning liquid. The second dispensing control valve V812 disconnects the first dispensing syringe SR1 from the first dispensing control valve V811 while communicating the first dispensing syringe SR1 with the second dispensing cleaning pipeline 813, to clean the dispensing needle 31. The second dispensing control valve V812 communicates the first dispensing syringe SR1 with the first dispensing control valve V811 while disconnecting the first dispensing syringe SR1 from the second dispensing cleaning pipeline 813, such that the aspirated cleaning liquid can be delivered into the dispensing needle 31 or the dispensing needle swab 34.

One end of the second dispensing control valve V812 is connected to the first dispensing syringe SR1, and the other two ends of the second dispensing control valve V812 are respectively connected to one end of the second dispensing cleaning pipeline 813 and one end of the first dispensing control valve V811. One end of the second dispensing cleaning pipeline 813 extends into the cleaning liquid container. The other two ends of the first dispensing control valve V811 are connected to the dispensing aspiration/discharge pipeline 811 and the first dispensing cleaning pipeline 812 mentioned above.

During cleaning, the dispensing liquid path system 81 first aspirates the cleaning liquid, and then delivers the cleaning liquid into the dispensing needle 31 or the dispensing needle swab 34. Particularly, the second dispensing control valve V812 disconnects the first dispensing syringe SR1 from the first dispensing control valve V811 while communicating the first dispensing syringe SR1 with the second dispensing cleaning pipeline 813. In this case, the first dispensing syringe SR1 aspirates the cleaning liquid from the cleaning liquid container through the second dispensing cleaning pipeline 813, and stores the cleaning liquid in the first dispensing syringe SR1. The second dispensing control valve V812 then communicates the first dispensing syringe SR1 with the first dispensing control valve V811 while disconnecting the first dispensing syringe SR1 from the second dispensing cleaning pipeline 813. In this case, if the outer wall of the dispensing needle 31 is to be cleaned, the first dispensing control valve V811 communicates the first dispensing syringe SR1 with the dispensing needle swab 34, and the first dispensing syringe SR1 delivers the cleaning liquid into the dispensing needle swab 34. If the inner wall of the dispensing needle 31 is to be cleaned, the first dispensing control valve V811 communicates the first dispensing syringe SR1 and the dispensing aspiration/discharge pipeline 811, and the first dispensing syringe SR1 delivers the cleaning liquid into the dispensing needle 31.

Moreover, the dispensing liquid path system 81 of the fully automated chemiluminescence immunoassay analyzer further comprises a second dispensing syringe SR6. The second dispensing syringe SR6 is connected between the first dispensing syringe SR1 and the dispensing needle 31, and is located on the rear side of the carrying platform (particularly, in the right-hand region of the rear side of the carrying platform) such that the dispensing needle 31 aspirates the sample or the reagent. The volume of the second dispensing syringe SR6 is smaller than that of the first dispensing syringe SR1, and the second dispensing syringe SR6 is a quantitative syringe. This can achieve quantitative aspiration of the sample and/or the reagent, and ensure the reliable aspiration of the sample and the reagent. Moreover, the cleaning liquid aspirated by the first dispensing syringe SR1 can be delivered into the dispensing needle 31 via the second dispensing syringe SR6, and the second dispensing syringe SR6 can also be cleaned during the delivery to further avoid cross contamination.

Still further, the dispensing liquid path system 81 further comprises a first dispensing waste liquid discharge device. The first dispensing waste liquid discharge device is connected to the dispensing needle swab 34 for discharging the waste cleaning liquid from the dispensing needle swab 34. Particularly, one end of the first dispensing waste liquid discharge device is connected to the dispensing cleaning outlet of the dispensing needle swab 34, and the other end of the first dispensing waste liquid discharge device extends into the waste liquid bucket below the carrying platform. The first dispense syringe SR1 delivers through the dispensing cleaning inlet into the dispensing needle swab 34 via the first dispensing cleaning pipeline 812. After the cleaning is completed, the waste cleaning liquid is delivered into the first dispensing waste liquid discharge device through the dispensing cleaning outlet, and then into the waste liquid bucket to achieve the discharge of the waste cleaning liquid.

Still further, the dispensing liquid path system 81 further comprises a second dispensing waste liquid discharge device. The second dispensing waste liquid discharge device is connected to the cleaning pool 35 for discharging the waste cleaning liquid into the cleaning pool 35. Particularly, one end of the second dispensing waste liquid discharge device is connected to the bottom of the cleaning pool 35, and the other end of the second dispensing waste liquid discharge device extends into the waste liquid bucket below the carrying platform. The first dispense syringe SR1 delivers the cleaning liquid into the dispensing needle 31 through the dispensing aspiration/discharge pipeline 811 to clean the inner wall of the dispensing needle 31. After the cleaning is completed, the waste cleaning liquid is discharged into the cleaning pool 35, and the waste cleaning liquid is then delivered into the second dispensing waste liquid discharge device through the bottom of the cleaning pool 35, and then into the waste liquid bucket to achieve the discharge of the waste cleaning liquid.

In this embodiment, the dispensing liquid path system 81 of the fully automated chemiluminescence immunoassay analyzer further comprises a second vacuum pump SR55. The second vacuum pump SR55 is located on the rear side of the carrying platform (particularly, in the left right-hand region of the rear side of the carrying platform). The second vacuum pump SR55 is respectively connected to the dispensing needle swab 34 and the cleaning pool 35, and provides power for discharging the waste cleaning liquid from the dispensing needle swab 34 and the cleaning pool 35. Particularly, the dispensing liquid path system 81 further comprises a first dispensing liquid discharge pipeline 814, a second dispensing liquid discharge pipeline 815, and a third dispensing control valve V813. The first dispensing liquid discharge pipeline 814 is in communication with the dispensing needle swab 34, the second dispensing liquid discharge pipeline 815 is in communication with the cleaning pool 35, and the first dispensing liquid discharge pipeline 814 and the second dispensing liquid discharge pipeline 815 are also in communication with the second vacuum pump SR55 via the third dispensing control valve V813. The waste cleaning liquid is discharged into the waste liquid bucket by the second vacuum pump SR55. After the cleaning is completed, the dispensing liquid path system 81 can further discharge the waste cleaning liquid into the waste liquid bucket. One end of the first dispensing liquid discharge pipeline 814 is in communication with the separation cleaning outlet of the dispensing needle swab 34, and the other end of the first dispensing liquid discharge pipeline 814 is connected to the second vacuum pump SR55 via the third dispensing control valve V813. One end of the second dispensing liquid discharge pipeline 815 is connected to the cleaning pool 35, and the other end of the second dispensing liquid discharge pipeline 815 is connected to the second vacuum pump SR55 via the third dispensing control valve V813.

The first dispensing liquid discharge pipeline 814 can discharge the waste cleaning liquid from the dispensing needle swab 34, and the second dispensing liquid discharge pipeline 815 can discharge the waste cleaning liquid that is discharged from the dispensing needle 31 into the cleaning pool 35. When the waste cleaning liquid in the dispensing needle swab 34 is discharged, the third dispensing control valve V813 communicates the first dispensing liquid discharge pipeline 814 with the second vacuum pump SR55, and disconnects the second dispensing liquid discharge pipeline 815 from the second vacuum pump SR55. In this case, the cleaning liquid in the dispensing needle swab 34 can be discharged into the waste liquid bucket by the second vacuum pump SR55. When the waste cleaning liquid in the dispensing needle 31 is discharged, the dispensing needle 31 first discharges the waste cleaning liquid into the cleaning pool 35, and the third dispensing control valve V813 then disconnects the first dispensing liquid discharge pipeline 814 from the second vacuum pump SR55 and communicates the second dispensing liquid discharge pipeline 815 with the second vacuum pump SR55. In this case, the cleaning liquid in the cleaning pool 35 can be discharged into the waste liquid bucket by the second vacuum pump SR55.

Figure 11:
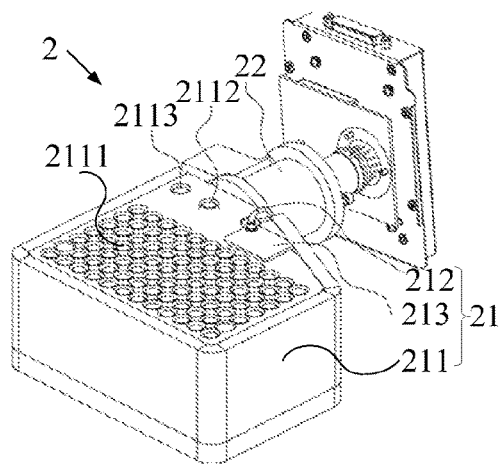
FIG. 11 is a schematic view of an incubation and luminescence detection device in the fully automated chemiluminescence immunoassay analyzer shown in FIG. 1.
Figure 12:
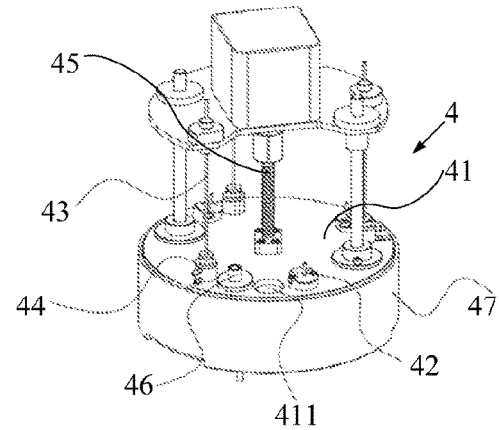
FIG. 12 is a schematic view of a magnetic separation cleaning device in the fully automated chemiluminescence immunoassay analyzer shown in FIG. 1.
Figure 13:
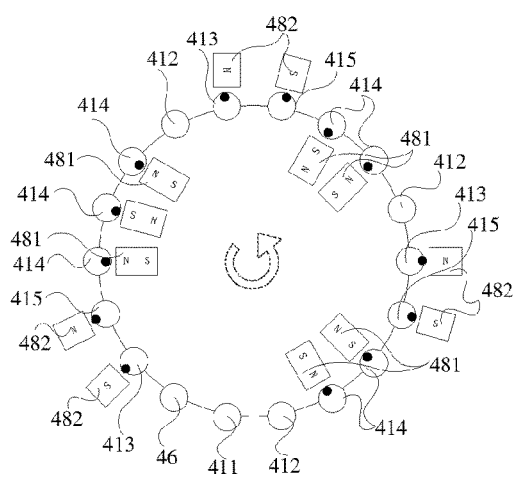
FIG. 13 is a schematic view of a station on a magnetic separation base in the magnetic separation cleaning device shown in FIG. 12.

Referring to FIGS. 1 and 11, as an implementable way, the incubation and luminescence detection device 2 comprises a sample incubation mechanism 21 and a luminescence detection member 22. Particularly, the sample incubation mechanism 21 of the incubation and luminescence detection device 2 comprises an incubation block 211, the luminescence detection member 22 is provided at a rear side face of the incubation block 211, and the reaction vessel subjected to the incubation is detected by the luminescence detection member 22. The sample incubation mechanism 21 can perform an incubation operation on the reaction vessel transferred thereto, such that the mixture in the reaction vessel ca fully react to form an analyte and impurities. The luminescence detection member 22 is configured to perform luminescence detection on the analyte in the reaction vessel. The reaction vessel from which the impurities are removed by the magnetic separation cleaning device 4 is then transferred back to the incubation block 211 by the reaction vessel grasping device 5, and luminescence detection is performed on the analyte by the luminescence detection member 22.

It can be understood that if a substrate needs to be added, the substrate is added to the reaction vessel subjected to the magnetic separation cleaning in the magnetic separation cleaning device 4, and the reaction vessel is then transferred back to the incubation block 211 by the reaction vessel grasping device 5. If the analyte and the substrate need to be mixed, the reaction vessel grasping device 5 transfers the reaction vessel from the magnetic separation cleaning device 4 into the substrate mixing seat 63 of the mixing device 6. After the mixing, the reaction vessel grasping device 5 then transfers the reaction vessel from the substrate mixing seat 63 of the mixing device 6 back to the incubation block 211; and the analyte to which the substrate is added needs to be incubated again before performing the luminescence detection thereon by the luminescence detection member 22.

In addition, the luminescence detection member 22 is provided on the incubation block 211, that is, the incubation function and the detection function are integrated, this can make the whole machine have a compact structure and reduce the volume thereof, and can also shorten the transfer path of the reaction vessel, thereby increasing the operation efficiency of the whole machine. Moreover, the luminescence detection member 22 is located at the rear side face of the sample incubation mechanism 21 and arranged side by side with the magnetic separation cleaning device 4, this can reduce the occupied space and increase the space utilization rate, thereby reducing the overall volume.

The sample incubation mechanism 21 further comprises a heating component provided below the incubation block 211. The heating component is configured to heat the incubation block 211. The incubation block 211 is provided with a plurality of incubation holes 2111 arranged in an array. The incubation hole 2111 is configured to receive the reaction vessel and performs the incubation operation. The heating component can heat the incubation block 211, and the incubation block 211 can carry the reaction vessel and heat the mixture in the reaction vessel to realize the incubation function. The heating component can heat the mixture in the reaction vessel to a preset temperature such as about 34° C. before formal measurement, to ensure that the reaction proceeds normally. Moreover, the plurality of incubation holes 2111 may be arranged in any manner. In this embodiment, the arrangement of the plurality of incubation holes 2111 in an array can increase the number of reaction vessels carried by the incubation block 211. As an example, the incubation block 211 has a metal structure. In this way, it is possible to facilitate heat dissipation, thereby facilitating the heating of the reaction vessel in the incubation block 211. The heating component is a heating film. The heating film can generate heat after being energized, and the heat can heat the incubation block 211. Of course, in other implementations of the present disclosure, the heating component may also be a heating wire, a heating rod, or other structures capable of heating. Moreover, the luminescence detection member 22 is located at a side face of the incubation block 211, which facilitates the combination of the luminescence detection member 22 and the sample incubation mechanism 21 and also facilitates the luminescence detection member 22 in performing the luminescence detection on the reaction vessel.

It can be understood that the incubation of the mixture in the reaction vessel needs to take a certain amount of time, and the reaction vessel grasping device 5 can transfer the reaction vessel where uniform mixing has performed by the reagent and sample mixing seat 62 of the mixing seat into the incubation hole 2111 of the incubation block 211. Since the devices of the fully automated chemiluminescence immunoassay analyzer of the present disclosure simultaneously move so that the reaction vessels are operated at various positions, the reaction vessel grasping device 5 can perform other operations without waiting for the completion of the incubation in the reaction vessel, such as transferring the reaction vessel to the reagent and sample mixing seat 62, transferring the reaction vessel from the magnetic separation cleaning device 4 to the substrate mixing seat 63, or transferring the reaction vessel where the incubation is completed to the magnetic separation cleaning device 4.

Optionally, the sample incubation mechanism 21 further comprises a temperature sensor. The temperature sensor is provided on the incubation block 211 for detecting the temperature of the incubation block 211 and controlling the heating temperature of the heating component for the incubation block 211. The temperature sensor is electrically connected to the main control device 77. The main control device 77 can further detect the temperature of the incubation block 211 via the temperature sensor, and also controls the heating component to heat the incubation block 211 via the temperature sensor, and adjusts the heating temperature of the heating component for the incubation block 211. Particularly, the temperature sensor controls the output power of the heating component by detecting the temperature of the incubation block 211 to perform overall temperature control over the incubation block 211. If the temperature sensor detects that the temperature of the incubation block 211 is low, the temperature sensor controls the heating component to perform heating, to increase the temperature of the incubation block 211. If the temperature of the incubation block 211 is high, the temperature sensor controls the heating component to stop heating.

Still optionally, the sample incubation mechanism 21 further comprises a temperature switch. The temperature switch is provided on the incubation block 211, and the temperature switch is configured to control the heating component to stop heating. The temperature switch is electrically connected to the heating component, and the temperature control switch is also electrically connected to the main control device 77. When the temperature control function of the temperature sensor fails, the main control device 77 controls the temperature switch to cut off a power supply of the heating component to achieve high-temperature protection, avoiding the failure of the sample in the reaction vessel caused by high temperature, and ensuring the accurate detection result of the sample.

Further, the incubation block 211 is further provided with a luminescence detection hole 2112. The luminescence detection hole 2112 is provided corresponding to the luminescence detection member 22, and is located on the side away from the incubation hole 2111. The reaction vessel subjected to the incubation is transferred from the incubation hole 2111 into the luminescence detection hole 2112, and the luminescence detection member 22 performs the luminescence detection on the reaction vessel. Particularly, the incubation block 211 is further provided with a luminescence detection opening, which communicates the incubation hole 2111 with the luminescence detection member 22. During the detection, the reaction vessel grasping device 5 transfers the reaction vessel into the luminescence detection hole 2112, and the luminescence detection member 22 detects the luminescence value of the analyte in the reaction vessel, and the light emitted by the reaction vessel can be irradiated to the luminescence detection member 22 through the luminescence detection opening, so that the luminescence detection of the analyte in the reaction vessel is realized. As an example, the luminescence detection hole 2112 is located at the position of an edge of the incubation hole 2111, which is convenient for the luminescence detection member 22 to perform the luminescence detection.

It can be understood that, if there is no need to add a substrate to the analyte, the reaction vessel grasping device 5 directly transfers the reaction vessel subjected to the magnetic separation cleaning from the magnetic separation cleaning device 4 into the luminescence detection hole 2112 of the incubation block 211. If there is no need to perform mixing after the substrate is added to the analyte, the reaction vessel grasping device 5 directly transfers the reaction vessel subjected to the magnetic separation cleaning from the magnetic separation cleaning device 4 into the incubation hole 2111 of the incubation block 211. After the incubation operation is performed by the incubation block 211 on the reaction vessel, the reaction vessel grasping device 5 transfers the reaction vessel from the incubation hole 2111 into the luminescence detection hole 2112. If there is a need to perform mixing after the substrate is added to the analyte, the reaction vessel grasping device 5 first transfers the reaction vessel subjected to the magnetic separation cleaning from the magnetic separation cleaning device 4 into the substrate mixing seat 63 of the mixing device 6, such that the analyte and the substrate in the reaction vessel are mixed uniformly, the reaction vessel grasping device 5 then transfers the reaction vessel from the substrate mixing seat 63 into the incubation hole 2111 of the incubation block 211, and after the incubation operation is performed by the incubation block 211 on the reaction vessel, the reaction vessel grasping device 5 transfers the reaction vessel from the incubation hole 2111 into the luminescence detection hole 2112.

As an implementable way, the fully automated chemiluminescence immunoassay analyzer further comprises a waste liquid discharge device 7. the waste liquid discharge device 7 is movably provided on the left side of the incubation block 211. the waste liquid discharge device 7 is configured to discharge the waste liquid from the reaction vessel subjected to the detection. the waste liquid discharge device 7 can also shield, while discharging the waste liquid, the reaction vessel that is being subjected to luminescence detection in the incubation and luminescence detection device 2.

Further, the incubation block 211 is further provided with a waste liquid discharge hole 2113. the waste liquid discharge hole 2113 is arranged side by side with and adjacent to the luminescence detection hole 2112, and the reaction vessel in the luminescence detection hole 2112 is shielded when the waste liquid discharge device 7 descends to discharge the waste liquid from the reaction vessel. the waste liquid discharge hole 2113 is separately provided, the reaction vessel subjected to the detection and having the waste liquid to be discharged can be transferred into the waste liquid discharge hole 2113, and a reaction vessel where detection is to be performed is then transferred into the luminescence detection hole 2112, such that the luminescence detection process and the waste liquid discharge process can be carried out at the same time to prevent the reaction vessel having the waste liquid to be discharged from occupying the luminescence detection hole 2112 to affect the detection, and improve the operation efficiency of the whole machine. moreover, the waste liquid discharge device 7 can discharge the waste liquid from the reaction vessel. particularly, when the waste liquid discharge device 7 descends, the waste liquid discharge device 7 can extend into the reaction vessel at the waste liquid discharging hole 2113, and the waste liquid in the reaction vessel is discharged. after the discharging of the waste liquid is completed, the waste liquid discharge device 7 ascends and is restored. in this way, the reaction vessel, from which the waste liquid is discharged, is discarded into the waste box 99 by the reaction vessel grasping device 5, so that it is possible to avoid the problems of pollution and affecting the environment caused by the turbulent flow of the waste liquid. moreover, the waste liquid discharge hole 2113 and the luminescence detection hole 2112 are arranged adjacent to each other. this can reduce the transfer path of the reaction vessel and improve the transfer efficiency of the reaction vessel grasping device 5, and can also make the overall structure compact and small.

Moreover, the waste liquid discharge device 7 can also have a shielding function. the waste liquid discharge device 7 descends while discharging the waste liquid, this can block the luminescence detection hole 2112, so as to shield the reaction vessel in the luminescence detection hole 2112, thereby improving the accuracy of the luminescence detection member 22 in detecting the sample, after the reaction vessel is transferred to the luminescence detection hole 2112, the waste liquid discharge device 7 descends and can cover the reaction vessel at the shielded hole, to prevent the external light source from irradiating the analyte through the luminescence detection hole 2112. in this way, the luminescence value detected by the luminescence detection member 22 is only the luminescence value of the analyte, such that the luminescence detection member 22 will not detect the light in the outside environment, ensuring accurate and reliable sample detection results.

The reaction vessel subjected to the detection can be transferred from the luminescence detection hole 2112 to the waste liquid discharge hole 2113 by the reaction vessel grasping device 5, and the reaction vessel grasping device 5 further transfers the reaction vessel where detection is to be performed from the incubation hole 2111 to the luminescence detection hole 2112. thereafter, the waste liquid discharge device 7 descends, such that the waste liquid discharge device 7 extends into the reaction vessel of the waste liquid discharge hole 2113, and the waste liquid discharge device 7 can also cover the reaction vessel at the luminescence detection hole 2112. the luminescence detection hole 2112 can also be shield while the waste liquid discharge device 7 moving up and down to discharge the waste liquid. in this way, when controlling the waste liquid discharge device 7 to aspirate the waste liquid from the reaction vessel, the main control device 77 can also control the luminescence detection member 22 to detect the luminescence value of the analyte within the reaction vessel in the luminescence detection member hole 2112. in this way, it is possible to improve the operation efficiency of the whole machine. it should be noted that the waste liquid discharged by the waste liquid discharge device 7 is discharged into the waste liquid bucket via the liquid path device 8, which will be described in detail later.

Of course, in other implementations of the present disclosure, it is also possible to use only one luminescence detection hole 2112. Particularly, the reaction vessel is transferred into the luminescence detection hole 2112, the waste liquid discharge device 7 descends to block the reaction vessel at the luminescence detection hole 2112, and after the luminescence detection member 22 performs the luminescence detection, the waste liquid discharge device 7 discharges the waste liquid from the reaction vessel.

As an example, the waste liquid discharge device 7 comprises an ascending/descending slider component, a waste liquid discharge needle, and a shading cover. The ascending/descending slider component is movably arranged, and the waste liquid discharge needle and the shading cover are both arranged on the ascending/descending slider component. The ascending/descending slider component can drive the waste liquid discharge needle and the shading cover to ascend or descend synchronously. When the ascending/descending slider component drives the waste liquid discharge needle and the shading cover to descend simultaneously, the waste liquid discharge needle can enter into the reaction vessel at the waste liquid discharge hole 2113, and at the same time, the shading cover covers the reaction vessel at the luminescence detection hole 2112. Preferably, the shading cover has a structure similar to a bucket cover. The incubation block 211 is provided with a snap-in groove at the shaded hole. An edge of the shading cover can be snapped into the snap-in groove to ensure the shading reliability and therefore the reliability of the detection of the sample.

Optionally, the sample incubation mechanism 21 further comprises a substrate heat-conducting structure 212. The substrate heat-conducting structure 212 is configured to preheat the substrate, so as to facilitate the reaction between the substrate and the analyte, and to facilitate the incubation block 211 in performing the incubation operation on the substrate and the analyte in the subsequent reaction vessel, shortening the preheating time and increasing the processing speed. The substrate heat-conducting structure 212 comprises a substrate preheating tube and a substrate heat-conducting block. The substrate preheating tube and the substrate heat-conducting block are both provided in the incubation block 211. The substrate heat-conducting block is configured to heat the substrate in the substrate preheating tube. The use of a substrate preheating tube can ensure the performance of the substrate, avoiding the failure of the substrate affecting the detection accuracy of the sample. The substrate heat-conducting block has the characteristic of fast heat conduction, and can quickly transfer the heat from the incubation block 211 to the substrate preheating tube to heat the substrate. In this embodiment, the substrate preheating tube may be a non-metal tube or a metal tube. Preferably, the substrate preheating tube is wound around the substrate heat-conducting block in a spiral manner to realize the heating of the substrate in the substrate preheating tube. This can increase the contact area and ensure the heating effect. Of course, in other implementations of the present disclosure, the incubation block 211 may also be used directly to heat the substrate preheating tube, that is, there is no need to use a substrate heat-conducting block.

Still optionally, the sample incubation mechanism 21 further comprises a cleaning liquid preheating container 213. The cleaning liquid preheating container 213 can heat the cleaning liquid to avoid the temperature drop of the analyte, so as to facilitate the reaction of the analyte, and to facilitate the incubation block 211 in performing the incubation operation on the substrate and the analyte in the subsequent reaction vessel, shortening the preheating time and increasing the processing speed. The cleaning liquid preheating container 213 is provided in the incubation block 211 for heating the cleaning liquid, and can deliver the heated cleaning liquid into the reaction vessel. The cleaning liquid preheating container 213 is heated by the incubation block 211, to heat the cleaning liquid in the cleaning liquid preheating container 213. The cleaning liquid heated by the separation preheating container 213 is delivered into the magnetic separation cleaning device 4 to clean the analyte and the impurities in the reaction vessel and remove the impurities.

In principle, the positions of the waste liquid discharge hole 2113, the luminescence detection hole 2112 and the incubation holes 2111 are not limited, as long as they can achieve the corresponding functions. In this embodiment, the incubation holes 2111 distributed in an array are located on the front side of the incubation block 211, and the waste liquid discharge hole 2113 and the luminescence detection hole 2112 are located on the rear side of the reaction vessel. Correspondingly, the luminescence detection member 22 is arranged on the rear side of the incubation block 211. Moreover, the substrate heat-conducting structure 212 and the cleaning liquid preheating container 213 are also located on the rear side of the incubation block 211.

In addition to integrating the incubation function and the luminescence detection function, the incubation and luminescence detection device 2 of the present disclosure also has the waste liquid discharge function, so that the incubation and luminescence detection device 2 has a compact structure. Moreover, the cooperation of the incubation block 211 with the substrate heat-conducting structure 212 and the cleaning liquid preheating container 213 can make full use of thermal energy from the incubation block 211, reducing the number of heating devices required on the fully automated chemiluminescence immunoassay analyzer, and realizing the integration of multiple temperature control functions on only one heating device, so that the functions of sample incubation, substrate incubation, substrate preheating, and cleaning liquid preheating are realized; and through the cooperation of the incubation block 211 and the luminescence detection member 22, the luminescence detection function is realized. The use of the incubation and luminescence detection device 2 can make the fully automated chemiluminescence immunoassay analyzer of the present disclosure have the characteristics of simple structure, small size, low costs, energy-saving and environment-friendly, and safe.

Referring to FIGS. 1, 12, 13 and 15, as an implementable way, the magnetic separation cleaning device 4 is a disc-shaped structure, comprising a magnetic separation base 41, a cleaning liquid injection mechanism 42, a cleaning liquid discharge mechanism 43 and a magnetic separation attraction mechanism 48. The magnetic separation base has a carrying function, and is configured to carry various components of the magnetic separation cleaning device 4, and the magnetic separation base 41 can also carry the reaction vessel to be cleaned. The reaction vessel grasping device 5 transfers the reaction vessel from the incubation and luminescence detection device 2 onto the magnetic separation base 41, and after cleaning by the magnetic separation cleaning device 4, the reaction vessel grasping device 5 transfers the reaction vessel away from the magnetic separation base 41. If the substrate is added, after the substrate is added to the magnetic separation base 41 (the substrate here is heated by the incubation block 211), the reaction vessel grasping device 5 then transfers the reaction vessel away from the magnetic separation base 41. The cleaning liquid injection mechanism 42 is connected to the liquid path device 8, and can inject the cleaning liquid (the cleaning liquid here is heated by the incubation block 211) into the reaction vessel at the magnetic separation base 41. The cleaning liquid discharge mechanism 43 is connected to the liquid path device 8 and can discharge the waste cleaning liquid in the reaction vessel at the magnetic separation base 41 and the cleaning liquid after performing the cleaning. It can be understood that the step of injecting the cleaning liquid by the cleaning liquid injection mechanism 42 is performed before the cleaning liquid discharge mechanism 43 discharges the cleaning liquid. Moreover, the cleaning liquid injection mechanism 42 and the cleaning liquid discharge mechanism 43 are used in pairs.

As an example, the numbers of the cleaning liquid injection mechanisms 42 and the cleaning liquid discharge mechanisms 43 are both plural. In this embodiment, the numbers of the cleaning liquid injection mechanisms 42 and the cleaning liquid discharge mechanisms 43 are both three. The three cleaning liquid injection mechanisms 42 and the three cleaning liquid discharge mechanisms 43 are alternately distributed on the magnetic separation base 41, that is, the cleaning liquid injection mechanisms 42 are respectively provided on two sides of the cleaning liquid discharge mechanism 43, and the cleaning liquid discharge mechanisms 43 are respectively provided on two sides of the cleaning liquid injection mechanism 42. It can be understood that both the delivery and the output of the cleaning liquid are realized by means of the liquid path device 8, which will be described in detail later.

The magnetic separation base 41 is provided with an access hole 411, and a cleaning liquid intake hole 412 and a cleaning liquid discharge hole 413 provided in sequence. The access hole 411 is configured to place or remove a reaction vessel to be separated. The magnetic separation base 41 drives the reaction vessel to rotate such that the reaction vessel sequentially corresponds to the cleaning liquid intake hole 412, the cleaning liquid discharge hole 413 and the access hole 411. The cleaning liquid injection mechanism 42 is provided in the cleaning liquid intake hole 412 for adding the cleaning liquid into the reaction vessel. The cleaning liquid discharge mechanism 43 is arranged in a liftable manner corresponding to the cleaning liquid discharge hole 413, for discharging the waste cleaning liquid from the reaction vessel. The reaction vessel grasping device 5 places the reaction vessel from the incubation block 211 into the magnetic separation base 41 through the access hole 411, and the magnetic separation base 41 drives the reaction vessel to rotate from the access hole 411 to the cleaning liquid intake hole 412. The cleaning liquid injection mechanism 42 adds into the reaction vessel through the cleaning liquid intake hole 412, the magnetic separation base 41 then drives the reaction vessel from the cleaning liquid discharge hole 413, and the cleaning liquid discharge mechanism 43 discharges the waste cleaning liquid from the reaction vessel through the cleaning liquid discharge hole 413. Finally, the magnetic separation base 41 drives the reaction vessel to rotate from the cleaning liquid discharge hole 413 to the access hole 411, and the reaction vessel grasping device 5 removes the reaction vessel.

It can be understood that after the magnetic separation base 41 drives the reaction vessel to rotate from the access hole 411 to the cleaning liquid intake hole 412, the reaction vessel grasping device 5 can also place the next reaction vessel into the magnetic separation base 41 through the access hole 411 to achieve continuous separation cleaning operations, increasing the operation efficiency of the whole machine. If the numbers of the cleaning liquid injection mechanisms 42 and the cleaning liquid discharge mechanisms 43 are both plural, the numbers of the cleaning liquid intake holes 412 and the cleaning liquid discharge holes 413 are also correspondingly plural. In this case, the magnetic separation base 41 drives the reaction vessel from the access hole 411 through the multiple cleaning liquid intake holes 412 and cleaning liquid discharge holes 413 and then returns to the access hole 411, so as to realize multiple times of separation cleaning of the analytes in the reaction vessel, to further remove the impurities from the reaction vessel and increase the purity of the analyte.

Moreover, the magnetic separation base 41 comprises a magnetic separation pot, a magnetic separation cover plate, a magnetic separation bracket and a magnetic separation driving structure. The magnetic separation bracket is rotatably provided in the magnetic separation pot, and the magnetic separation driving structure drives the magnetic separation bracket to rotate in the magnetic separation pot. The magnetic separation cover plate covers the magnetic separation pot. The magnetic separation cover plate has a stationary structure and is fixed on the magnetic separation pot. The magnetic separation bracket is provided with a plurality of apertures for placing the reaction vessels. The plurality of apertures are uniformly distributed on the magnetic separation bracket, and the spacing between adjacent two of the apertures is equal to the spacing between the access hole 411 and the cleaning liquid intake hole 412, and is also equal to the spacing between the cleaning liquid intake hole 412 and the cleaning liquid discharge hole 413.

The access hole 411, the cleaning liquid intake hole 412 and the cleaning liquid discharge hole 413 are provided on the magnetic separation cover plate, and respectively correspond to the apertures on the magnetic separation bracket. It can be understood that the size of the access hole 411 is larger than the maximum outer diameter of the reaction vessel. The reaction vessel gripping device 5 can receive the reaction vessel on the magnetic separation bracket through the access hole 411. After the placement is completed, the top of the reaction vessel will not be exposed out of the magnetic separation cover plate. The magnetic separation driving structure drives the magnetic separation bracket to rotate in the magnetic separation pot, can drive the reaction vessel to rotate below the magnetic separation cover plate, and respectively correspond to the cleaning liquid intake hole 412 and the cleaning liquid discharge hole 413. As an example, the magnetic separation driving structure may be a structure of a motor cooperating with a synchronous belt, or a gear structure, etc.

One step of rotation of the magnetic separation bracket driven by the magnetic separation driving structure is a test beat. Within the test beat, a reaction vessel originally at the access hole 411 is rotated to the cleaning liquid intake hole 412, a reaction vessel originally at the cleaning liquid intake hole 412 is rotated to the cleaning liquid discharge hole 413, a reaction vessel originally at the cleaning liquid discharge hole 413 is rotated to the access hole 411, the reaction vessel subjected to the separation cleaning is removed from the access hole 411, and a reaction vessel where the separation cleaning are to be performed is placed in through the access hole 411, and at the same time, the cleaning liquid injection mechanism 42 adds the cleaning liquid into the reaction vessel at the cleaning liquid intake hole 412, and the cleaning liquid discharge mechanism 43 discharges the waste cleaning liquid from the reaction vessel at the cleaning liquid discharge hole 413.

Further, the magnetic separation cleaning device 4 further comprises a liquid discharge ascending/descending portion 45 and a magnetic separation swab 44. The cleaning liquid discharge mechanism 43 of the magnetic separation cleaning device 4 comprises a liquid discharge needle. The magnetic separation swab 44 can clean an outer surface of the liquid discharge needle, to prevent the waste cleaning liquid remaining on the outer wall of the liquid discharge needle from polluting the analyte in the next waste cleaning liquid to be discharged, and to ensure the detection accuracy of the sample. Moreover, the provision of the magnetic separation swab 44 can also prevent the liquid discharge needle from being transferred to other cleaning pools 35 for cleaning, thereby improving the liquid discharge efficiency of the liquid discharge needle.

The cleaning liquid discharge mechanism 43 is installed at the liquid discharge ascending/descending portion 45, which is convenient for controlling the cleaning liquid discharge mechanism 43 to descend and discharge the waste cleaning liquid, and to ascend after the cleaning is completed, without affecting the rotation of the magnetic separation bracket. The liquid discharge ascending/descending portion 45 is arranged in a liftable manner on the magnetic separation base 41. The liquid discharge ascending/descending portion 45 is configured to implement the installation of the cleaning liquid discharge mechanism 43, and the ascending and descending movements of the liquid discharge ascending/descending portion 45 can discharge the waste cleaning liquid from the reaction vessel. When the liquid discharge ascending/descending portion 45 descends, the cleaning liquid discharge mechanism 43 extends into the reaction vessel and discharges the waste cleaning liquid. Upon completion, the liquid discharge ascending/descending portion 45 drives the cleaning liquid discharge mechanism 43 to ascend and restore same.

The liquid discharge needle is provided on the liquid discharge ascending/descending portion 45, and the magnetic separation swab 44 is provided in the cleaning liquid discharge hole 413. When the liquid discharge ascending/descending portion 45 drives the liquid discharge needle to descend or ascend, the magnetic separation swab 44 cleans the outer wall of the liquid discharge needle. Particularly, the liquid discharge ascending/descending portion 45 comprises a vertical mounting plate and a vertical ascending/descending movement structure. The vertical mounting plate is provided on the vertical ascending/descending movement structure, and the vertical ascending/descending movement structure is arranged in a liftable manner on the magnetic separation base 41. The vertical ascending/descending movement structure can drive the vertical mounting plate to ascend and descend. It can be understood that the vertical ascending/descending movement structure can adopt a structure of a motor cooperating with a lead screw nut, and can also cooperate with an ascending/descending slider and other structures capable of ascending and descending.

The liquid discharge needle is installed on the vertical mounting plate of the liquid discharge ascending/descending portion 45. When the vertical ascending/descending movement structure drives the vertical mounting plate to ascend and descend, the liquid discharging needle can be simultaneously driven to ascend and descend. Particularly, the vertical ascending/descending movement structure drives the liquid discharge needle to descend via the vertical mounting plate, the liquid discharge needle extends through the magnetic separation swab 44 into the reaction vessel corresponding to the cleaning liquid discharge hole 413, and aspirates the waste cleaning liquid from the reaction vessel, the vertical ascending/descending movement structure then drives the liquid discharge needle to ascend via the vertical mounting plate, and the liquid discharge needle ascends at the magnetic separation swab 44 and gets out of the reaction vessel. The magnetic separation swab 44 can clean the outer wall of the liquid discharge needle during the descending and ascending of the liquid discharge needle. As an example, the cleaning liquid discharge mechanism further comprises a liquid discharge needle mounting seat. The liquid discharge needle mounting seat is mounted on the vertical mounting plate, and the liquid discharge needle is mounted on the liquid discharge needle mounting seat.

It can be understood that the magnetic separation swab 44 is provided with a separation cleaning guide hole, a cleaning liquid cleaning inlet and a cleaning liquid cleaning outlet, and the liquid discharge needle ascends and descends along the separation cleaning guide hole to aspirate the waste cleaning liquid from the reaction vessel. The cleaning liquid cleaning inlet and the cleaning liquid cleaning outlet are respectively in communication with the liquid path device 8 to realize the delivery and output of the cleaning liquid. The cleaning liquid enters the magnetic separation swab 44 from the cleaning liquid cleaning inlet, and comes into contact with the liquid discharge needle in the separation cleaning guide hole to clean the outer wall of the liquid discharge needle. After the cleaning is completed, the waste cleaning liquid passes through the cleaning liquid cleaning outlet and is discharged into the waste liquid bucket through the liquid path device 8.

Still further, the cleaning liquid injection mechanism 42 of the magnetic separation cleaning device 4 comprises a liquid injection needle and a liquid injection needle seat. The liquid injection needle seat is fixed to the cleaning liquid intake hole 412. The liquid injection needle is connected to the liquid path device 8, and is provided on the liquid injection needle seat. The liquid injection needle is configured to add the cleaning liquid into the reaction vessel. The tail of the liquid injection needle is connected to the liquid path device 8 to deliver the cleaning liquid to the liquid injection needle, such that the cleaning liquid is delivered into the reaction vessel by means of the liquid injection needle. Moreover, the inclined angle between the liquid injection needle and the liquid injection needle seat is less than 90°, such that the cleaning liquid is also added into the reaction vessel in an inclined manner, and the cleaning liquid can be directly injected onto a side wall of the reaction vessel, to effectively wash away magnetic beads on the side wall of the reaction vessel to reduce the residual amount of impurities such as enzymes.

Preferably, the magnetic separation cleaning device 4 further comprises a magnetic shielding component 47. The magnetic shielding component 47 is sleeved outside the magnetic separation base 41 for shielding a magnetic field generated by the magnetic separation attraction mechanism 48. Since a magnet that attracts the magnetic beads has a high magnetic field strength, the magnetic field generated by the magnet will affect the accuracy and reliability of the luminescence detection of the luminescence detection member 22 (generally a photomultiplier tube (PMT)). In the fully automated chemiluminescence immunoassay analyzer of the present disclosure, in order to reduce the influence of the magnetic field on the luminescence detection of the luminescence detection member 22, a cylindrical barrel of a magnetic material is designed at an outer periphery of the magnetic separation base 41 as the magnetic shielding component 47. The magnetic shielding component 47 is sleeved outside the magnetic separation base 41. Of course, the magnetic shielding component is not limited to a cylindrical barrel shape, but may also be square or polygonal. The magnetic shielding component 47 enables the magnetic separation cleaning device 4 to be placed close to the luminescence detection member 22 on the premise of preventing the magnetic field from affecting the detection performance of the luminescence detection member 22, thereby reducing the volume of the analyzer. In this embodiment, the magnetic separation cleaning device 4 may be arranged side by side with the luminescence detection member 22.

In another implementation not shown, the magnetic shielding component 47 may be configured as a magnetic shielding partition provided between the magnetic separation cleaning device 4 and the luminescence detection member 22, such that the magnetic separation cleaning device 4 can be placed close to the luminescence detection member 22, thereby reducing the volume of the analyzer. Of course, those skilled in the art can understand that, compared to this implementation, the above implementation in which a cylindrical barrel of a magnetic material is designed at an outer periphery of the magnetic separation base 41 as the magnetic shielding component can better shield the magnetic field generated by the magnetic separation attraction mechanism 48.

In another implementation not shown, an upper end face 471 of a shielding cover member 47 is higher than an upper end face 483 of a magnet 48, and especially the upper end face of the shielding cover member 47 away from the luminescence detection member 22 is higher than the upper end face of the magnet, so as to prevent the magnetic field of the magnet from escaping the shielding barrel and interfering with the luminescence detection member 22.

Optionally, the magnetic separation base 41 is further provided with a substrate injection hole 46. The substrate injection hole 46 is located between the access hole 411 and the cleaning liquid discharge hole 413. One extended end of the liquid path device 8 extends into the substrate injection hole 46. The substrate can be added into the reaction vessel through the substrate injection hole 46. That is to say, the substrate is also added at the magnetic separation cleaning device 4. In this way, it is possible to reduce the need to separately provide a substrate adding mechanism, thereby reducing the overall volume. Here, one extended end of the liquid path device 8 refers to one end of a substrate discharge pipeline 822 of a substrate delivery liquid path system 82 of the liquid path device 8. The substrate delivery liquid path system 82 of the liquid path device 8 is in communication with the substrate injection hole 46 and adds the substrate into the reaction vessel through the substrate injection hole 46. It can be understood that the magnetic separation cleaning device 4 further comprises a substrate injection mechanism. The substrate injection mechanism is provided in the substrate injection hole 46. The substrate injection mechanism is connected to the substrate discharge pipeline 822 of the substrate delivery liquid path system 82 to add the substrate into the reaction vessel. The substrate injection mechanism comprises an injection tube and a tube seat. The tube seat is provided in the substrate injection hole 46, and one end of the injection tube is connected to the substrate discharge pipe 822 of the substrate injection mechanism.

Figure 14:
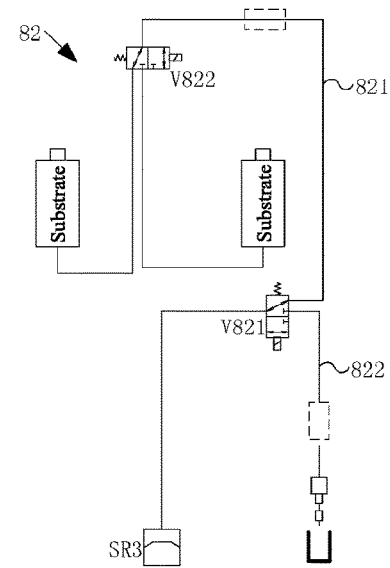
FIG. 14 is a schematic view of a liquid path of a substrate delivery liquid path system in a liquid path device according to an embodiment of the present disclosure.

Referring to FIGS. 1 and 14, as an implementable way, the fully automated chemiluminescence immunoassay analyzer further comprises two substrate receiving portions. The substrate receiving portion is located on the front side of the sample and reagent receiving device 1, is configured to carry a substrate vessel, and delivers the substrate in the substrate vessel, after being preheated by a substrate preheating tube through a pipeline, into the reaction vessel through the substrate injection hole 46. Particularly, the substrate receiving portion is provided on the right front side of the carrying platform, such that after the substrate receiving portion loads the substrate vessel, the substrate vessel can be brought close to the user, which is convenient for the user to replace the substrate vessel, and the substrate vessel is introduced to the substrate preheating tube, and the substrate injection hole through the pipeline, realizing the delivery of the substrate.

Particularly, the fully automated chemiluminescence immunoassay analyzer further comprises a substrate fixed-displacement pump SR3. The substrate fixed-displacement pump SR3 is located on the carrying platform and provided on the front side of the sample and reagent receiving device 1. The substrate fixed-displacement pump SR3 is respectively in communication with the substrate vessel, the substrate preheating tube and the substrate injection hole 46 through pipelines, and provides power for the delivery of the substrate.

Particularly, the liquid path device 8 comprises a substrate delivery liquid path system 82. The substrate delivery liquid path system 82 is configured to deliver the substrate to the magnetic separation cleaning device 4, and the substrate is delivered into the reaction vessel subjected to the cleaning by means of the magnetic separation cleaning device 4. The substrate delivery liquid path system 82 comprises a substrate aspiration pipeline 821, a substrate discharge pipeline 822, and a first substrate control valve V821. The substrate fixed-displacement pump SR3 is connected to the substrate aspiration pipeline 821 and the substrate discharge pipeline 822 via the first substrate control valve V821, and used to aspirate a predetermined amount of substrate from a substrate vessel and add the substrate into the reaction vessel.

It can be understood that one end of the substrate aspiration pipeline 821 extends into the substrate vessel, and the other end of the substrate aspiration pipeline 821 is connected to the substrate fixed-displacement pump SR3 via the first substrate control valve V821. The substrate fixed-displacement pump SR3 is also connected to one end of the substrate discharge pipeline 822 via the first substrate control valve V821, and the other end of the substrate discharge pipeline 822 is connected to the magnetic separation cleaning device 4. The first substrate control valve V821 communicates the substrate fixed-displacement pump SR3 with the substrate aspiration pipeline 821 while disconnecting the substrate fixed-displacement pump SR3 from the substrate discharge pipeline 822. In this case, the substrate fixed-displacement pump SR3 aspirates the cleaning liquid from the substrate vessel via the substrate aspiration pipeline 821. The first substrate control valve V821 then disconnects the substrate fixed-displacement pump SR3 from the substrate aspiration pipeline 821 while communicating the substrate fixed-displacement pump SR3 with the substrate discharge pipeline 822. In this case, the substrate fixed-displacement pump SR3 can deliver the aspirated substrate into the magnetic separation cleaning device 4 through the substrate discharge pipeline 822, and then deliver the substrate into the reaction vessel subjected to the separation cleaning by means of the magnetic separation cleaning device 4. It can be understood that the control valve in the present disclosure may adopt a two-position three-way valve, a multi-position multi-way valve, or a three-way valve cooperating with two switch valves, etc., to control the opening and closing.

Further, the substrate delivery liquid path system 82 further comprises a second substrate control valve V822. The second substrate control valve V822 is provided on the substrate aspiration pipeline 821 for aspirating the substrate from at least two substrate vessels. In this embodiment, the number of the substrate vessels is two. Correspondingly, the substrate aspiration pipeline 821 is provided with two substrate aspiration branch pipes. One end of each of the two substrate aspiration branch pipes is respectively connected to the substrate aspiration pipeline 821 via the second substrate control valve V822, the other end of each of the two substrate aspiration branch pipes extends into the corresponding substrate vessel, and the second substrate control valve V822 disconnects one of the substrate aspiration branch pipes from the substrate aspiration pipeline 821 while communicating the other substrate aspiration branch pipe with the substrate aspiration pipeline 821. The position of the second substrate control valve V822 can be controlled to realize the switching of the substrate aspiration pipeline 821 between the two substrate vessels. Of course, it is also possible to use only the substrate in one substrate vessel, and when being used up, the second substrate control valve V822 is switched to add the substrate into the empty substrate vessel.

Moreover, the substrate preheating tube is provided on the substrate discharge pipeline 822. Preferably, the substrate preheating tube is a part of the substrate discharge pipeline 822 to heat the substrate delivered into the magnetic separation cleaning device 4. Of course, in other implementations of the present disclosure, the substrate preheating tube is a fixed part of the incubation block 211, and two ends of the substrate preheating tube are connected to the substrate via the substrate discharge pipeline 822.

Referring to FIGS. 1, 12, 13, and 17 to 19, as an implementable way, the fully automated chemiluminescence immunoassay analyzer further comprises a magnetic separation syringe SR4. The magnetic separation syringe SR4 is located below the carrying platform. Particularly, the magnetic separation syringe SR4 is located on the left side of the carrying platform (particularly, at a slightly rearward position on the left side of the carrying platform). The magnetic separation syringe SR4 is connected to the liquid injection needle via a pipeline to deliver the cleaning liquid into the reaction vessel, and the magnetic separation syringe SR4 is also connected to the magnetic separation swab 44 via a pipeline to supply the cleaning solution to the magnetic separation swab 44.

Particularly, the liquid path device 8 further comprises a magnetic separation cleaning liquid path system 83. The magnetic separation cleaning liquid path system 83 is configured to realize the delivery of the cleaning liquid in the magnetic separation cleaning device 4 and the discharge of the waste cleaning liquid. Particularly, the magnetic separation cleaning liquid path system 83 comprises a magnetic separation liquid aspiration pipeline 831, a magnetic separation liquid injection pipeline 832, and a first magnetic separation control valve V831. The magnetic separation syringe SR4 is respectively in communication with the magnetic separation liquid aspiration pipeline 831 and the magnetic separation liquid injection pipeline 832 through the first magnetic separation control valve V831. The magnetic separation liquid aspiration pipeline 831 is in communication with the cleaning liquid container with the cleaning liquid. The magnetic separation liquid injection pipeline 832 is connected to the liquid injection needle. The first magnetic separation control valve V831 communicates the magnetic separation syringe SR4 with the magnetic separation liquid aspiration pipeline 831, disconnects the magnetic separation syringe SR4 from the magnetic separation liquid injection pipeline 832, and can aspirate the cleaning liquid from the magnetic separation container. The first magnetic separation control valve V831 communicates the magnetic separation syringe SR4 with the magnetic separation liquid injection pipeline 832, disconnects the magnetic separation syringe SR4 from the magnetic separation liquid aspiration pipeline 831, and can inject the cleaning liquid into the reaction vessel.

The magnetic separation syringe SR4 is a power source for the aspiration and discharge of the cleaning liquid. As an example, the magnetic separation syringe SR4 is a syringe, a fixed-displacement pump, or another power source structure. One end of the first magnetic separation control valve V831 is connected to the magnetic separation syringe SR4, and the other two ends of the first magnetic separation control valve V831 are respectively connected to one end of the magnetic separation liquid aspiration pipeline 831 and one end of the magnetic separation liquid injection pipeline 832. The other end of the magnetic separation liquid aspiration pipeline 831 extends into the cleaning liquid container, and the other end of the magnetic separation liquid injection pipeline 832 is connected to the liquid injection needle. When the cleaning liquid is aspirated, the first magnetic separation control valve V831 disconnects the magnetic separation syringe SR4 from the magnetic separation liquid injection pipeline 832 while communicating the magnetic separation syringe SR4 with the magnetic separation liquid aspiration pipeline 831. In this case, the cleaning liquid in the cleaning liquid container can be aspirated by the magnetic separation syringe SR4 and stored in the magnetic separation syringe SR4. When the cleaning liquid is added into the reaction vessel, the first magnetic separation control valve V831 communicates the magnetic separation syringe SR4 with the magnetic separation liquid injection pipeline 832 while disconnecting the magnetic separation syringe SR4 from the magnetic separation liquid aspiration pipeline 831. In this case, the magnetic separation syringe SR4 can add the aspirated cleaning liquid into the reaction vessel through the liquid injection needle. The cleaning liquid is aspirated from the cleaning liquid container and added into the reaction vessel.

The magnetic separation cleaning liquid path system 83 can also deliver the cleaning liquid to the magnetic separation swab 44. Further, the magnetic separation cleaning liquid path system 83 further comprises a first magnetic separation cleaning pipeline 834, a third magnetic separation control valve V833 and a fourth magnetic separation control valve V834. The first magnetic separation cleaning pipeline 834 is connected to the magnetic separation liquid injection pipeline 832 and the magnetic separation swab 44. The third magnetic separation control valve V833 is provided on the first magnetic separation cleaning pipeline 834 for controlling the opening and closing of the first magnetic separation cleaning pipeline 834. The fourth magnetic separation control valve V834 is provided on the magnetic separation liquid injection pipeline 832. The magnetic separation syringe SR4 is in communication with the first magnetic separation cleaning pipeline 834 via the magnetic separation liquid injection pipeline 832. The fourth magnetic separation control valve V834 closes the magnetic separation liquid injection pipeline 832 to clean the outer wall of the liquid injection needle.

Particularly, one end of the first magnetic separation cleaning pipeline 834 is connected to the magnetic separation liquid injection pipeline 832, and the other end of the first magnetic separation cleaning pipeline 834 is connected to the cleaning liquid cleaning inlet of the magnetic separation swab 44. The third magnetic separation control valve V833 is provided on the first magnetic separation cleaning pipeline 834 for controlling the opening and closing of the first magnetic separation cleaning pipeline 834. Moreover, the fourth magnetic separation control valve V834 is provided on the magnetic separation liquid injection pipeline 832 for controlling the opening and closing of the magnetic separation liquid injection pipeline 832. When the cleaning liquid is delivered to the magnetic separation swab 44, the fourth magnetic separation control valve V834 closes the separation liquid injection pipeline, the third magnetic separation control valve V833 opens the first magnetic separation cleaning pipeline 834, and the cleaning liquid syringe causes the aspirated cleaning liquid to enter the first magnetic separation cleaning pipeline 834 through the cleaning liquid injection pipeline and then enter the magnetic separation swab 44 through the cleaning liquid cleaning inlet, to clean an outer surface of the cleaning liquid injection needle. When the cleaning liquid is injected into the reaction vessel, the third magnetic separation control valve V833 closes the first magnetic separation cleaning pipeline 834, and the fourth magnetic separation control valve V834 opens the separation liquid injection pipeline. It can be understood that the position of the fourth magnetic separation control valve V834 on the cleaning liquid injection pipeline is located between the connection between the cleaning liquid injection pipeline and the first divided injection cleaning pipeline 812, and the connection between the cleaning liquid injection pipeline and the liquid injection needle. In this way, it is possible to enable the cleaning liquid aspirated by the syringe to flow into the corresponding vessel, avoiding turbulent flow affecting the reliability of the detection of the sample.

Moreover, the magnetic separation cleaning liquid path system 83 can also discharge the waste cleaning liquid from the magnetic separation cleaning device 4, particularly the waste cleaning liquid from the reaction vessel. Particularly, the fully automated chemiluminescence immunoassay analyzer further comprises a vacuum chamber SR51 and a first vacuum pump SR53. The vacuum chamber SR51 and the first vacuum pump SR53 are located on the rear side of the carrying platform (particularly, at a slightly leftward position on the rear side of the carrying platform). An outlet of the vacuum chamber SR51 is connected to the first vacuum pump SR53. An inlet of the vacuum chamber SR51 is connected to the magnetic separation cleaning device 4 via a pipeline, and the vacuum chamber SR51 provides power for the discharge of the waste cleaning liquid from the reaction vessel cleaned by the magnetic separation cleaning device 4. The inlet of the vacuum chamber SR51 is also connected to the incubation and luminescence detection device 2 via a pipeline, and the vacuum chamber SR51 provides power for the discharge of the waste liquid after the incubation and luminescence detection device 2 performs the luminescence detection. That is to say, the magnetic separation cleaning liquid path system 83 uses the vacuum chamber SR51 and the first vacuum pump SR53 as a magnetic separation drive source 51 to realize the discharge of the waste cleaning liquid from the reaction vessel. The first vacuum pump SR53 can provide a stable negative pressure to the vacuum chamber SR51, such that the vacuum chamber SR51 has sufficient negative pressure to discharge the waste cleaning liquid of the magnetic separation device 4 and the waste liquid after the incubation and luminescence detection device 2 performs the detection. In addition, the negative pressure of the vacuum chamber SR51 is stable and the flow rate is stable. It is possible to prevent the magnetic beads in the reaction vessel from being aspirated away due to the instability of the aspiration force, to ensure the cleaning effect and thus ensure the accuracy of the detection result.

The magnetic separation cleaning liquid path system 83 further comprises a magnetic separation liquid discharge pipeline 833, a second magnetic separation control valve V832, and a recovery pipeline 835. The magnetic separation liquid discharge pipeline 833 is connected to the magnetic separation drive source SR5 and the liquid discharge needle, and the second magnetic separation control valve V832 is provided on the magnetic separation liquid discharge pipeline 833 for discharging the waste cleaning liquid from the reaction vessel. The magnetic separation drive source SR5 is also connected to the recovery pipeline 835, and the waste cleaning liquid in the reaction vessel is discharged into the waste liquid bucket through the recovery pipeline 835. The magnetic separation drive source SR5 is a power source for the discharge of the waste cleaning liquid after the separation cleaning are performed.

The second magnetic separation control valve V832 is configured to control the opening and closing of the magnetic separation liquid discharge pipeline 833. When the waste cleaning liquid in the reaction vessel needs to be discharged, the second magnetic separation control valve V832 is opened, such that the magnetic separation liquid discharge pipeline 833 is a passage. In this case, the magnetic separation drive source SR5 aspirates, via the liquid discharge needle, the waste cleaning liquid from the reaction vessel through the magnetic separation liquid discharge pipeline 833, and the waste cleaning liquid is discharged into the waste liquid bucket through the recovery pipeline 835. After the discharge of the waste cleaning liquid is completed, the second magnetic separation control valve V832 is closed. In this case, the separation power source cannot discharge the waste cleaning liquid.

It can be understood that the waste liquid bucket is located below the carrying platform. After the waste liquid bucket is full, the waste liquid bucket can be removed, the waste liquid in the waste liquid bucket is emptied, and the waste liquid bucket is then placed in the fully automated chemiluminescence immunoassay analyzer. Moreover, the waste liquid bucket may be a part of the fully automated chemiluminescence immunoassay analyzer, or may be provided independently of the fully automated chemiluminescence immunoassay analyzer.

In addition, the magnetic separation cleaning liquid path system 83 can also discharge the waste cleaning liquid from the magnetic separation swab 44. The magnetic separation cleaning liquid path system 83 further comprises a second magnetic separation cleaning pipeline 836 and a fifth magnetic separation control valve V835. The second magnetic separation cleaning pipeline 836 is connected to the magnetic separation swab 44 and the magnetic separation drive source SR5. The fifth magnetic separation control valve V835 is provided on the second magnetic separation cleaning pipeline 836 for controlling the opening and closing of the second magnetic separation cleaning pipeline 836. The waste cleaning liquid is discharged into the waste liquid bucket by the magnetic separation drive source SR5.

One end of the second magnetic separation cleaning pipeline 836 is connected to the cleaning liquid cleaning outlet of the magnetic separation swab 44, and the other end of the second magnetic separation cleaning pipeline 836 is connected to the magnetic separation drive source SR5. When the waste liquid is discharged, the fifth magnetic separation control valve V835 opens the second magnetic separation cleaning pipeline 836. The waste cleaning liquid is discharged into the waste liquid bucket by the magnetic separation drive source SR5. After the discharge of the waste liquid is completed, the fifth magnetic separation control valve V835 closes the second magnetic separation cleaning pipeline 836.

Preferably, the magnetic separation drive source SR5 of the fully automated chemiluminescence immunoassay analyzer further comprises a negative pressure sensor SR52. The vacuum chamber SR51 is connected to the magnetic separation liquid discharge pipeline 833 and the recovery pipeline 835, and the first vacuum pump SR53 is provided on the recovery pipeline 835. The negative pressure sensor SR52 is configured to detect the pressure of the vacuum chamber SR51 and the pressure is adjusted by the first vacuum pump SR53. The cooperation between the vacuum chamber SR51, the first vacuum pump SR53 and the negative pressure sensor SR52 can form a negative pressure power source with a controllable pressure, and replace the currently used peristaltic pumps, so that both the cost and the failure rate can be reduced, and it is convenient to maintain.

Moreover, the magnetic separation cleaning liquid path system 83 further comprises a sixth magnetic separation control valve V836. The sixth magnetic separation control valve V836 is provided on the recovery pipeline 835. The sixth magnetic separation control valve V836 is also connected to the second magnetic separation cleaning pipeline 836 and the vacuum chamber SR51, for respectively communicating the recovery pipeline 835 with the vacuum chamber SR51 and the second magnetic separation cleaning pipeline 836. Particularly, one end of the sixth magnetic separation control valve V836 is connected to the recovery pipeline 835, and the other two ends of the second magnetic separation control valve V832 are respectively connected to the vacuum chamber SR51 and the second magnetic separation cleaning pipeline 836.

The sixth magnetic separation control valve V836 disconnects the second magnetic separation cleaning pipeline 836 from the recovery pipeline 835 while communicating the vacuum chamber SR51 with the recovery pipeline 835. In this case, the waste liquid in the reaction vessel can enter the recovery pipeline 835 through the magnetic separation pipeline 833 and the vacuum chamber SR51 and is then discharged into the waste liquid bucket. The sixth magnetic separation control valve V836 communicates the second magnetic separation cleaning pipeline 836 with the recovery pipeline 835 while disconnecting the vacuum chamber SR51 from the recovery pipeline 835. In this case, the waste cleaning liquid in the magnetic separation swab 44 enter the recovery pipeline 835 through the second magnetic separation cleaning pipeline 836 and is then discharged into the waste liquid bucket.

Optionally, when the number of the cleaning liquid injection mechanisms 42 and the number of the cleaning liquid discharge mechanisms 43 are both at least two, and the number of the magnetic separation liquid injection pipelines 832, the number of the magnetic separation liquid discharge pipelines 833, the number of the first magnetic separation cleaning pipelines 834, the number of the second magnetic separation cleaning pipelines 836, the number of the second magnetic separation control valves V832, the number of the third magnetic separation control valves V833, the number of the fourth magnetic separation control valves V834 and the number of the fifth magnetic separation control valves V835 are consistent with the number of the cleaning liquid injection mechanisms 42. That is to say, provided are at least two first magnetic separation cleaning pipelines 834 arranged in parallel, at least two second magnetic separation cleaning pipelines 836 arranged in parallel, at least two at least two magnetic separation liquid injection pipelines 832 arranged in parallel, and at least two at least two magnetic separation liquid discharge pipelines 833 arranged in parallel, and the arrangement of the valves is adapted to their pipeline. In this way, the analyte in the reaction vessel can be cleaned at least twice, to prevent the impurities from remaining in the analyte, thereby ensuring the purity of the analyte, and improving the reliability of the detection of the sample.

In addition, with a plurality of valves and the magnetic separation liquid injection pipeline 832 and the first magnetic separation cleaning pipeline 834, it is possible to realize the injection of the cleaning liquid and the cleaning function by one magnetic separation syringe, and the purpose of cost saving can be achieved. At the same time, the same power source, that is, the magnetic separation syringe SR4, is configured to control each cleaning liquid injection mechanism 42, and the same power source, that is, the magnetic separation drive source SR5, is configured to control each cleaning liquid discharge mechanism 43. In addition, each cleaning liquid discharge mechanism 43 is equipped with a magnetic separation swab 44. It is possible that the liquid discharge needle in each cleaning liquid discharge mechanism 43 can be maintained without the need to horizontally move the liquid discharge needle to an additional cleaning position, so that the mechanical structure of the magnetic separation cleaning device 4 is simplified, and the time of magnetic separation in the testing process is shortened to speed up the flux.

The magnetic separation cleaning liquid path system 83 further comprises a seventh magnetic separation control valve V837. The seventh magnetic separation control valve V837 is provided on the magnetic separation liquid aspiration pipeline 831 for aspirating the cleaning liquid from at least two cleaning liquid containers. The dispensing liquid path system 81 further comprises a fourth dispensing control valve V814. The fourth dispensing control valve V814 is provided on the second dispensing cleaning pipeline 813 for aspirating the cleaning liquid from at least two cleaning liquid containers. It can be understood that the number of the cleaning liquid containers storing the cleaning liquid may be two. The two cleaning liquid aspiration branch pipes are connected to the magnetic separation liquid aspiration pipeline 831 via the seventh magnetic separation control valve V837, and the other end of each of the two cleaning liquid aspiration branch pipes respectively extends into the respective cleaning liquid container. The seventh magnetic separation control valve V837 communicates one of the cleaning liquid aspiration branch pipes with the magnetic separation liquid aspiration pipeline 831 while disconnecting the other cleaning liquid aspiration branch pipe from the magnetic separation liquid aspiration pipeline 831. Two dispensing aspiration branch pipes are respectively connected to the second dispensing cleaning pipeline 813 via the fourth magnetic separation control valve V834, and the other end of each of the two dispensing aspiration branch pipes respectively extends into the respective cleaning liquid container. The fourth magnetic separation control valve V834 communicates one of the dispensing aspiration branch pipes with the second dispensing cleaning pipeline 813 while disconnecting the other dispensing aspiration branch pipe from the second dispensing cleaning pipeline 813. In this way, when the cleaning liquid in one of the cleaning liquid containers is used up, the other cleaning liquid container can continue to provide the cleaning liquid, such that when the cleaning liquid is replenished into the cleaning liquid container, the fully automated chemiluminescence immunoassay analyzer can operate normally without downtime, increasing the processing efficiency thereof. Preferably, a cleaning liquid detection component 88 is further provided below the left front side of the carrying platform for detecting the remaining amount of cleaning liquid in the cleaning liquid container, which is convenient for monitoring, so that the user can add the cleaning liquid in time.

Optionally, the liquid path device 8 further comprises a condensed water discharge pipeline. The condensed water discharge pipeline is connected to the fifth magnetic separation control valve V835 and a water discharge channel 1212 of the reagent housing 121. The fifth magnetic separation control valve V835 disconnects the second magnetic separation cleaning pipeline 836 from the magnetic separation drive source SR5, and communicates the water discharge channel 1212 with the magnetic separation drive source SR5, for discharging condensed water from the reagent housing 121. That is to say, the liquid path device 8 can also discharge the condensed water from the reagent housing 121 to avoid the potential electrical safety problems caused by the accumulation of the condensed water in the reagent housing 121. The fifth magnetic separation control valve V835 controls the discharge of the condensed water from the reagent housing 121 while controlling the second magnetic separation cleaning pipeline 836 to discharge the waste cleaning liquid. When the condensed water is discharged, the fifth magnetic separation control valve V835 communicates the condensed water discharge pipeline with the second vacuum pump SR55 and disconnects the second magnetic separation cleaning pipeline 836 from the second vacuum pump SR55, and the condensed water in the reagent housing 121 enters the condensed water discharge pipeline through the water discharge channel 1212, and is then discharged into the waste liquid bucket by the second vacuum pump SR55. When the waste cleaning liquid is discharged, the fifth magnetic separation control valve V835 disconnects the condensed water discharge pipeline from the second vacuum pump SR55, and communicates the second magnetic separation cleaning pipeline 836 with the second vacuum pump SR55, and the waste cleaning liquid is discharged into the waste liquid bucket through the second magnetic separation cleaning pipeline 836 by the second vacuum pump SR55.

Still optionally, the liquid path device 8 further comprises an incubation waste liquid discharge pipeline and an incubation waste liquid control valve. The incubation waste liquid discharge pipeline is connected to the waste liquid discharge device 7 and the magnetic separation drive source SR5. The incubation waste liquid control valve is provided on the incubation waste liquid discharge pipeline for controlling the opening and closing of the incubation waste liquid discharge pipeline, to discharge the waste liquid from the reaction vessel subjected to the detection into the waste liquid bucket. That is to say, the liquid path device 8 can also discharge the waste liquid after the reaction vessel is subjected to the detection. The incubation waste liquid discharge pipeline is connected to the waste liquid discharge device 7 and the vacuum chamber SR51. When the incubation waste liquid control valve controls the incubation waste liquid discharge pipeline to be a passage, the waste liquid discharge device 7 delivers the waste liquid to the incubation waste liquid pipeline from the reaction vessel with the waste liquid to be discharged, and is discharged into the waste liquid bucket through the vacuum chamber SR51 and the recovery pipeline 835. After the waste liquid is discharged, the incubation waste liquid control valve closes the incubation waste liquid discharge pipeline.

Moreover, the liquid path device 8 further comprises a flushing pipeline and a flushing control valve. The flushing pipeline is connected to the third magnetic separation control valve V833 and the vacuum chamber SR51. The flushing control valve is provided on the flushing pipeline for controlling the opening and closing of the flushing pipeline. When flushing, the flushing control valve makes the flushing pipeline be a passage, and the waste cleaning liquid discharged through the first dispensing liquid discharge pipeline 814 and the second dispensing liquid discharge pipeline 815 can enter the vacuum chamber SR51 through the flushing pipeline, to clean the vacuum chamber SR51. This is because after the luminescence detection is performed, the waste liquid is relatively dirty, and the cleanliness of the vacuum chamber SR51 can be increased after being cleaned by the waste cleaning liquid. Of course, in other implementations of the present disclosure, other flushing structures may also be introduced to clean the vacuum chamber SR51. If flushing is not required, the flushing control valve closes the flushing pipeline.

When the waste cleaning liquid is discharged from one of the magnetic separation liquid discharge pipelines 833, the corresponding valve thereon is opened, while the valves on the remaining magnetic separation liquid discharge pipelines 833 are closed to prevent the vacuum chamber SR51 from aspirating air, such that the vacuum chamber SR51 can accurately aspirate the waste cleaning liquid from the reaction vessel; and when the waste cleaning liquid is discharged from the reaction vessel, the incubation waste liquid control valve is also closed accordingly. When the detected waste liquid is discharged from the reaction vessel, the incubation waste liquid control valve is opened, and the magnetic separation liquid discharge pipeline 833 and the valve thereon are closed to ensure the smooth discharge of the detected waste liquid. It can be understood that each valve of the liquid path device 8 is automatically controlled by the main control device 77.

By cooperating the design of pipeline connection and the switching of the valves, the liquid path device 8 realizes the functions required by the fully automated chemiluminescence immunoassay analyzer for the detection and maintenance procedures of the gas/liquid path with less control devices. The cost has been greatly reduced, and at the same time, the whole machine can avoid the restriction of the number and volume of devices and get better integration and miniaturization. Moreover, the use of the dispensing needle swab 34 enables the detection procedure to allow the sample and reagent adding processes of the dispensing needle 31 not to be restricted by the fixed position of the cleaning pool 35, thereby improving the testing flux. A negative pressure source of the vacuum chamber SR51 of the magnetic separation cleaning system replaces the peristaltic pump, achieving innovations and advantages in terms of volume, cost, and ease of maintenance. In addition, the magnetic separation swab 44 allows the whole machine to clean the liquid discharge needle without the need for additional movable components, thereby eliminating the threat of carrying pollution at low cost.

Optionally, the sample receiving mechanism 11 of the sample and reagent receiving device 1 further comprises a needle cleaning structure 114 for cleaning the dispensing needle 31 of the dispensing device 3. The needle cleaning structure 114 is provided on the chassis 112 and located between adjacent two of the sample holders 111. That is to say, the needle cleaning structure 114 is integrated on the sample receiving mechanism 11 instead of being provided on other structures of the chemiluminescence analyzer. In this way, it is possible to reduce the overall size of the chemiluminescence analyzer. Moreover, the needle cleaning structure 114 being provided on the sample receiving mechanism 11 can also reduce the movement path of the dispensing needle 31 and improve the processing efficiency of the sample. This is because the dispensing needle 31 needs to be cleaned after transferring the sample or the reagent, to avoid cross contamination when transferring the sample or the reagent next time. After transferring the sample or the reagent, the dispensing needle 31 returns to the sample receiving mechanism 11 for direct cleaning, reducing the path of movement of the dispensing needle 31 to another position for cleaning and then returning to the sample receiving mechanism 11 or the reagent receiving mechanism 12, improving the transfer efficiency of the dispensing needle 31, and in turn improving the efficiency of the whole machine. Moreover, the needle cleaning structure 114 may be a cleaning pool, and the bottom of the cleaning pool is connected to a liquid path duct through which the cleaning liquid is delivered and the waste cleaning liquid is discharged. Of course, the needle cleaning structure 114 may also be other structures capable of carrying the cleaning liquid, such as bottles. Moreover, the needle cleaning structure 1141 can also deliver an enhanced cleaning liquid through the liquid path duct to perform the enhanced cleaning on the dispensing needle, to ensure the cleaning effect.

Referring to FIGS. 3 to 6, it can be understood that due to differences between various samples, there are also differences in the detections to be performed, so the sample and reagent receiving device 1 can also be used to identify the position and the item of detection of the sample, and identify the position and the type of the reagent. Particularly, identification codes are provided on both the outer side of the sample vessel and the outer side of the reagent vessel. The sample and reagent receiving device 1 can scan the identification code of each sample vessel to identify the position and the item to be detected of the sample. The sample and reagent receiving device 1 can also scan the identification code of each reagent vessel to identify the location and type of the reagent. This can avoid problems of performing an erroneous item of detection or adding an erroneous sample or reagent, etc., and ensure that the detection of the sample is smoothly performed. It can be understood that the identification code may be a barcode, a two-dimensional code, or other types of information that is easy to identify.

Particularly, the sample and reagent receiving device 1 further comprises an identification code scanner 13 for scanning identification codes, and the sample receiving mechanism 11 is provided with a scanning notch 1111. The identification code scanner 13 can scan identification codes of the sample vessels on the sample receiving mechanism 11, and the identification code scanner 13 can also scan identification codes of the reagent vessels on the reagent receiving mechanism 12 through the scanning notch 1111. The identification code scanner 13 is configured to scan and identify the identification code of the sample vessel and the identification code of the reagent vessel. The main control device 77 is electrically connected to the identification code scanner 13. The main control device is configured to control the identification code scanner 13 to perform a scanning operation, and store various information, such as the position, the item to be detected and other information of the sample, and the position, the type and other information of the reagent, that is acquired by the identification code scanner 13 through scanning. Before the fully automated chemiluminescence immunoassay analyzer detects the sample, the identification code scanner 13 first scans the identification code of each sample vessel in the sample receiving mechanism 11 and scans the identification code of each reagent vessel in the reagent receiving mechanism 12. It can be understood that the identification code scanner 13 scans the identification code of the sample and the identification code of the reagent in any sequence, and may scan the identification code of the sample first or scan the identification code of the reagent first, which has no substantial impact on the detection of the sample. Of course, in other implementations of the present disclosure, the identification code of the sample vessel and the identification code of the reagent vessel may also be scanned during the detection of the sample.

The identification code scanner 13 is located on the outer side of the sample and reagent receiving device 1. The ring-shaped sample receiving mechanism 11 divides the space into the inner side and the outer side. The inner side refers to the space where the reagent receiving mechanism is located. Correspondingly, the other space is the outer side of the sample receiving mechanism. The identification code scanner 13 can directly scan the identification code of the sample on the sample receiving mechanism, but the sample reagent receiving mechanism is sleeved outside the reagent receiving mechanism, and the sample receiving mechanism would block the reagent receiving mechanism, which is not conducive to the scanning of the identification code of the reagent vessel. Therefore, the scanning notch 1111 is provided in the sample receiving mechanism. The scanning notch 1111 is to facilitate the identification code scanner 13 in scanning, through the scanning notch 1111, the identification codes of the reagent vessels in the reagent receiving mechanism on the inner side of the sample receiving mechanism. Particularly, the identification code scanner 13 can scan the identification codes of the sample vessels on the sample receiving mechanism, and the identification code scanner 13 can also scan the identification codes of the reagent vessels on the reagent receiving mechanism 2 through the scanning notch 1111.

The identification code scanner 13 can transmit the basic information of the sample such as the position and the item to be detected, user's basic information, etc., to the main control device. Moreover, during the processing of the sample, the main control device performs a real-time tracking on the detected sample. After the luminescence detection is performed on the sample, the main control device acquires parameters of the sample detected in the incubation and luminescence detection step, and corresponds the parameters of the sample to the basic information of the sample, such that the sample corresponds to each of the detection parameters to avoid errors. In this embodiment, the loading of the sample vessel is performed manually. When loading, the identification code of the sample vessel is placed outward, which is convenient for scanning by the identification code scanner 13. Of course, when the sample vessel is automatically loaded and delivered, if the identification code of the sample vessel does not face outward, a rotating structure may also be provided to rotate the sample vessel such that the identification code of the sample vessel faces outward.

The sample and reagent receiving device of the fully automated chemiluminescence immunoassay analyzer of the present disclosure adopts the configuration in which the sample receiving mechanism is sleeved outside the reagent receiving mechanism, and cooperates with the identification code scanner 13. When the sample receiving mechanism drives a sample vessel therein to rotate, the identification code scanner 13 scans the identification code of the sample vessel. When the scanning notch 1111 of the sample receiving mechanism corresponds to the identification code scanner 13, the reagent receiving mechanism drives a reagent vessel therein to rotate, and the identification code scanner 13 scans the identification code of the reagent vessel through the scanning notch 1111. That is, the identification code of the sample vessel and the identification code of the reagent vessel are scanned by the same identification code scanner 13, which effectively solves the problems of high cost and large footprint caused by the current scanning performed by two identification code scanners 13, to reduce the production cost and the footprint, so that the size of the sample and reagent receiving and scanning system is small, thereby reducing the overall size of the chemiluminescence analyzer.

Preferably, the identification code scanner 13 is fixedly arranged on the outer side of the sample receiving mechanism 11. This can facilitate the chemiluminescence analyzer in determining the positional information of each sample vessel and each reagent vessel. The sample receiving mechanism 11 drives the sample vessels to sequentially rotate to the identification code scanner 13 to perform scanning. When the scanning notch 1111 corresponds to the identification code scanner 13, the reagent receiving mechanism 12 drives the reagent vessels to sequentially rotate to the scanning notch 1111 to perform scanning. Particularly, after the identification code scanner 13 is fixed, the identification code scanner 13 has a scanning area which can be projected onto the sample receiving mechanism 11 and the reagent receiving mechanism 12. When the identification codes of the sample vessels are scanned, the sample receiving mechanism 11 drives each sample vessel thereon to rotate, such that the sample vessels sequentially passes through the scanning area of the identification code scanner 13, so that the identification code scanner 13 sequentially records the information of the sample vessels to realize the scanning of the identification codes of the sample vessels. When the identification codes of the reagent vessels are scanned, first, the scanning notch 1111 of the sample receiving mechanism is aligned with the identification code scanner 13 such that the identification code scanner 13 can pass through the notch and correspond to the reagent vessels in the reagent receiving mechanism 12, and the reagent receiving mechanism 12 then drives each reagent vessel thereon to rotate, such that the reagent vessels sequentially pass through the scanning area of the identification code scanner 13, so that the identification code scanner 13 sequentially records the information of the reagent vessels to realize the scanning of the identification codes of the reagent vessels. Of course, in other implementations of the present disclosure, the identification code scanner 13 may also be non-fixed, as long as the identification code scanner 13 can be aligned with the scanning notch 1111 to scan the identification codes of the reagent vessels.

Further, there is a preset spacing between adjacent two of the sample holders to form a scanning notch 1111, the reagent housing is provided with a scanning window 1211, and when the scanning window 1211, the scanning notch 1111 and the identification code scanner 13 correspond to one another, the reagent disc 122 drives the multiple reagent vessels to rotate, such that the reagent vessels sequentially move to the scanning window 1211, and the identification code scanner 13 scans the identification codes of the reagent vessels.

It can be understood that, after adjacent two of the sample holders 111 are overlapped, there is a large space between the adjacent sample holders 111, through which the identification codes of the reagent vessels in the reagent receiving mechanism 12 can be scanned. Of course, the adjacent sample holders 1111 can be supported separately by support columns, and this can also ensure that there is a scanning notch 1111 between the adjacent sample holders 1111. Preferably, in this embodiment, the number of the scanning notches 1111 is one, that is, the identification codes of the reagent vessels are identified through one scanning notch 1111. In this way, the scanning requirements can be met, and at the same time the sample holders are compact in structure, thereby carrying as many sample vessels as possible to avoid frequent replenishment of the sample vessels. Of course, in other implementations of the present disclosure, a scanning notch 1111 may be provided between any adjacent two of the sample holders 111, or scanning notches 1111 may be provided between several adjacent two of the sample holders 111. In this way, the scanning requirements can also be met.

In this embodiment, the reagent housing 121 is provided with a scanning window 1211. That is to say, the identification code scanner 13 scans the identification codes of the reagent vessels in the reagent housing 121 through the scanning window 1211. In this way, it is possible to avoid the loss of cold, and it is easy to maintain the low-temperature environment in the reagent housing 121. When the identification codes of the reagent vessels are scanned, the scanning window 1211, the scanning notch 1111 and the identification code scanner 13 correspond to one another, the reagent disc 122 drives the multiple reagent vessels to rotate, to drive the reagent vessels sequentially to move to the scanning window 1211, and the identification code scanner 13 scans the identification codes of the reagent vessels.

It should be noted that, since there is a gap between adjacent sample vessels, in order to prevent the identification code scanner 13 from scanning the identification codes of the reagent vessels in the reagent housing 121 through the gap, the reagent disc is controlled to rotate before scanning the identification codes of the sample vessels 122, such that the space between adjacent reagent vessels corresponds to the scanning window 1211. In this way, when scanning the identification codes of the sample vessels, the identification code scanner 13 is always aligned with the scanning window 1211 of the reagent housing 121 and the space between two adjacent reagent vessels. When the sample receiving mechanism 11 drives the sample vessels to rotate, the sample vessels are sequentially scanned by the identification code scanner 13, even if the gap between adjacent sample vessels is aligned with the identification code scanner 13, because the scanning window 1211 corresponds to the space between two reagent vessels, the identification code scanner 13 will not mistakenly scan the identification codes of the reagent vessels, thereby ensuring the accuracy of the scanning result. Optionally, the spacing between adjacent sample vessels is minimized, so that the identification codes of the reagent vessels cannot be completely scanned through the spacing, to avoid interference with the sample barcode, and at the same time, the capacity of the sample vessels can be increased as much as possible.

Further, the reagent housing 121 is provided with a transparent window 1213. The transparent window 1213 is installed at the scanning window 1211. The transparent window 1213 corresponds to the identification code scanner 13. During the rotation of the sample holders 111, the identification code scanner 13 scans, via the transparent window 1213, the identification codes of the reagent vessels in the reagent disc through the preset spacing. Preferably, the reagent housing 121 is fixedly arranged, such that the transparent window 1213 and the identification code scanner 13 always remain stationary. The transparent window 1213 can isolate the inside and outside of the reagent housing 121 to avoid the loss of cold from the reagent housing 121. The transparent window 1213 corresponds to the identification code of the reagent vessel on the reagent disc 122 in the reagent housing 121, so that the identification code scanner 13 scans the identification codes of the reagent vessels on the reagent disc 121 through the preset spacing and the transparent window 1213. Optionally, the transparent window 1213 may be transparent glass, or may be made of another transparent material.

Referring to FIGS. 3 to 7, as an implementable way, the reagent receiving mechanism 12 further comprises a cooling structure 127. The cooling structure 127 is configured to cool the interior of the reagent housing 121 such that the interior of the reagent housing 121 is in a low-temperature environment, which is convenient for reagent storage. As an example, the bottom of the reagent housing 121 has a mounting position, and the cooling structure 127 is mounted in the mounting position. Due to the small volume, the cooling structure 127 may not occupy the central area. In this way, it is possible to reduce the diameter of the rotary shaft driving the rotation of the reagent disc 122, to reduce the wiring, and to improve the operation efficiency of driving the reagent disc 122. At the same time, the cooling structure 127 also does not interfere with the reagent disk 122 and its transmission drive component. Since the cooling structure 127 does not occupy the central area of the reagent housing 122, the reagent housing 122 may internally store a structure for driving the reagent vessels to mix the reagents therein. If the same number of reagent vessels are placed, the radius of the reagent housing 121 is reduced, the volume and surface area thereof are also greatly reduced. Under the same outside environment, the amount of heat exchange of the reagent housing 121 caused by the surface heat conduction is greatly reduced. Therefore, the power required by the cooling structure 127 is reduced, so that the volume of the cooling structure 127 can be reduced.

Particularly, the cooling structure 127 comprises a cooling component. The cooling component is located below the reagent disc 122 and offset from the center of the reagent housing 121 for cooling the interior of the reagent housing 121. Particularly, the cooling component has a cold end and a hot end. The cold end of the cooling component is provided below the reagent disc 122 for cooling the reagent disc 122, and the hot end of the cooling component is provided at the transparent window 1213. After the cooling component is energized, the cold end can generate cold to cool the reagent disc 122, thereby cooling the reagent in the reagent vessel. Since the interior of the reagent housing 121 requires cooling to ensure the reagent storage, and the exterior of the reagent housing is a normal-temperature space, condensed water would be generated on the transparent window 1213, affecting the scanning of the identification code scanner 13. After the heat generated by the hot end of the cooling component is transmitted to the transparent window 1213, the contact portion between the transparent window 1213 and the exterior of the reagent housing can be heated, to prevent the generation of the condensed water on the transparent window 1213.

Optionally, the cooling structure 127 further comprises a cold-end spreader, which is provided in the reagent housing 121 for accelerating the spreading of the cold, ensuring that the cold is uniformly distributed in the reagent housing 121, and ensuring the cooling effect. Moreover, the cold-end spreader is also located below the reagent disc 122. In this way, it is possible to prevent the cooling structure 127 from occupying the space of the reagent vessel and ensure the number of reagent vessels carried on the reagent disc 122. As an example, the cold-end spreader may be a cold-end fan and/or cold-end fins, etc.

Still optionally, the reagent receiving mechanism 12 further comprises a hot-end radiator 128 and a heat-conducting component 1281. The hot-end radiator 128 is connected to the hot end of the cooling component and is located on an outer side of the reagent housing 121. Due to the eccentric arrangement of the cooling structure 127, the hot end of the cooling component can be close to the inner wall of the reagent housing 121. In this way, when the heat of the hot end is drawn out through an air duct, the air duct can be shortened, so that the structure of the air duct is simple, and the air volume-air pressure performance of the hot-end radiator 128 requires a good heat non-dissipation effect. It can be understood that the hot end of the cooling component may transmit heat to the hot-end radiator 128 through a heat-conducting plate. The heat-conducting component 1281 is connected to the hot-end radiator 128 and corresponds to an outer side of the scanning window 1211. That is, the heat-conducting component 1281 is connected to the hot-end radiator 128 and the outer side of the transparent window 1213 to transmit heat to the transparent window 1213, avoiding the loss of heat. The heat-conducting component 1281 is provided to realize a defogging function for the transparent window 1213, and has the characteristics of energy-saving, environmentally friendly, and simple structure. It can be understood that the outer side of the transparent window 1213 is between the sample receiving mechanism 11 and the reagent receiving mechanism 12, and the interior of the transparent window 1213 is the interior of the reagent housing. As an example, the hot-end radiator 128 may be a hot-end fan and/or hot-end heat dissipation fins, etc. The heat-conducting component 1281 is made of a heat-conducting material. In this embodiment, the hot-end radiator 128 comprises a hot-end fan 1283 and hot-end heat dissipation fins 1282, so that heat can flow directionally, accelerating the spreading of heat.

Optionally, the bottom of the reagent housing 121 is provided with a water discharge channel 1212. The water discharge channel 1212 is configured to discharge condensed water generated by the cooling structure 127. The water discharge channel 1212 can also discharge condensed water generated by other components of the reagent receiving mechanism 12, to prevent condensed water from being accumulated in the reagent housing 121, affecting the electrical safety.

In addition, referring to FIGS. 3 to 8, since the reagent aspiration holes 1231 communicate the interior of the reagent housing 121 and the exterior of the reagent housing 121, the interior of the reagent housing 121 is a cold environment with a cold air, and the exterior of the reagent housing 121 is a normal-temperature outside environment, condensed water is generated at the reagent aspiration holes 1231, and the condensed water may flow into the reagent vessel, affecting the detection accuracy of the sample. Therefore, the reagent housing lid 123 of the reagent receiving mechanism 12 of the present disclosure further comprises a condensation structure 125. The condensation structure 125 is provided on the reagent housing lid 123, the reagent aspiration holes 1231 are located in the condensation structure 125, and the condensation structure 125 is configured to receive the condensed water generated at the reagent aspiration holes 1231. The condensation structure 125 receives the condensed water from the reagent aspiration holes 1231 to prevent the condensed water from dripping into the reagent vessel, and it is also possible to avoid the loss of a large amount of cold and reduce the energy consumption.

Further, the condensation structure 125 comprises a condensation plate 1251 and a water receiving tray 1252 arranged opposite each other. The condensation plate 1251 is located above the water receiving tray 1252, and an airflow channel is enclosed by the condensation plate and the water receiving tray. The airflow channel is in communication with the interior of the reagent housing 121, that is, the cold air inside the reagent housing 121 can enter the airflow channel. Moreover, the condensation plate 1251 is detachably connected to the water receiving tray 1252. It can be understood that the condensation plate 1251 and the water receiving tray 1252 can be fixedly connected via connecting members such as screws. In this case, there is a gap between an edge of the condensation plate 1251 and an edge of the water receiving tray 1252. Of course, mounting plates may be respectively provided at the edges of the water tray 1252 and the condensation plate 1251, and it is also necessary to ensure that there is a gap between the two opposite mounting plates; and to ensure that the condensation space is in communication with the reagent housing 121. At the same time, an thermal insulation material may also be filled between the condensation plate 1251 and the water receiving tray 1252 except for the spaces for the airflow circulation and water receiving, to prevent the loss of cold from the reagent housing 121.

The reagent aspiration holes 1231 comprise a first reagent aspiration hole 12311 located in the condensation plate 1251 and a second reagent aspiration hole 12312 located in the water receiving tray 1252. The first reagent aspiration hole 12311 and the second reagent aspiration hole 12312 are arranged opposite each other, the outline of the first reagent aspiration hole 12311 can completely cover the outline of the second reagent aspiration hole 12312. That is to say, the projection of the first reagent aspiration hole 12311 on the water receiving tray 1252 can completely cover the second reagent aspiration hole 12312. In this embodiment, both the first reagent aspiration hole 12311 and the second reagent aspiration hole 12312 are circular, and the first reagent aspiration hole 12311 has a larger hole diameter than the second reagent aspiration hole 12312. Of course, in other implementations of the present disclosure, the first reagent aspiration hole 12311 and the second reagent aspiration hole 12312 may also respectively have other shapes. The first reagent aspiration hole 12311 is in communication with the outside environment, and the second reagent aspiration hole 12312 can be in communication with the interior of the reagent housing 121, thereby facilitating the dispensing needle 31 in extending into the reagent housing 121 to aspirate the reagent. Moreover, a baffle plate is provided at the edge of the water receiving tray 1252. The baffle plate is to prevent the condensed water on the water receiving tray 1252 from flowing out from the edge of the water receiving tray 1252.

After the condensation structure 125 is installed on the reagent housing lid 123, the cold air flowing in the reagent housing 121 passes through the edges of the condensation plate 1251 and the water receiving tray 1252 and enters the airflow channel, the normal-temperature air in the outside environment would enter the airflow channel through the first reagent aspiration hole 12311, and condensation occurs at the edge of the first reagent aspiration hole 12311 to generate condensed water. In this case, the condensed water drips onto the water receiving tray 1252 without entering the reagent housing 121 through the second reagent aspiration hole 12312.

Further, a hole wall of the first reagent aspiration hole 12311 extends toward the water receiving tray 1252 to form a first annular cylinder wall 1253, an inner wall face of the first annular cylinder wall 1253 is in contact with the outside environment via the first reagent aspiration hole 12311, and an outer wall face of the first annular cylinder wall 1253 is in contact with an environment where the airflow channel is located. The first annular cylinder wall 1253 can cover the second reagent aspiration hole 12312, and the first annular cylinder wall 1253 is located in the airflow channel. The first annular cylinder wall 1253 is connected to the first reagent aspiration hole 12311 and the second reagent aspiration hole 12312. When the dispensing needle 31 aspirates the reagent, the dispensing needle 31 can enter the first annular cylinder wall 1253 through the first reagent aspiration hole 12311, enter the reagent housing 121 through the second reagent aspiration hole 12312, and aspirate the reagent from the reagent vessel in the reagent housing 121.

The interior of the reagent housing 121 is a space with a cold environment, and the exterior of the reagent housing 121 is a normal-temperature environment. After the condensation structure 125 is installed on the reagent housing lid 123, the cold air flowing in the reagent housing 121 passes through the edges of the condensation plate 1251 and the water receiving tray 1252 and enters the airflow channel, and the cold air can be condensed on the first annular cylinder wall 1253. As a result, the temperature of the first annular cylinder wall 1253 is reduced. After the outside air enters through the first reagent aspiration hole 12311, a condensation process is formed, and the condensed water is built up on the first annular cylinder wall 1253, and finally drips onto the water receiving tray 1252. After reaching a tail end of the first annular cylinder wall 1253, the outside air enters a condensation channel from the first annular cylinder wall 1253 and the second reagent aspiration hole 12312 and is blended with the cold air, and most of the outside air would not flow into the condensation channel from the second reagent aspiration hole 12312 of the water receiving tray 1252, so that there is no condensed water in the second reagent aspiration hole 12312 of the water receiving tray 1252. This can prevent the condensed water generated at the first reagent aspiration hole 12311 from entering the reagent vessel.

Moreover, the outline of one end of the first annular cylinder wall 1253 away from the first reagent aspiration hole 12311 can completely cover the outline of the second reagent aspiration hole 12312. In this embodiment, the hole diameter of the end of the first annular cylinder wall 1253 away from the first reagent aspiration hole 12311 is larger than the hole diameter of the second reagent aspiration hole 12312. That is to say, the diameter of the projection of the end of the first annular cylinder wall 1253 on the water receiving tray 1252 is larger than the diameter of the second reagent aspiration hole 12312. The first annular cylinder wall 1253 serves as an interface between the outside environment and the environment where the airflow channel is located (the low-temperature environment in the reagent housing 121), and effectively increases the contact between the outside environment and the environment where the airflow channel is located, so that the condensed water is likely to be condensed on the first annular cylinder wall 1253 and can flow down the first annular cylinder wall 1253 and drip onto the water receiving tray 1252 without entering the second reagent aspiration hole 12312.

Still further, a hole wall of the second reagent aspiration hole 12312 extends toward the condensation plate 1251 to form a second annular cylinder wall 1254. The second annular cylinder wall 1254 corresponds to the first annular cylinder wall 1253, and a water blocking flange 1254 is configured to block the condensed water on the water receiving tray 1252 and prevent the condensed water from entering the reagent housing 121 through the second reagent aspiration hole 12312. Preferably, the second annular cylinder wall 1254 is in the shape of a constriction in a direction from the second reagent aspiration hole 12312 toward the condensation plate 1251, that is, the second annular cylinder wall 1254 has a smaller hole diameter than the first annular cylinder wall 1253. It can be understood that the diameter of an opening of the second annular cylinder wall 1254 is smaller than the diameter of the tail end of the first annular cylinder wall 1253, such that the condensed water on the first annular cylinder wall 1253 can flow to the outer side of the second annular cylinder wall 1254, to prevent the condensed water from flowing into the reagent housing 121. Moreover, the water receiving tray 1252 is provided with a water discharge hole, which is in communication with the water discharge channel 1212. The water discharge hole is configured to discharge the condensed water from the water receiving tray 1252 to prevent the condensed water from overflowing into the reagent housing from the water blocking flange 1254. The condensed water on the water receiving tray 1252 can enter the water discharge channel 1212 through the water discharge hole, and be discharged from the reagent housing 121 through the water discharge channel 1212. It can be understood that the water discharge hole may be in communication with the water discharge channel 1212 via a pipeline, or a water discharge flow-guiding structure may be provided, to avoid splashing when the condensed water is discharged from the water discharge hole.

Referring to FIGS. 1, 12, 13 and 15, as an implementable way, the magnetic separation attraction mechanism 48 is provided in the magnetic separation base 41 and located on two sides of a rotation path of the reaction vessel. The magnetic separation attraction mechanism 48 can attract magnetic beads in the reaction vessel to a side wall of the reaction vessel, and realize the cleaning of the analyte and the impurities in the reaction vessel. Particularly, in the process of attracting the magnetic beads by the magnetic separation attraction mechanism 48, the magnetic beads can drive the analyte to be attracted to the side wall of the reaction vessel. In this case, the impurities are dissolved in the cleaning liquid, and the waste liquid is discharged by the cleaning liquid discharge mechanism 43. It can be understood that the analyte and the impurities in the reaction vessel are cleaned by means of at least one separation cleaning operation, to ensure the purity of the analyte and thus to ensure the accuracy of the sample detection result.

Optionally, the magnetic separation attraction mechanism 48 comprises a plurality of attraction members, which are arranged alternately on the inter side and outer side of the movement trajectory of the reaction vessel, that is, one of the attraction members is located on the outer side of the movement trajectory of the reaction vessel, and adjacent two of the attraction members are located on the inner side of the movement trajectory of the reaction vessel. In this way, the magnetic beads in the reaction vessel can be sequentially attracted onto two opposite side walls, that is, the magnetic beads move on two opposite side faces of the inner wall of the reaction vessel. Not only the attraction and collection of magnetic particles in the separation process are realized, but also the dispersal of the magnetic particles in the cleaning process is achieved, so that the magnetic beads make full contact with the cleaning liquid during the movement to achieve the purpose of cleaning. The impurities such as enzymes remaining in the interior after the magnetic beads are accumulated are effectively cleaned, the effect of the additional structure such as the mixing mechanism to disperse the accumulated magnetic beads is reduced, and the cost is reduced. Moreover, the attraction members are installed from the bottom of the magnetic separation base 41, and can approach the side wall of the reaction vessel to the utmost extent, increasing the attraction force of the magnetic beads, and reducing the loss rate of the magnetic beads. As an example, the attraction members may be magnets, such as permanent magnets, electromagnets, etc.

Figure 15:
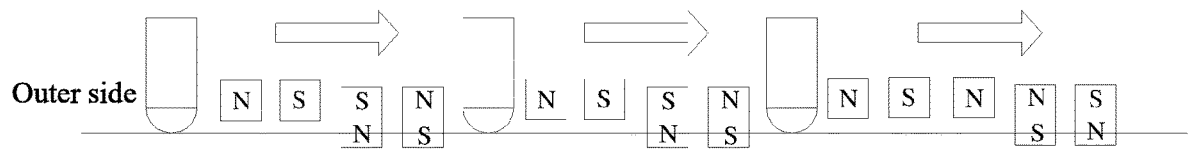
FIG. 15 is an expanded view of the horizontal distribution schematic view of first magnetic members and second magnetic members after the transfer path shown in FIG. 13 is expanded into a straight line.
Figure 16:
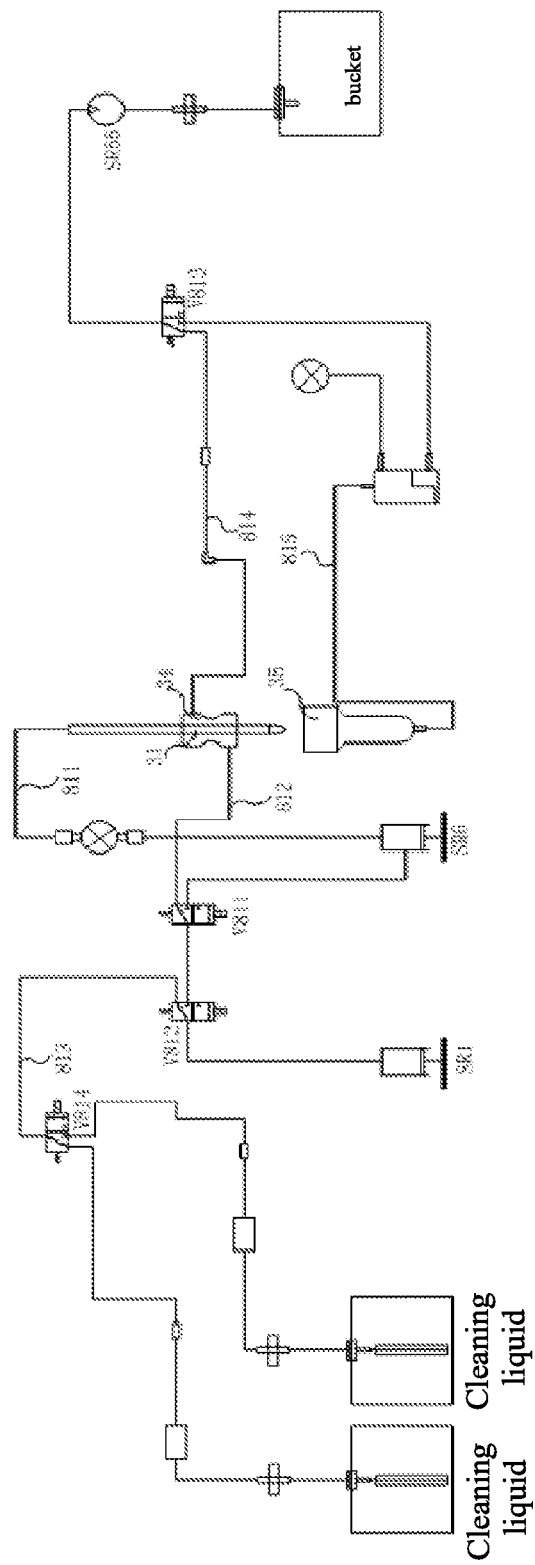
FIG. 16 is a schematic view of a liquid path of a dispensing liquid path system in a liquid path device according to an embodiment of the present disclosure.
Figure 17:
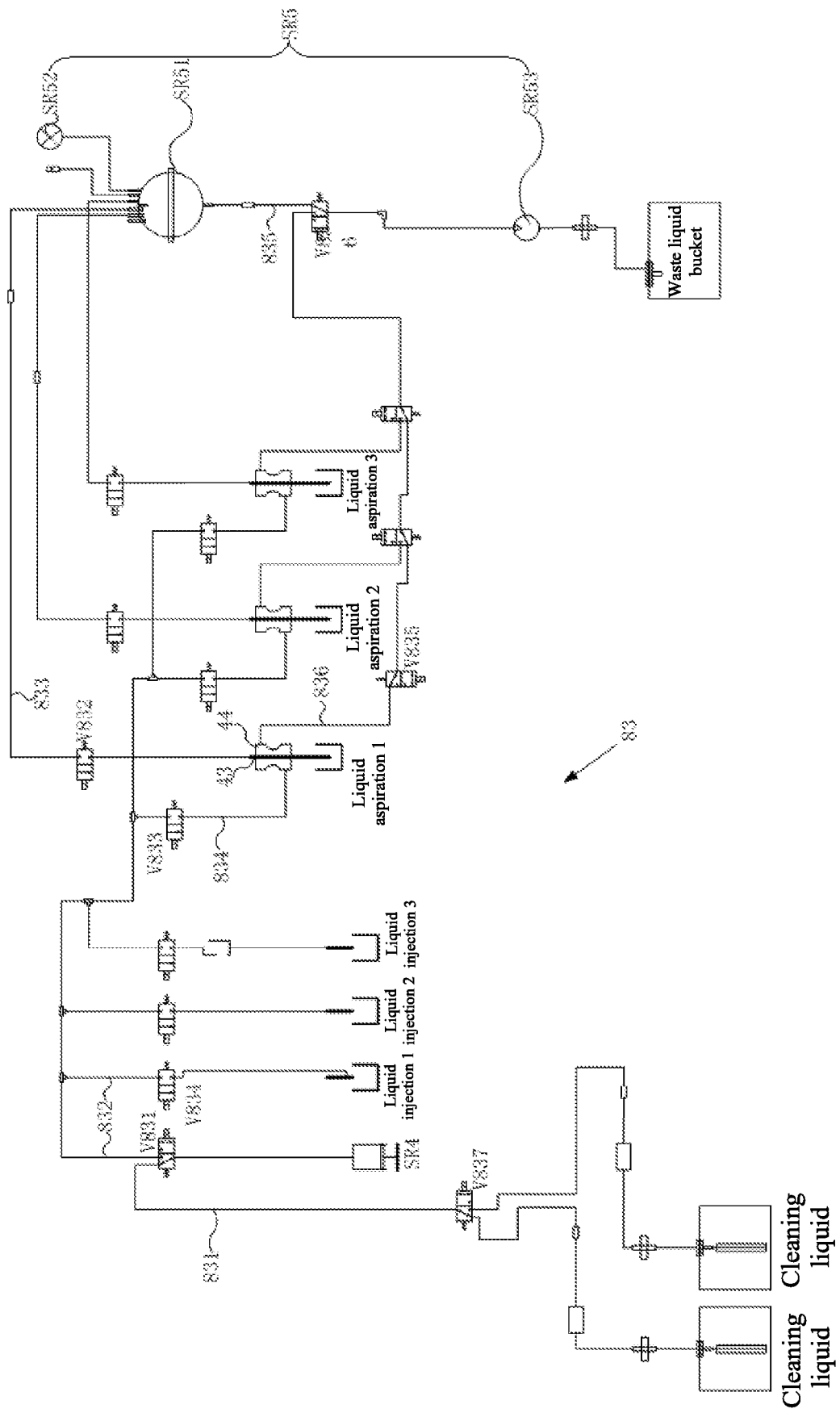
FIG. 17 is a schematic view of a liquid path of a magnetic separation cleaning liquid path system in a liquid path device according to an embodiment of the present disclosure.
Figure 18:
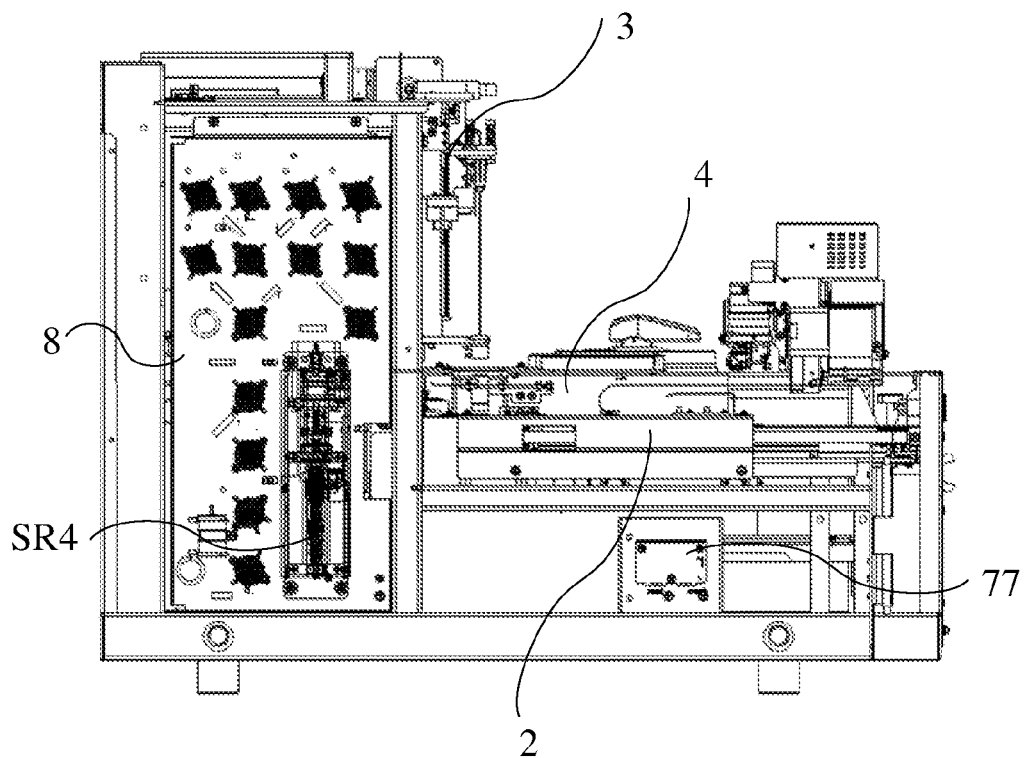
FIG. 18 is a left view of the fully automated chemiluminescence immunoassay analyzer shown in FIG. 1.

Further, the magnetic separation attraction mechanism 48 comprises a first magnetic member 481 and a second magnetic member 482. As an example, both the first magnetic member 481 and the second magnetic member 482 are magnets. That is, the first magnetic member 481 is a first magnet, and the second magnetic member 482 is a second magnet. The first magnetic member 481 and the second magnetic member 482 are distributed along a peripheral side of the magnetic separation base 41, and the first magnetic member 481 and the second magnetic member 482 are located at two side faces of the rotation path of the reaction vessel. Moreover, the first magnetic member 481 and the second magnetic member 482 are provided at the positions of the magnetic separation base 41 that correspond to the bottom of the reaction vessel, and the expanded distribution of the magnetic members is shown in FIG. 15.

The magnetic separation base 41 has a first cleaning position 414 between the cleaning liquid intake hole 412 and the cleaning liquid discharge hole 413, the first magnetic member 481 is arranged corresponding to the first cleaning position 414, and the second magnetic member 482 is arranged corresponding to the second cleaning position 415. In a vertical line direction, an inclined angle between a magnetic pole connection line of the first magnet 481 and the vertical line is a first inclined angle, and an inclined angle between a magnetic pole connection line of the second magnet 482 and the vertical line direction is a second inclined angle, wherein the first inclined angle is different from the second inclined angle. That is to say, the first magnetic member 481 and the second magnetic member 482 are respectively located on the inner and outer sides of the rotation path of the reaction vessel, and the magnetic pole connection line of the first magnetic member 481 and the magnetic pole connection line of the second magnetic member 482 are misaligned in an axial direction of the magnetic separation base 41, that is, they are arranged on different faces. When the magnetic separation base 41 drives the reaction vessel to move from the first magnetic member 481 to the second magnetic member 482, the first magnetic member 481 and the second magnetic member 482 arranged on different faces can collect the magnetic particles during the attraction of the magnetic particles from the side face where the first magnetic member 481 is located to the side face where the second magnetic member 482 is located, that is, moving from one side to the opposite side. This can accelerate the attraction speed of the magnetic particles, so that the magnetic retention efficiency is higher, the performance of the detection in terms of both cleaning and separation is ensured, and the accurate sample detection result is ensured, and the cleaning speed can also be increased, thereby further increasing the operation speed of the whole machine. It can be understood that the magnetic pole connection line refers to the connection line between N and S poles, or the connection line between S and N poles. The black dots in FIG. 13 indicate the collected magnetic beads, and the circle with a relatively large diameter indicates the transfer path of the reaction vessel.

It can be understood that the first magnetic member 481 is not provided at the cleaning liquid intake hole 412, because the step of adding the cleaning liquid is to be performed at the cleaning liquid intake hole 412, and the magnetic particles can be dispersed and make full contact with the cleaning liquid for cleaning. If the first magnetic member 481 is used for attraction at this time, the first magnetic member 481 is caused to directly attract the magnetic particles to the side wall, affecting the cleaning effect. The second magnetic member 482 is provided at the cleaning liquid discharge hole 413, in order to prevent the magnetic particles from being discharged when the waste cleaning liquid is discharged, and at the same time, the damage to the magnetic particles can also be prevented. Therefore, the first magnetic member 481 is arranged corresponding to the first cleaning position 414, and the second magnetic member 482 is arranged corresponding to the cleaning liquid discharge hole 413.

Moreover, the magnetic separation base 41 has a rotation axis, and the magnetic separation base 41 drives the reaction vessel to rotate about the rotation axis, that is, the magnetic separation bracket drives the reaction vessel to rotate sequentially about the rotation axis, and to sequentially pass through the access hole 411, the cleaning liquid intake hole 412, the cleaning liquid discharge hole 413, etc. Still further, the rotation axis is the vertical line direction, and the magnetic pole connection line of the first magnetic member 481 intersects a straight line where the extension direction of the rotation axis is located. That is to say, the magnetic pole connection line of the first magnetic member 481 is along a radial direction of the magnetic separation base 41, and may form different inclined angles with the rotation axis. Preferably, the magnetic pole connection line of the first magnetic member 481 is perpendicular to the magnetic pole connection line of the second magnetic member 482. That is to say, the placement positions of the first magnetic member 481 and the second magnetic member 482 are not limited in principle, as long as the magnetic pole connection lines thereof are perpendicular to each other. In this way, the magnetic forces of the first magnetic member 481 and the second magnetic member 482 can be staggered from each other, so that the magnetic particles are quickly collected in the corresponding perpendicular directions, thereby accelerating the process of attraction to the opposite sides, and avoiding the magnetic particles from being aspirated out when the waste cleaning liquid is discharged.

Particularly, the magnetic pole connection line of the first magnetic member 481 is perpendicular to the vertical line direction, and the magnetic pole connection line of the second magnetic member 482 is perpendicular to the vertical line direction, that is, the magnetic pole connection line of the first magnetic member 481 extends in the radial direction of the magnetic separation base 41, and the magnetic pole connection line of the second magnetic member 482 extends in the axial direction of the magnetic separation base 41. That is to say, the magnetic pole connection line of the first magnetic member 481 is parallel to the cross section of the reaction vessel, and the magnetic pole connection line of the second magnetic member 482 is perpendicular to the cross section of the reaction vessel, that is, the first magnetic member on the inner side of the movement trajectory of the reaction vessel 481 is placed horizontally in the radial direction, and the second magnetic member 482 on the outer side of the movement path of the reaction vessel is placed vertically. In this way, the first magnetic member 481 can attract the magnetic particles to the side wall of the reaction vessel once, and the second magnetic member 482 can collect the magnetic particles in the perpendicular direction in the process of attracting the magnetic particles to the other side wall of the reaction vessel, in combination with accelerating the process of attraction to the opposite side, to reduce the retention rate of the magnetic particles after being cleaned, so that the detection performance is ensured, and the cleaning speed can also be increased, thereby further increasing the operation speed of the whole machine. Of course, in other implementations of the present disclosure, the placements of the first magnetic member 481 and the second magnetic member 482 may also be reversed.

Optionally, there is at least one second cleaning position 415 between the first cleaning position 414 and the cleaning liquid discharge hole 413. The number of the first cleaning positions 414 is at least two, and the at least two first cleaning positions 414 and the at least one second cleaning position 415 are arranged in sequence. The number of the first magnetic members 481 is equal to the number of the first cleaning positions 414, the number of the second magnetic members 482 is equal to the sum of the number of the second cleaning positions 415 and the number of the cleaning liquid discharge holes 413, and the second magnetic members respectively correspond to the cleaning positions 414 and the cleaning liquid discharge holes 413. That is to say, during the rotation of the reaction vessel from the cleaning liquid intake hole 412 to the cleaning liquid discharge hole 413, the reaction vessel has a plurality of staying positions, namely the first cleaning positions 414 and the second cleaning positions 415 described above. Adding the first magnetic members 481 at the first cleaning positions 414 and adding the second magnetic members 482 at the second cleaning positions 415 can increase the attraction process of the magnetic particles, thereby improving the cleaning effect and ensuring the detection accuracy of the sample.

It can be understood that the number of the cleaning positions may be two, three, four or more. When the number of the first cleaning positions 414 is two, two first magnetic members 481 may be provided corresponding to the two first cleaning positions 414. It is also possible that one of the cleaning positions may be a first cleaning position 414 and the other may be a second cleaning position 415, then the first magnetic member 481 corresponds to the first cleaning position 414, and the second magnetic member 482 corresponds to the second cleaning position 415. When the number of the cleaning positions 414 is three, they may be two first cleaning positions 414 respectively corresponding to two first magnetic members 481, a second cleaning position 415 corresponding to a second magnetic member 482, and so on. It can be understood that the number of the first magnetic members 481 and the number of the second magnetic members 482 are not limited in principle, as along as they can be arranged corresponding to the cleaning positions.

Further, the magnetic properties of adjacent first magnetic members 481 toward the reaction vessel are opposite, and the orientations of magnetic poles of adjacent two of the second magnetic members 482 are opposite. That is to say, when there are two adjacent first magnetic members 481, the magnetic properties of the two adjacent first magnetic members 481 toward the reaction vessel are opposite, that is, the N pole of one of the first magnetic members 481 faces the reaction vessel, and the S pole of the other adjacent first magnetic member 481 faces the reaction vessel. When there are two adjacent second magnetic members 482, the orientations of magnetic poles of adjacent two of the second magnetic members 482 are opposite. That is, the adjacent N pole and S pole are arranged opposite each other, for example, the N pole faces upward and the S pole faces downward. In this way, the magnetic induction intensity obtained by the reaction vessel can be increased, and the attraction effect can be improved, thereby increasing the cleaning effect.

Still optionally, there are a plurality of cleaning liquid intake holes 412 and cleaning liquid discharge holes 413, and each of the cleaning liquid intake holes 412 and each of the cleaning liquid discharge holes 413 are alternately placed in a circumferential direction of the magnetic separation base. The number of groups of the first magnetic member 481 and the second magnetic member 482 is equal to the number of the cleaning liquid intake holes 412, and each group of the first magnetic member 481 and the second magnetic member 482 correspond to a group of the cleaning liquid intake hole 412 and the cleaning liquid discharge hole 413. That is to say, the corresponding cleaning liquid intake hole 412 and cleaning liquid discharge hole 413 are recorded as one group, and number of the first magnetic members 481 and the second magnetic members 482 required between the one group of the cleaning liquid intake hole 412 and the cleaning liquid discharge hole 413 are recorded as one group. The numbers of the two groups described above are the same, that is, it is possible to provide a plurality of groups of corresponding cleaning liquid intake holes 412 and cleaning liquid discharge holes 413, the numbers of the corresponding cleaning liquid injection mechanisms 42 and cleaning liquid discharge mechanisms 43 are the same, and correspondingly, a corresponding number of groups of first magnetic members 481 and second magnetic members 482 are provided. That is, the magnetic separation cleaning device 4 has a multi-stage cleaning function, i.e., each reaction vessel can be subjected to the separation cleaning multiple times to ensure the cleaning effect, thereby increasing the detection accuracy of the sample.

In this embodiment, the number of the cleaning liquid injection mechanisms 42 and the number of the cleaning liquid discharge mechanisms 43 are both three, and the numbers and positions of the cleaning liquid intake holes 412 and the cleaning liquid discharge holes 413 are respectively adapted to the cleaning liquid injection mechanisms 42 and the cleaning liquid discharge mechanisms 43, that is, the reaction vessel can be subjected to three-stage cleaning to ensure the cleaning effect, thereby increasing the detection accuracy of the sample. Moreover, the cleaning positions between each cleaning liquid intake hole 412 and the cleaning liquid discharge hole 413 can be provided according to the number described above, and the first magnetic members 481 and the second magnetic members 482 are respectively provided, which will not be described in detail here. It should be noted that the number of cleaning positions between each group of the cleaning liquid intake hole 412 and the cleaning liquid discharge hole 413 may be the same or different. For example, the numbers of first-stage cleaning positions and second-stage cleaning positions are the same, particularly, the number of cleaning positions is three, namely two first cleaning positions 414 and one second cleaning position 415. For example, the numbers of first-stage cleaning positions and third-stage cleaning positions are different, particularly, the number of cleaning positions is four, namely three first cleaning positions 414 and one second cleaning position 415.

Particularly, when the magnetic separation cleaning device 4 performs three-stage cleaning on the reaction vessel, the reaction vessel is placed on the magnetic separation base 41 from the access hole 411, and the magnetic separation base 41 drives the reaction vessel to move to the first-stage cleaning liquid intake hole 412, and the cleaning liquid is added into the reaction vessel by the cleaning liquid injection mechanism 42. The magnetic separation base 41 then drives the reaction vessel to move to the first-stage cleaning liquid discharge hole 413. During the movement, the reaction vessel sequentially passes through two first cleaning positions 414 and one second cleaning position 415 and is subjected to attraction by the first magnetic members 481 and the second magnetic member 482, respectively, such that the magnetic particles are loosened and relatively moved in the cleaning liquid, to achieve the first-stage cleaning, and the waste cleaning liquid is discharged through the cleaning liquid discharge hole 413 by the cleaning liquid discharge mechanism 43. The magnetic separation base 41 drives the reaction vessel from the first-stage cleaning liquid discharge hole 413 to the second-stage cleaning liquid intake hole 412, to perform the second-stage cleaning. It can be understood that the second-stage cleaning and the third-stage cleaning are exactly the same as the first-stage cleaning, just repeatedly performing the actions, and they will not be described in detail again. After the third-stage cleaning is completed, the magnetic separation base 41 drives the reaction vessel to return back to the access hole 411, and the reaction vessel grasping device 5 removes the reaction vessel. As an example, both the first magnetic member 481 and the second magnetic member 482 are magnets.

The various technical features of the embodiments described above can be arbitrarily combined. In order to simplify the description, all possible combinations of the various technical features in the above embodiments have not been described. However, any combination of these technical features should be considered to fall within the scope of the disclosure of this description as long as there is no contradiction.

The above-mentioned embodiments merely represent several implementations of the present disclosure, giving specifics and details thereof, but should not be understood as limiting the scope of the present patent of disclosure thereby. It should be noted that a person of ordinary skill in the art could also make several variations and improvements without departing from the concept of the present disclosure, and these variations and improvements would all fall within the scope of protection of the present disclosure. Therefore, the scope of protection of the invention shall be in accordance with the appended claims.

What is claimed is:

1. A fully automated chemiluminescence immunoassay analyzer, comprising:
   a sample and reagent receiving device for receiving a sample and a reagent, wherein the sample and reagent receiving device comprises a sample receiving mechanism for receiving the sample and a reagent receiving mechanism for receiving the reagent, the sample receiving mechanism is sleeved outside the reagent receiving mechanism, and the sample receiving mechanism and the reagent receiving mechanism are capable of rotating independently of each other;
   a dispensing device for aspirating and discharging the sample and the reagent, wherein the dispensing device is located above the sample and reagent receiving device, and respectively transfers the sample and the reagent into a reaction vessel in a mixing device;
   the mixing device for mixing the sample and the reagent in the reaction vessel;
   an incubation and luminescence detection device for incubation and luminescence detection;
   a magnetic separation cleaning device for separation cleaning an analyte and impurities in the reaction vessel;
   a reaction vessel grasping device for transferring the reaction vessel, wherein the reaction vessel grasping device transfers the reaction vessel into the mixing device, transfers the reaction vessel from the mixing device to the incubation and luminescence detection device to perform the incubation, transfers the reaction vessel to the magnetic separation cleaning device to perform the separation cleaning after the incubation, and transfers the reaction vessel into the incubation and luminescence detection device to perform the luminescence detection after the separation cleaning; and
   a liquid path device respectively connected to the dispensing device and the magnetic separation cleaning device, wherein the liquid path device is configured to inject or discharge a cleaning liquid into or from the magnetic separation cleaning device,
   wherein the incubation and luminescence detection device comprises a sample incubation mechanism and a sample detection mechanism, wherein the sample detection mechanism detects the reaction vessel;
   the sample incubation mechanism comprises an incubation block and a heating component configured to heat the incubation block, the incubation block is provided with a plurality of incubation holes arranged in an array, and each of the incubation holes is configured to receive the reaction vessel; and
   the sample detection mechanism is disposed on the sample incubation mechanism, and located at a side face of the incubation block,
   wherein the incubation block is provided with a luminescence detection hole arranged corresponding to the sample detection mechanism, wherein the luminescence detection hole is within the incubation block, and wherein the luminescence detection hole is configured to accommodate the reaction vessel, the reaction vessel after the incubation is transferred from one of the incubation holes into the luminescence detection hole, and the reaction vessel accommodated in the luminescence detection hole is detected by the sample detection mechanism.

2. The fully automated chemiluminescence immunoassay analyzer of claim 1, wherein the sample receiving mechanism comprises a plurality of sample holders arranged in an arc shape, a sample receiving driving structure, and a chassis, wherein each of the sample holders is configured to carry sample vessels with samples, the sample holders are sequentially installed on the chassis, and the sample receiving driving structure drives the chassis to rotate, so as to drive the sample holders on the chassis to rotate.

3. The fully automated chemiluminescence immunoassay analyzer of claim 1, wherein the reagent receiving mechanism comprises a reagent housing, a reagent disc, and a reagent disc driving structure, wherein the reagent disc is accommodated in the reagent housing, the reagent disc is configured to store reagent vessels with reagents, and the reagent disc driving structure drives the reagent disc to rotate.

4. The fully automated chemiluminescence immunoassay analyzer of claim 3, wherein the reagent receiving mechanism further comprises a cooling structure having a cooling component and a cold-end spreader, wherein the cooling component is located below the reagent disc and offset from a center of the reagent housing for cooling an interior of the reagent housing, and the cold-end spreader is connected to a cold end of the cooling component and located below the reagent disc.

5. The fully automated chemiluminescence immunoassay analyzer of claim 4, wherein the reagent receiving mechanism further comprises a hot-end radiator having a heat-conducting component, wherein the hot-end radiator is connected to a hot end of the cooling component and located on an outer side of the reagent housing.

6. The fully automated chemiluminescence immunoassay analyzer of claim 3, wherein the reagent receiving mechanism further comprises a reagent housing lid that covers the reagent housing; and
   the reagent housing lid is provided with a plurality of reagent aspiration holes that are arranged in a radial direction of the reagent disc and located on a straight line, and the dispensing device is capable of entering into any one of the reagent aspiration holes to aspirate the reagent; and
   wherein the reagent housing lid comprises a condensation structure that is provided on the reagent housing lid, the reagent aspiration holes are located in the condensation structure, and the condensation structure is configured to receive condensed water generated at the reagent aspiration holes.

7. The fully automated chemiluminescence immunoassay analyzer of claim 6, wherein the condensation structure comprises a condensation plate and a water receiving tray arranged opposite each other, the condensation plate is detachably connected to the water receiving tray, an airflow channel is formed between the condensation plate and the water receiving tray, and cold air in the reagent housing is capable of entering into the airflow channel;
- each of the reagent aspiration holes comprises a first reagent aspiration hole located in the condensation plate and a second reagent aspiration hole located in the water receiving tray; and the first reagent aspiration hole and the second reagent aspiration hole are arranged opposite each other, an outline of the first reagent aspiration hole covers an outline of the second reagent aspiration hole, and the first reagent aspiration hole is respectively in communication with the airflow channel and an outside environment.

8. The fully automated chemiluminescence immunoassay analyzer of claim 3, wherein the sample and reagent receiving device further comprises an identification code scanner for scanning an identification code, and the sample receiving mechanism is provided with a scanning notch; and
- the identification code scanner is capable of scanned identification codes of the sample vessels on sample receiving mechanism through the scanning notch, and the identification code scanner is further capable of scanning identification codes of the reagent vessels on the reagent receiving mechanism through the scanning notch;
- the reagent housing is provided with a scanning window, and the scanning window, the scanning notch and the identification code scanner correspond to one another, the reagent disc drives the reagent vessels to rotate, such that the reagent vessels are sequentially moved to the scanning window, and the identification code scanner scans the identification codes of the reagent vessels.

9. The fully automated chemiluminescence immunoassay analyzer of claim 1, wherein the mixing device comprises two mixing mechanisms, a mixing driving structure and a mixing seat, and the mixing driving structure drives each of the mixing mechanisms to move, so as to mix the sample and the reagent in the reaction vessel on the mixing device;
- the mixing seat comprises a reagent and sample mixing seat and a substrate mixing seat, the reagent and sample mixing seat is configured to carry the reaction vessel with the sample and the reagent and to mix the sample and the reagent in the reaction vessel, the substrate mixing seat is configured to carry the reaction vessel or another reaction vessel with a substrate and to mix the analyte and the substrate in the reaction vessel, and the mixing driving structure respectively drives, via the two mixing mechanisms, the reagent and sample mixing seat and the substrate mixing seat to perform mixing operations simultaneously.

10. The fully automated chemiluminescence immunoassay analyzer of claim 1, wherein the dispensing device comprises a dispensing needle, a horizontal movement mechanism and a vertical movement mechanism, wherein the vertical movement mechanism is provided on the horizontal movement mechanism, the dispensing needle is provided on the vertical movement mechanism and is in communication with the liquid path device, and movements of the vertical movement mechanism and the horizontal movement mechanism cause the dispensing needle to transfer the sample and the reagent between the sample and reagent receiving device and the mixing device; the dispensing device further comprises a first cleaning mechanism connected to the horizontal movement mechanism, wherein the first cleaning mechanism is in communication with the liquid path device, the horizontal movement mechanism drives the first cleaning mechanism to move, and when the vertical movement mechanism drives the dispensing needle to ascend or descend, the first cleaning mechanism cleans an outer wall of the dispensing needle.

11. The fully automated chemiluminescence immunoassay analyzer of claim 10, wherein the dispensing device comprises a second cleaning mechanism, wherein the second cleaning mechanism is connected to the liquid path device, and the second cleaning mechanism is configured to receive a waste cleaning liquid after an inner wall of the dispensing needle is cleaned, and the waste cleaning liquid is discharged by the liquid path device.

12. The fully automated chemiluminescence immunoassay analyzer of claim 1, wherein the incubation block is further provided with a waste liquid discharge hole arranged adjacent to the luminescence detection hole, the reaction vessel is transferred from the luminescence detection hole into the waste liquid discharge hole, and a waste liquid in the reaction vessel is discharged by the liquid path device.

13. The fully automated chemiluminescence immunoassay analyzer of claim 1, wherein the sample incubation mechanism further comprises a substrate heat-conducting structure having a substrate tube and a substrate heat-conducting block, wherein the substrate tube and the substrate heat-conducting block are both disposed in the incubation block, and the substrate heat-conducting block is configured to heat a substrate in the substrate tube.

14. The fully automated chemiluminescence immunoassay analyzer of claim 1, wherein the sample incubation mechanism further comprises a cleaning liquid heat-conducting container, which is disposed in the incubation block for heating the cleaning liquid, and is capable of delivering the heated cleaning liquid into the reaction vessel.

15. The fully automated chemiluminescence immunoassay analyzer of claim 1, further comprising a waste liquid discharge device, which is connected to the liquid path device and configured to discharge a waste liquid from the reaction vessel after being detected by the incubation and luminescence detection device; and
- while discharging the waste liquid, the waste liquid discharge device is further capable of shielding the reaction vessel from light, when the reaction vessel is being subjected to the luminescence detection in the incubation and luminescence detection device.

16. The fully automated chemiluminescence immunoassay analyzer of claim 1, wherein the magnetic separation cleaning device comprises a magnetic separation base, a cleaning liquid injection mechanism, a cleaning liquid discharge mechanism and a magnetic separation attraction mechanism, wherein
- the magnetic separation base is provided with an access hole, at least one cleaning liquid intake hole and at least one cleaning liquid discharge hole provided in sequence, the access hole being configured to receive or remove the reaction vessel to be separated and cleaned; the magnetic separation base drives the reaction vessel to rotate such that the reaction vessel sequentially corresponds to the cleaning liquid intake hole, the cleaning liquid discharge hole and the access hole; the cleaning liquid injection mechanism is connected to the liquid path device and provided in the cleaning liquid intake hole for adding the cleaning liquid into the reaction vessel; the cleaning liquid discharge mechanism is connected to the liquid path device and arranged in a liftable manner corresponding to the cleaning liquid discharge hole, for discharging the waste cleaning liquid from the reaction vessel; and the magnetic separation attraction mechanism is provided in the magnetic separation base and located on two sides of a rotation path of the reaction vessel.

17. The fully automated chemiluminescence immunoassay analyzer of claim 16, wherein the magnetic separation cleaning device further comprises a separation cleaning mechanism, and a liquid discharge ascending/descending mechanism located in a liftable manner on the magnetic separation base; the cleaning liquid discharge mechanism comprises a cleaning liquid discharge needle provided on the liquid discharge ascending/descending mechanism, the separation cleaning mechanism is provided in the cleaning liquid discharge hole, and when the liquid discharge ascending/descending mechanism drives the liquid discharge needle to ascend or descend, the separation cleaning mechanism cleans an outer wall of the liquid discharge needle.

18. The fully automated chemiluminescence immunoassay analyzer of claim 16, wherein the at least one cleaning liquid intake hole comprises three cleaning liquid intake holes and the at least one cleaning liquid discharge hole comprises three cleaning discharge holes, and each of the three cleaning liquid intake holes and each of the three cleaning liquid discharge holes are alternately placed in a circumferential direction of the magnetic separation base.

19. The fully automated chemiluminescence immunoassay analyzer of claim 16, wherein the magnetic separation cleaning device further comprises a magnetic shielding component, the magnetic shielding component being sleeved outside the magnetic separation base for shielding a magnetic field generated by the magnetic separation attraction mechanism.

20. The fully automated chemiluminescence immunoassay analyzer of claim 1, further comprising: a carrying platform, a reaction vessel receiving device, a waste box, a main control device, and a power supply device, wherein
the sample and reagent receiving device is located at one side edge of the carrying platform and provided on a side of the incubation and luminescence detection device away from the magnetic separation cleaning device, for carrying and automatically delivering the reaction vessel;
the incubation and luminescence detection device, the magnetic separation cleaning device and the reaction vessel receiving device are located at the other side edge of the carrying platform;
the mixing device is located between the incubation and luminescence detection device and the sample and reagent receiving device;
the liquid path device is located below the carrying platform; the reaction vessel grasping device is located at an edge of the carrying platform and above the reaction vessel receiving device; and
the dispensing device is located above the sample and reagent receiving device;
the power supply device is electrically connected to the main control device;
the main control device is electrically connected to the sample and reagent receiving device, the dispensing device, the incubation and luminescence detection device, the magnetic separation cleaning device, the reaction vessel grasping device, the reaction vessel receiving device and the liquid path device respectively; and
the main control device and the power supply device are located below the carrying platform.

21. The fully automated chemiluminescence immunoassay analyzer of claim 1, wherein the liquid path device further comprises a magnetic separation cleaning liquid path system, and the magnetic separation cleaning device is provided with a liquid injection needle; the magnetic separation cleaning liquid path system comprises a magnetic separation power source, a magnetic separation liquid aspiration pipeline, a magnetic separation liquid injection pipeline and a first magnetic separation control valve;
the magnetic separation power source is respectively connected to the magnetic separation liquid aspiration pipeline and the magnetic separation liquid injection pipeline via the first magnetic separation control valve; the magnetic separation liquid aspiration pipeline is in communication with a cleaning liquid container with the cleaning liquid, and the magnetic separation liquid injection pipeline is connected to the liquid injection needle;
the first magnetic separation control valve connects the magnetic separation power source with the magnetic separation liquid aspiration pipeline and disconnects the magnetic separation power source from the magnetic separation liquid injection pipeline, so that the cleaning liquid is capable of being aspirated from the cleaning liquid container; and the first magnetic separation control valve connects the magnetic separation power source with the magnetic separation liquid injection pipeline and disconnects the magnetic separation power source from the magnetic separation liquid aspiration pipeline, so that the cleaning liquid is capable of being injected into the reaction vessel;
the magnetic separation cleaning device is provided with a separation cleaning mechanism and a cleaning liquid discharge needle; the magnetic separation cleaning liquid path system further comprises a first magnetic separation cleaning pipeline, a third magnetic separation control valve and a fourth magnetic separation control valve;
the first magnetic separation cleaning pipeline connects the magnetic separation liquid injection pipeline to the separation cleaning mechanism, and the third magnetic separation control valve is provided on the first magnetic separation cleaning pipeline for controlling opening and closing of the first magnetic separation cleaning pipeline; the fourth magnetic separation control valve is provided on the magnetic separation liquid injection pipeline; and
the magnetic separation power source is in communication with the first magnetic separation cleaning pipeline via the magnetic separation liquid injection pipeline, and the fourth magnetic separation control valve closes the magnetic separation liquid injection pipeline to clean an outer wall of the liquid injection needle.

22. The fully automated chemiluminescence immunoassay analyzer of claim 21, wherein the magnetic separation cleaning liquid path system further comprises a magnetic separation liquid discharge pipeline, a second magnetic separation control valve, a magnetic separation drive source, and a recovery pipeline;
the magnetic separation liquid discharge pipeline connects the magnetic separation drive source to the liquid discharge needle, and the second magnetic separation control valve is provided on the magnetic separation liquid discharge pipeline for discharging waste cleaning liquid from the reaction vessel; and the magnetic separation drive source is further connected to the recovery pipeline, and the waste cleaning liquid in the reaction vessel is discharged into a waste liquid bucket through the recovery pipeline;

the magnetic separation cleaning liquid path system further comprises a second magnetic separation cleaning pipeline and a fifth magnetic separation control valve; the second magnetic separation cleaning pipeline connects the separation cleaning mechanism to the magnetic separation drive source, the fifth magnetic separation control valve is provided on the second magnetic separation cleaning pipeline for controlling opening and closing of the second magnetic separation cleaning pipeline, and the waste cleaning liquid is discharged into the waste liquid bucket by the magnetic separation drive source;

the magnetic separation drive source comprises a negative pressure chamber, a vacuum pump, and a negative pressure sensor, wherein the negative pressure chamber connects the magnetic separation liquid discharge pipeline to the recovery pipeline, the vacuum pump is provided on the recovery pipeline, the negative pressure sensor is configured to detect a pressure of the negative pressure chamber, and the pressure is adjusted by the vacuum pump.

* * * * *